United States Patent
Kumagai et al.

(10) Patent No.: US 7,528,124 B2
(45) Date of Patent: May 5, 2009

(54) 1,3-DIHYDRO-2H-INDOL-2-ONE DERIVATIVE

(75) Inventors: Toshihito Kumagai, Tokyo (JP); Takeshi Kuwada, Tokyo (JP); Tsuyoshi Shibata, Tokyo (JP); Masato Hayashi, Tokyo (JP); Yuri Fujisawa, Tokyo (JP); Yoshinori Sekiguchi, Tokyo (JP)

(73) Assignee: Taisho Pharmaceutical Co., Ltd., Tokyo (JP)

( * ) Notice: Subject to any disclaimer, the term of this patent is extended or adjusted under 35 U.S.C. 154(b) by 461 days.

(21) Appl. No.: 10/569,833

(22) PCT Filed: Aug. 27, 2004

(86) PCT No.: PCT/JP2004/012398

§ 371 (c)(1),
(2), (4) Date: Feb. 28, 2006

(87) PCT Pub. No.: WO2005/021534

PCT Pub. Date: Oct. 3, 2005

(65) Prior Publication Data

US 2006/0276449 A1    Dec. 7, 2006

(30) Foreign Application Priority Data

Aug. 28, 2003  (JP) .............................. 2003-209401

(51) Int. Cl.
*A61K 31/404* (2006.01)
*C07D 209/04* (2006.01)
*C07D 403/04* (2006.01)

(52) U.S. Cl. ................. 514/183; 514/414; 548/466

(58) Field of Classification Search .............. 514/183
See application file for complete search history.

(56) References Cited

U.S. PATENT DOCUMENTS

| 6,596,732 | B2 | 7/2003 | Serradeil-Le Gal et al. |
| 6,624,164 | B2 | 9/2003 | Schoentjes et al. |
| 6,730,695 | B2 * | 5/2004 | Roux et al. ................. 514/414 |
| 6,864,277 | B2 | 3/2005 | Roux et al. |
| 2004/0080878 | A1 | 4/2004 | Brollo |
| 2005/0092335 | A1 | 5/2005 | Bertrand et al. |

FOREIGN PATENT DOCUMENTS

| JP | 2003-523351 A | 8/2003 |
| JP | 2003-523354 A | 8/2003 |
| JP | 2003-525287 A | 8/2003 |
| WO | WO 01/98295 A1 | 12/2001 |
| WO | WO 03/008407 A2 | 1/2003 |
| WO | WO 2004/009585 A2 | 1/2004 |

* cited by examiner

*Primary Examiner*—Ardin Marschel
*Assistant Examiner*—Meghan Finn
(74) *Attorney, Agent, or Firm*—Sughrue Mion, PLLC

(57) ABSTRACT

A 1,3-dihydro-2H-indol-2-one derivative expressed by Formula 1 (wherein $R_1$ is a halogen atom, a $C_1$ to $C_4$ alkyl group, etc., and $R_2$ is a hydrogen atom, a halogen atom, etc., or $R_2$ is in the 6-position of the indol-2-one and $R_1$ and $R_2$ join together to form a $C_3$ to $C_6$ alkylene group, $R_3$ is a halogen atom, a hydroxyl group, etc., and $R_4$ is a hydrogen atom, a halogen atom, a $C_1$ to $C_4$ alkyl group, etc., or $R_4$ is in the 3-position of the phenyl and $R_3$ and $R_4$ join together to form a methylenedioxy group, $R_5$ is a hydrogen atom or a fluorine atom, $R_6$ is an ethylamino group, a dimethylamino group, etc., $R_7$ is a $C_1$ to $C_4$ alkoxy group, and $R_8$ is a $C_1$ to $C_4$ alkoxy group), or a pharmaceutically acceptable salt of this derivative. This is a novel compound that has antagonistic activity against an aruginine-vasopressin V1b receptor.

8 Claims, No Drawings

1,3-DIHYDRO-2H-INDOL-2-ONE DERIVATIVE

TECHNICAL FIELD

This invention relates to a 1,3-dihydro-2H-indol-2-one derivative, a method for manufacturing thereof, and intermediates thereof, and more particularly relates to a 1,3-dihydro-2H-indol-2-one derivative that has antagonistic activity against an arginine-vasopressin V1b receptor and is useful in preventing or treating diseases such as depression, anxiety, Alzheimer's disease, Parkinson's disease, Huntington's disease, eating disorders, hypertension, gastrointestinal diseases, drug dependence, epilepsy, cerebral infarction, cerebral ischemia, cerebral edema, head trauma, inflammation, immunological diseases, and alopecia, a method for manufacturing thereof, and intermediates thereof.

BACKGROUND ART

Arginine-vasopressin (AVP) is a peptide composed of nine amino acids, which is synthesized mainly in the hypothalamus, and as a posterior pituitary hormone it is closely related to the regulation of plasma osmotic pressure, blood pressure, and body fluid level.

Three sub-types of AVP receptor, namely, V1a, V1b, and V2 receptors, have been cloned, and all are known to be "seven transmembrane receptors". The V2 receptor couples with Gs and increases the cAMP level. The V1a receptor couples with Gq/11, promotes PI response, increases intracellular Ca, is expressed in the brain, liver, adrenal gland, vascular smooth muscle, and so on, and is involved in vascular contraction. Meanwhile, the V1b receptor is similar to the V1a receptor in that it couples with Gq/11 and promotes PI response (Non-Patent Documents 1 and 2). The V1b receptor is most prevalent in the pituitary gland (expressed in over 90% of ACTH-secreting cells of the anterior lobe), and has been presumed to be involved in ACTH secretion from the anferior lobe of pituitary by AVP. In addition to being found in the pituitary, the V1b receptor is also found over a wide region of the brain, and is also prevalent in the raphe nuclei, which are the nuclei of serotonergic neurons, the cerebral cortex, and the olfactory bulb, and parts of the limbic system such as the hippocampus, amygdala, and entorhinal cortex (Non-Patent Documents 3 and 4).

Relationship between the V1b receptor and depression and anxiety disorders has recently been suggested, and the usefulness of a V1b receptor antagonist has been studied. It has been indicated that aggressive behavior is reduced in V1b receptor KO mice (Non-Patent Document 5). It has also been reported that injection of a V1b receptor antagonist into the septum prolongs the time on open-arms in an elevated plus maze test (anxiolytic action) (Non-Patent Document 6). More recently, a V1b receptor-specific antagonist has been synthesized that is a systemically administrable 1,3-dihydro-2H-indol-2-one derivative (Non-Patent Documents 1 to 6). Also, 1,3-dihydro-2H-indol-2-one derivatives have been reported exhibit antidepressant and anxiolytic effects in various animal models (Non-Patent Documents 7 and 8). The compound disclosed in Patent Document 1 exhibits high affinity (1 to $4 \times 10^{-9}$ mol/L) and selectivity towards a V1b receptor, and is antagonistic to AVP, AVP+CRF, and restraint stress-induced ACTH increase.

However, Patent Documents 1 to 6 do not disclose a compound which a fluorine atom has been introduced into a pyrrolidine ring bonded to the 3-position of 1,3-dihydro-2H-indol-2-one.

Non-Patent Document 1: Sugimoto T., Kawashima G, J. Biol. Chem., 269, 27088-27092, 1994.

Non-Patent Document 2: Lolait S., Brownstein M., PNAS, 92, 6783-6787, 1995.

Non-Patent Document 3: Vaccari C., Ostrowski N., Endocrinology, 139, 5015-5033, 1998.

Non-Patent Document 4: Hernando F., Burbach J., Endocrinology, 142, 1659-1668, 2001.

Non-Patent Document 5: Wersinger S. R., Toung W. S., Mol. Psychiatry, 7, 975-984, 2002.

Non-Patent Document 6: Liebsch G., Engelmann M., Neurosci. Lett., 217, 101-104, 1996.

Non-Patent Document 7: Gal C. S., Le Fur G., 300, 1122-1130, 2002.

Non-Patent Document 8: Griebel G., Soubrie P., 99, 6370a-6375, 2002.

Patent Document 1: WO01/55130 pamphlet
Patent Document 2: WO01/55134 pamphlet
Patent Document 3: WO01/64668 pamphlet
Patent Document 4: WO01/98295 pamphlet
Patent Document 5: WO03/008407 pamphlet
Patent Document 6: WO2004/009585 pamphlet

DISCLOSURE OF THE INVENTION

Problems to be Solved by the Present Invention

It is an object of the present invention to provide a drug that is effective against pathology related to an arginine-vasopressin V1b receptor. More particularly, it is to provide a drug that is effective in preventing or treating diseases such as depression, anxiety, Alzheimer's disease, Parkinson's disease, Huntington's disease, eating disorders, hypertension, gastrointestinal diseases, drug dependence, epilepsy, cerebral infarction, cerebral ischemia, cerebral edema, head trauma, inflammation, immunological diseases, and alopecia.

Means for Solving the Above Problems

As a result of diligent study, the inventors complete the present invention upon discovering a novel 1,3-dihydro-2H-indol-2-one derivative that is selectively antagonistic toward an aruginine-vasopressin V1b receptor, has excellent metabolic stability, and exhibits good intracerebral migration and high serum concentration.

Specifically, the present invention is a 1,3-dihydro-2H-indol-2-one derivative expressed by Formula 1:

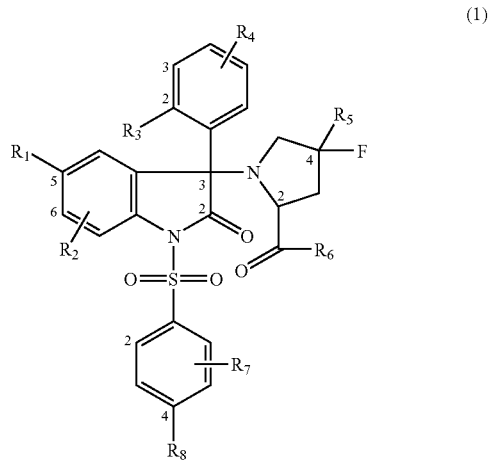

(1)

(wherein $R_1$ is a halogen atom, a $C_1$ to $C_4$ alkyl group, a $C_1$ to $C_4$ alkoxy group, a trifluoromethyl group, or a trifluoromethoxy group, $R_2$ is a hydrogen atom, a halogen atom, a $C_1$ to $C_4$ alkyl group, a $C_1$ to $C_4$ alkoxy group, or a trifluoromethyl group, or $R_2$ is in the 6-position of the indol-2-one and $R_1$ and $R_2$ join together to form a $C_3$ to $C_6$ alkylene group, R₃ is a halogen atom, a hydroxyl group, a $C_1$ to $C_4$ alkyl group, a $C_1$ to $C_4$ alkoxy group, or a trifluoromethoxy group, R₄ is a hydrogen atom, a halogen atom, a $C_1$ to $C_4$ alkyl group, or a $C_1$ to $C_4$ alkoxy group, or R₄ is in the 3-position of the phenyl and R₃ and R₄ join together to form a methylenedioxy group, R₅ is a hydrogen atom or a fluorine atom, R₆ is an ethylamino group, a dimethylamino group, an azetidin-1-yl group, or a $C_1$ to $C_4$ alkoxy group, R₇ is a $C_1$ to $C_4$ alkoxy group, and R₈ is a $C_1$ to $C_4$ alkoxy group), or a pharmaceutically acceptable salt thereof.

A preferred compound of Formula 1 is a 1,3-dihydro-2H-indol-2-one derivative, or a pharmaceutically acceptable salt thereof, wherein R₁ is a chlorine atom, a methyl group, a methoxy group, a trifluoromethyl group, or a trifluoromethoxy group, R₂ is a hydrogen atom, a chlorine atom, a methyl group, or a methoxy group, R₃ is a fluorine atom or a methoxy group, R₄ is a hydrogen atom, a chlorine atom, a methyl group, or a methoxy group, or R₄ is in the 3-position of the phenyl and R₃ and R₄ join together to form a methylenedioxy group, R₅ is a hydrogen atom or a fluorine atom, R₆ is a dimethylamino group, an azetidin-1-yl group, or a methoxy group, R₇ is a methoxy group and is in the 2-position of the phenyl, and R₈ is a methoxy group.

Even more preferably, the compound of Formula 1 is a 1,3-dihydro-2H-indol-2-one derivative or a pharmaceutically acceptable salt thereof, expressed by the Formula 1a:

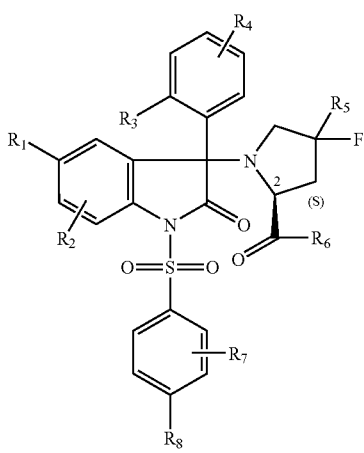

(1a)

(wherein R₁, R₂, R₃, R₄, R₅, R₆, R₇, and R₈ are the same as defined in Formula 1), in which the substituent in the 2-position of the pyrrolidine has the (S) configuration.

The compound of Formula 1a is preferably in the form of a levorotatory isomer.

Preferably, this compound is one of the compounds listed below:

(4R)-1-[5-chloro-1-[(2,4-dimethoxyphenyl)sulfonyl]-3-(2-methoxyphenyl)-2-oxo-2,3-dihydro-1H-indol-3-yl]-4-fluoro-N,N-dimethyl-L-prolinamide (levorotatory isomer);

(4S)-1-[5-chloro-1-[(2,4-dimethoxyphenyl)sulfonyl]-3-(2-methoxyphenyl)-2-oxo-2,3-dihydro-1H-indol-3-yl]-4-fluoro-N,N-dimethyl-L-prolinamide (levorotatory isomer);

1-[5-chloro-1-[(2,4-dimethoxyphenyl)sulfonyl]-3-(2-methoxyphenyl)-2-oxo-2,3-dihydro-1H-indol-3-yl]-4,4-difluoro-N,N-dimethyl-L-prolinamide (levorotatory isomer);

methyl(4S)-1-[5-chloro-1-[(2,4-dimethoxyphenyl)sulfonyl]-3-(2-methoxyphenyl)-2-oxo-2,3-dihydro-1H-indol-3-yl]-4-fluoro-L-prolinate (diastereoisomer mixture);

3-[(2S)-2-azetidin-1-ylcarbonyl)-4-fluoropyrrolidin-1-yl]-5-chloro-1-[(2,4-dimethoxyphenyl)sulfonyl]-3-(2-methoxyphenyl)-1,3-dihydro-2H-indol-2-one (levorotatory isomer);

(4R)-1-{3-(2,4-dimethoxyphenyl)-1-[(2,4-dimethoxyphenyl)sulfonyl]-5,6-dimethoxy-2-oxo-2,3-dihydro-1H-indol-3-yl}-4-fluoro-N,N-dimethyl-L-prolinamide (levorotatory isomer);

(4R)-1-[1-[(2,4-dimethoxyphenyl)sulfonyl]-3-(2-fluorophenyl)-2-oxo-5-(trifluoromethyl)-2,3-dihydro-1H-indol-3-yl]-4-fluoro-N,N-dimethyl-L-prolinamide (levorotatory isomer);

(4R)-1-[1-[(2,4-dimethoxyphenyl)sulfonyl]-3-(2-methoxyphenyl)-2-oxo-5-(trifluoromethoxy)-2,3-dihydro-1H-indol-3-yl]-4-fluoro-N,N-dimethyl-L-prolinamide (levorotatory isomer);

(4R)-1-[1-[(2,4-dimethoxyphenyl)sulfonyl]-3-(2-methoxyphenyl)-5-methyl-2-oxo-2,3-dihydro-1H-indol-3-yl]-4-fluoro-N,N-dimethyl-L-prolinamide (levorotatory isomer);

(4R)-1-[4,5-dichloro-1-[(2,4-dimethoxyphenyl)sulfonyl]-3-(2-methoxy-5-methylphenyl)-2-oxo-2,3-dihydro-1H-indol-3-yl]-4-fluoro-N,N-dimethyl-L-prolinamide (levorotatory isomer);

(4R)-1-{5-chloro-3-(5-chloro-2-methoxyphenyl)-1-[(2,4-dimethoxyphenyl)sulfonyl]-4-methyl-2-oxo-2,3-dihydro-1H-indol-3-yl}-4-fluoro-N,N-dimethyl-L-prolinamide (levorotatory isomer); and (4R)-1-{3-(1,3-benzodioxol-4-yl)-5-chloro-1-[(2,4-dimethoxyphenyl)sulfonyl]-2-oxo-2,3-dihydro-1H-indol-3-yl}-4-fluoro-N,N-dimethyl-L-prolinamide (levorotatory isomer).

Another aspect of the present invention is a method for manufacturing a 1,3-dihydro-2H-indol-2-one derivative expressed by Formula 1 by reacting a compound expressed by

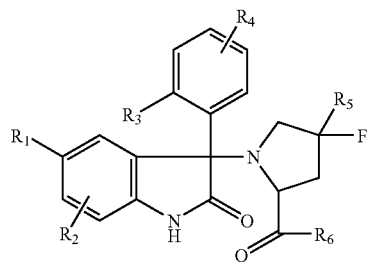

(2)

(wherein R₁, R₂, R₃, R₄, R₅, and R₆ are the same as defined in Formula 1) with a compound expressed by Formula 3:

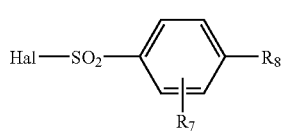

(3)

(wherein $R_7$ and $R_8$ are the same as defined in Formula 1, and Hal is a halogen atom) in the presence of a base.

Another aspect of the present invention is a compound expressed by Formula 2:

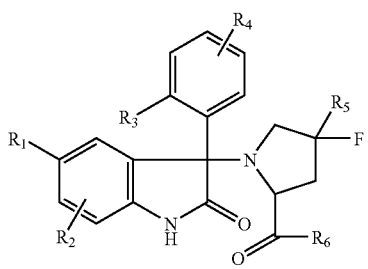

(wherein $R_1$, $R_2$, $R_3$, $R_4$, $R_5$, and $R_6$ are the same as defined in Formula 1), or a salt thereof, which is useful as a synthetic intermediate of the compound expressed by Formula 1.

Another aspect of the present invention is a pharmaceutical composition containing as an active ingredient the compound expressed by Formula 1 or a pharmaceutically acceptable salt thereof. The meritorious effect of the present invention The compound of the present invention is a selective vasopressin V1b receptor antagonist that has excellent metabolic stability and exhibits good intracerebral migration and high serum concentration, and is useful in preventing or treating diseases such as depression, anxiety, Alzheimer's disease, Parkinson's disease, Huntington's disease, eating disorders, hypertension, gastrointestinal diseases, drug dependence, epilepsy, cerebral infarction, cerebral ischemia, cerebral edema, head trauma, inflammation, immunological diseases, and alopecia.

BEST MODE FOR CARRYING OUT THE INVENTION

The term "halogen atom" as used in the present invention means a fluorine atom, chlorine atom, bromine atom, or iodine atom. A chlorine atom or fluorine atom is preferred.

The term "$C_1$ to $C_4$ alkyl group" means a linear or branched $C_1$ to $C_4$ alkyl group, and specifically a methyl group, ethyl group, propyl group, isopropyl group, butyl group, isobutyl group, or tert-butyl group. A methyl group is preferred.

The term "$C_1$ to $C_4$ alkoxy group" means a linear or branched $C_1$ to $C_4$ alkoxy group, and specifically a methoxy group, ethoxy group, propoxy group, isopropoxy group, butoxy group, isobutoxy group, or tert-butoxy group. A methoxy group is preferred.

The term "$C_3$ to $C_6$ alkylene group" means a trimethylene group, tetramethylene group, pentamethylene group, or hexamethylene group. A trimethylene group is preferred.

Pharmaceutically acceptable salts include, for example, salts of hydrochloric acid, hydrobromic acid, sulfuric acid, phosphoric acid and other such mineral acids, and salts of acetic acid, oxalic acid, lactic acid, tartaric acid, fumaric acid, maleic acid, succinic acid, trifluoroacetic acid, dichloroacetic acid, methanesulfonic acid, p-toluenesulfonic acid, naphthalenesulfonic acid, gluconic acid, benzenesulfonic acid, citric acid, and other such organic acids. The compound of the present invention can also be in the form of various solvates. Also, from the standpoint of applicability as a drug, a hydrate is sometimes preferable.

As long as it is a salt that can be used to synthesis the compound expressed by Formula 2, which is useful as an intermediate, there are no particular restrictions on the salt of this compound, and may be a mineral acid salt or an organic acid salt.

Mineral acid salts include, for example, hydrochlorides, hydrobromides, sulfates, phosphates, nitrates, hydrogensulfates, and dihydrogenphosphates.

Organic acid salts include, for example, acetates, oxalates, lactates, tartrates, fumarates, maleates, succinates, trifluoroacetates, dichloroacetates, methanesulfonates, p-toluenesulfonates, naphthalenesulfonates, gluconates, benzenesulfonates, and citrates.

The compound of the present invention also includes compounds in which one or more hydrogen atoms, carbon atoms, nitrogen atoms, oxygen atoms, or sulfur atoms have been substituted with a radioactive isotope or a stable isotope. These labeled compounds are useful in metabolic or pharmacokinetic research, or in biochemical analysis as receptor ligands.

The compound of the present invention can be pharmaceutically formulated by being combined with one or more pharmaceutically acceptable carriers, excipients, or diluents. Examples of such carriers, excipients, and diluents include water, lactose, dextrose, fructose, sucrose, sorbitol, mannitol, polyethylene glycol, propylene glycol, starch, gum, gelatin, alginate, calcium silicate, calcium phosphate, cellulose, aqueous syrup, methyl cellulose, polyvinylpyrrolidone, alkyl parahydroxybenzosorbate, talc, magnesium stearate, stearic acid, glycerin, sesame oil, olive oil, soy oil, and various other oils.

Also, the above carriers, excipients, and diluents can be mixed as needed with commonly used thickeners, binders, disintegrants, pH regulators, solvents, and other such additives, and can be prepared as tablets, pills, capsules, granules, a powder, a liquid, a lotion, a suspension, an ointment, an injection, a skin patch, or other oral or parenteral drug by a standard formulation technique. The compound of the present invention can be administered orally or parenterally to a patient one or more times per day in a dose of 0.001 to 500 mg. This dose can be suitably increased or decreased according to the type of disease to be treated, or the age, weight, symptoms, and so forth of the patient.

The compound of the present invention can be manufactured by the following method, for example.

The compound of the present invention can be manufactured by reacting a compound expressed by Formula 2:

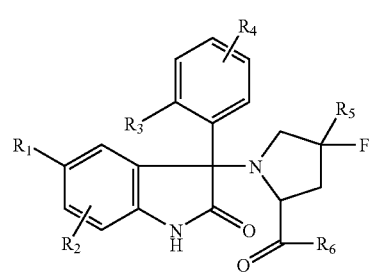

(wherein $R_1$, $R_2$, $R_3$, $R_4$, $R_5$, and $R_6$ are the same as defined in Formula 1) with a compound expressed by Formula 3:

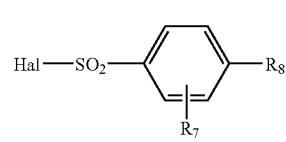

(wherein $R_7$ and $R_8$ are the same as defined in Formula 1, and Hal is a halogen atom) in the presence of a base. If necessary, the compound thus obtained can be converted into a pharmaceutically acceptable salt.

The reaction is conducted under the following conditions, for example: in the presence of a metal hydride such as sodium hydride or an alkali metal alkoxide such as potassium tert-butoxide, in a nonaqueous solvent such as N,N-dimethylformamide or tetrahydrofuran, or in a mixture of these solvents, and at a temperature from −70° C. to +60° C.

The compound of the present invention can be obtained by taking the reaction product out of the reaction mixture and purified it by a standard method, such as crystallization or chromatography.

The compound of the present invention can be obtained in a free form or isolated as a salt by a standard method. When the compound of the present invention is obtained in a free form, salt formation can be performed by treatment with an acid in an organic solvent. For instance, a free form can be dissolved along with an acid in diethyl ether or another ether, isopropyl alcohol or another alcohol, acetone, dichloromethane, ethyl acetate, acetonitrile, or the like, and the above-mentioned salt obtained by a standard method.

The acids that can be used include, for example, hydrochloric acid, hydrobromic acid, sulfuric acid, phosphoric acid, acetic acid, oxalic acid, lactic acid, tartaric acid, fumaric acid, maleic acid, succinic acid, trifluoroacetic acid, dichloroacetic acid, methanesulfonic acid, p-toluenesulfonic acid, naphthalenesulfonic acid, benzenesulfonic acid, gluconic acid, and citric acid.

At the end of this reaction, the compound of the present invention is sometimes isolated as a hydrochloride, oxalate, or the like, for example, but if necessary, a free form can be obtained by neutralizing the obtained salt with an alkali metal hydrogencarbonate or alkali metal carbonate such as sodium hydrogencarbonate or sodium carbonate, or triethylamine or sodium hydroxide.

The compound expressed by Formula 2 can be manufactured by reacting a 3-halo-1,3-dihydro-2H-indol-2-one derivative expressed by Formula 5:

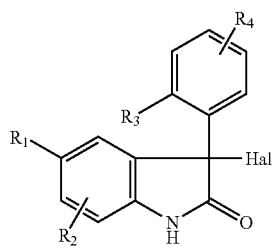

(5)

(wherein $R_1$, $R_2$, $R_3$, and $R_4$ are the same as defined in Formula 1, and Hal is a halogen atom) with a compound expressed by Formula 4:

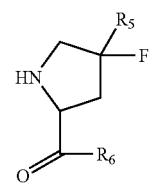

(4)

(wherein $R_5$ and $R_6$ are the same as defined in Formula 1), or a salt of this compound, in the presence of a base, such as diisopropylethylamine or triethylamine, in an inert solvent, such as dichloromethane or tetrahydrofuran, or in a mixture of these solvents, and at a temperature between room temperature and close to the boiling point of the solvent.

The compound expressed by Formula 3 is a known compound disclosed in EP0469984, WO95/18105, and elsewhere, and can be manufactured by the methods described in these publications. For instance, the compound expressed by Formula 3 can be manufactured by halogenating a benzenesulfonic acid derivative or a salt thereof, such as a sodium or potassium salt.

The reaction proceeds in the presence of a halogenating agent, such as thionyl chloride or phosphorus oxychloride, in a non-solvent or an inert solvent, such as a halogenated hydrocarbon, N,N-dimethylformamide, or another such solvent, and at a temperature from −10° C. to 200° C.

2,4-dimethoxybenzenesulfonyl chloride is commercially available, or can be manufactured according to the methods described in a publication (Journal of American Chemical Society, 1952, 74, 2006).

The compound expressed by Formula 5 can be manufactured, for example, by the methods described in WO95/18105, WO01/74775, WO01/55130, WO01/55134, WO01/64668, WO01/98295, WO03/008407, and elsewhere.

For example, a compound expressed by Formula 6a:

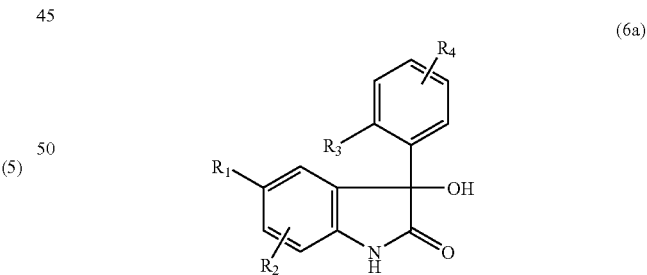

(6a)

(wherein $R_1$, $R_2$, $R_3$, and $R_4$ are the same as defined in Formula 1) can be converted into a compound expressed by Formula 5 (Hal=Cl) by causing thionyl chloride to act on the compound in the presence of a base such as pyridine, in an inert solvent such as dichloromethane, and at a temperature between 0° C. and room temperature.

In another method for manufacturing a compound expressed by Formula 5, a compound expressed by Formula 6b:

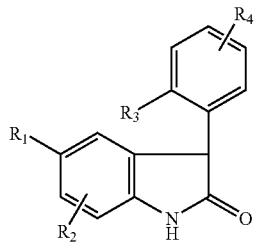

(6b)

(wherein $R_1$, $R_2$, $R_3$, and $R_4$ are the same as defined in Formula 1) can be converted by using a halogenating agent such as bromine or N-chlorosuccinimide according to the method described in a publication (Farm. Zh. (K-iev), 1976, 5, 30-33).

The compound expressed by Formula 6a can be manufactured, for example, by the methods described in WO95/18105, WO01/74775, WO01/55130, WO01/55134, WO01/64668, WO01/98295, WO03/008407, and elsewhere.

The compound expressed by Formula 4 generally can be manufactured by the synthesis route shown in Scheme 1. Pr is a protective group for a nitrogen atom, and in particular is a benzyloxycarbonyl group or tert-butoxycarbonyl group.

In step 1-1a of Scheme 1, a compound 8 can be manufactured by introducing a protective group according to a standard method to a nitrogen atom of compound 7: (4R)- or (4S)-4-hydroxy-L-proline or (4R)- or (4S)-4-hydroxy-D-proline. In the subsequent step 1-2a, a compound 10 can be manufactured by the esterification or amidation of compound 8 according to a standard method. Similarly, a compound 9 can be manufactured by the esterification or amidation of the carboxylic acid of compound 7 in step 1-1b according to a standard method, and compound 10 can then be manufactured by introducing a protective group (step 1-2b) according to a standard method to a nitrogen atom of the obtained compound 9.

The amidation reaction is generally as follows. A method involving the use of a dehydrating condensation agent is an example. Examples of dehydrating condensation agents include 1-ethyl-3-(3-dimethylaminopropyl)carbodiimide hydrochloride, dicyclohexylcarbodiimide, diphenylphosphonylazide, and carbonyldiimidazole. If necessary, an activator such as 1-hydroxybenzotriazole or hydroxysuccinimide can be used. Examples of the reaction solvent include dichloromethane, chloroform, 1,2-dichloroethane, N,N-dimethylformamide, tetrahydrofuran, dioxane, toluene, ethyl acetate, and mixtures of these solvents. A base can be used here, and examples of the base include triethylamine, diisopropylethylamine, and other such organic amines, sodium 2-ethylhexanoate, potassium 2-ethylhexanoate, and other such organic acid salts, and potassium carbonate and other such inorganic bases. The reaction can be conducted between −50° C. and close to the boiling point of the reaction solvent.

Also, amidation can be performed using a mixed acid anhydride obtained from a carboxylic acid and a chlorocarbonic ester, for example. Examples of the solvent used in these reactions include tetrahydrofuran, dioxane, dichloromethane, chloroform, N,N-dimethylformamide, toluene, ethyl acetate, and other solvents that do not participate in the reaction, or a mixture of these solvents. A base can be used here, and examples of the base include triethylamine, diisopropylethylamine, and other such organic amines, sodium 2-ethylhexanoate, potassium 2-ethylhexanoate, and other such organic acid salts, and potassium carbonate and other such inorganic bases. The reaction can be conducted between −50° C. and close to the boiling point of the reaction solvent.

Common esterification reactions of a carboxylic acid include the following. For example, methyl esterification can be performed by using diazomethane or another such diazo compound. The solvent used here can be dichloromethane, chloroform, methanol, ethanol, or another such solvent, or a mixture of these solvents. Further, esterification can be performed by converting a carboxylic acid into an acid halide, and causing an alcohol compound to act on this product. An acid halide can be produced by using thionyl chloride, thionyl bromide, phosphorus oxychloride, or the like. Examples of the solvent used here include dichloromethane, chloroform, N,N-dimethylformamide, toluene, tetrahydrofuran, and other solvents that do not participate in the reaction, or a mixture of these solvents. Esterification can be performed by subjecting the acid halide thus prepared to the action of an alcohol such as methanol or ethanol. This reaction is brought about by adding an alcohol to the acid halogenation reaction system, or may involve subjecting an isolated acid halide to the action of an alcohol.

Another possible method is one involving the use of a dehydrating condensation agent. Examples of dehydrating condensation agents include 1-ethyl-3-(3-dimethylaminopropyl)carbodiimide hydrochloride, dicyclohexylcarbodiimide, diphenylphosphonylazide, and carbonyldiimidazole. Examples of the reaction solvent include dichloromethane, chloroform, 1,2-dichloroethane, N,N-dimethylformamide, tetrahydrofuran, dioxane, toluene, ethyl acetate, and mixtures of these solvents. A base can be used here, and examples of the base include triethylamine, diisopropylethylamine, 4-(dimethylamino)pyridine, and other such amines, sodium 2-ethylhexanoate, potassium 2-ethylhexanoate, and other such organic acid salts, and potassium carbonate and other such inorganic bases. The reaction can be conducted between −50° C. and close to the boiling point of the reaction solvent.

Also, esterification can be performed using a mixed acid anhydride obtained from a carboxylic acid and a chlorocarbonic ester, or di-tert-butyl dicarbonate, for example. Examples of the solvent used in these reactions include tetrahydrofuran, dioxane, dichloromethane, chloroform, N,N-dimethylformamide, toluene, ethyl acetate, and other solvents that do not participate in the reaction, or a mixture of these solvents. A base can be used here, and examples of the base include triethylamine, diisopropylethylamine, 4-(dimethylamino)pyridine, and other such organic amines, sodium 2-ethylhexanoate, potassium 2-ethylhexanoate, and other such organic acid salts, and potassium carbonate and other such inorganic bases. The reaction can be conducted between −50° C. and close to the boiling point of the reaction solvent.

At some point in the process of preparing the compound defined by Formula 4, or an intermediate thereof, it will probably be necessary or desirable to protect reactive or sensitive functional groups, such as amines and carboxylic acids, present in any of the molecules concerned. This protection can be accomplished using conventional protecting groups, such as those described in Protective Groups in Organic Chemistry, by J. F. W. McOmie, published in 1973 by Plenum Press, or in Protective Groups in Organic Synthesis, by T. W. Greene and P. G. M. Wuts, published in 1991 by John Wiley & Sons. The protecting groups also be removed by the methods outlined in the above two booklets.

The protection of amino groups can be carried out, for example, using di-tert-butyl dicarbonate, benzyl chloroformate, or the like, and in the presence of a suitable base. Examples of the base include triethylamine, diisopropylethylamine, and other such amines, and potassium carbonate and other such inorganic bases. Examples of the solvent used in these reactions include tetrahydrofuran, dioxane, dichloromethane, chloroform, N,N-dimethylformamide, toluene, ethyl acetate, water, and other solvents that do not participate in the reaction, or a mixture of these solvents. The reaction can be conducted between −50° C. and +50° C.

Protection of carboxylic acids is generally accomplished by esterification. This esterification is performed according to the method described above.

In the fluorination of a pyrrolidine ring, a 4-fluoro form can be obtained from a 4-hydroxy form, and a 4,4-difluoro form can be obtained from a 4-keto form, for example.

In scheme 1, an example of the monofluorination in step 1-3a is a method involving the use of diethylaminosulfur trifluoride or dimethylsulfur trifluoride, a mixture of 1,1,2,3,3,3-hexafluoro-1-(diethylamino)propane and 1,2,3,3,3-pentafluoro-1-(diethylamino)-2-propene, or the like. The use of a mixture of 1,1,2,3,3,3-hexafluoro-1-(diethylamino)propane and 1,2,3,3,3-pentafluoro-1-(diethylamino)-2-propene will give good results when cesium fluoride, sodium fluoride, or potassium fluoride is admixed in the reaction system. Examples of the solvent used in these reactions include tetrahydrofuran, dioxane, dichloromethane, chloroform, 1,2-dichloroethane, toluene, and other solvents that do not participate in the reaction, or a mixture of these solvents. The reaction is commenced between −78° C. and room temperature, and is then continued between room temperature and 50° C. An example of monofluorination is a method in which a hydroxyl group is converted into a leaving group, and then converted into a fluoro group. Examples of the conversion of a leaving group include chlorination, bromination, iodation, methanesulfonylation, and p-toluenesulfonylation.

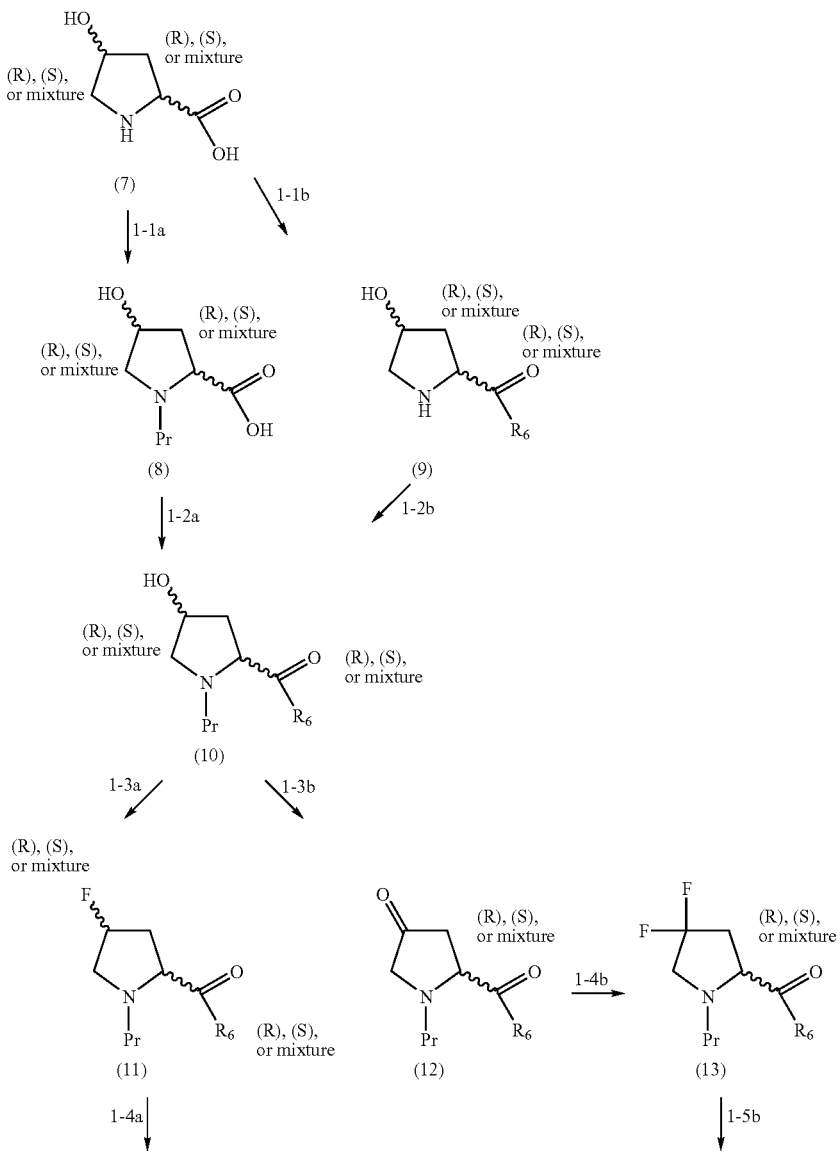

Scheme 1

-continued

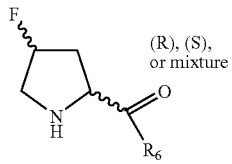

(14)

free form or salt

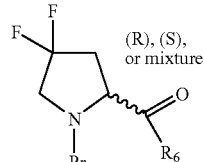

(15)

free form or salt (wherein $R_6$ is the same as defined in Formula 1, and Pr is the same as above.)

Examples of a chlorination reaction include the use of carbon tetrachloride and triphenylphosphine, the use of thionyl chloride or phosphorus oxychloride, and a method in which a leaving group is produced using tosyl chloride or the like, and then conversion is performed with lithium chloride or the like. Examples of the solvent used in these reactions include tetrahydrofuran, dioxane, dichloromethane, chloroform, N,N-dimethylformamide, and other solvents that do not participate in the reaction, or a mixture of these solvents. These reactions can be carried out between −50° C. and 100° C. An example of a bromination reaction is the use of carbon tetrachloride and triphenylphosphine. This reaction can be conducted in tetrahydrofuran, dioxane, dichloromethane, chloroform, N,N-dimethylformamide, and other solvents that do not participate in the reaction, or a mixture of these solvents, between −50° C. and 50° C. An example of an iodation reaction is the use of iodine, triphenylphosphine, and imidazole. This reaction can be conducted in tetrahydrofuran, dioxane, dichloromethane, chloroform, N,N-dimethylformamide, and other solvents that do not participate in the reaction, or a mixture of these solvents. These reactions are conducted at a temperature between −50° C. and 100° C.

Methanesulfonylation and p-toluenesulfonylation can be performed using methanesulfonyl chloride and p-toluenesulfonyl chloride, respectively, for example. A suitable base may be added here. Examples of bases that can be added include triethylamine, diisopropylethylamine, and other such organic amines, and potassium carbonate and other such inorganic bases. The reaction solvent here can be N,N-dimethylformamide, tetrahydrofuran, dioxane, dichloromethane, chloroform, 1,2-dichloroethane, and other solvents that do not participate in the reaction, or a mixture of these solvents, and the reaction can be conducted at a temperature between −50° C. and 50° C.

Examples of a method involving conversion into a leaving group and then conversion into a fluoro group include a method involving the reaction of tetrabutylammonium fluoride, cesium fluoride, potassium fluoride, sodium fluoride, or the like. These reactions can be conducted in tetrahydrofuran, dioxane, dichloromethane, chloroform, N,N-dimethylformamide, water, and other solvents that do not participate in the reaction, or a mixture of these solvents, and at a temperature between −50 and 100° C.

Difluorination is performed after a hydroxyl group has been oxidized into a ketone group.

This oxidation (step 1-3b) can be accomplished, for example, using pyridinium chlorochromate, pyridinium dichromate, or other chromic acid. Examples of the reaction solvent include dichloromethane and chloroform, and the reaction can be conducted at a temperature between 0° C. and close to the boiling point of the reaction solvent.

The reaction can also involve the use of a Dess-Martin reagent (1,1,1-triacetoxy-1,1-dihydro-1,2-benziodoxol-3-(1H)-one). Examples of the reaction solvent include dichloromethane and chloroform, and the reaction can be conducted at a temperature between 0° C. and 40° C.

As another example, the reaction can involve the use of IBX (1-hydroxy-1,2-benziodoxol-3-(1H)-one 1-oxide). Dimethyl sulfoxide can be used as the reaction solvent, and the reaction solution can be further diluted with a solvent that does not participate in the reaction, such as tetrahydrofuran, dichloromethane, or chloroform. The reaction temperature can be from 0° C. to 40° C.

Other than the above, there are no particular restrictions on this oxidation reaction, as long as it is a method that allows an alcohol to be oxidized into a ketone. Examples include a reaction involving dimethyl sulfoxide and an activator (such as oxalyl chloride, N-chlorosuccinimide, or dicyclohexylcarbodiimide), or an oxidation method involving the use of tetra-n-propylammonium perruthenate(VII) and N-methylmorpholine oxide. A comprehensive overview of this oxidation reaction can be found in Comprehensive Organic Transformation, by Richard C. Larock, Wiley-VHC, 1999, 604.

Also, in Scheme 1, examples of the difluorination in step 1-4b include the use of dimethylsulfur trifluoride, [bis(2-methoxyethyl)amino]sulfur trifluoride, or another such fluorination agent. These reactions can be conducted in tetrahydrofuran, dioxane, dichloromethane, chloroform, 1,2-dichloroethane, toluene and mixtures of these solvents. The reaction is commenced between −78° C. and room temperature, and is then continued between room temperature and close to the boiling point of the solvent.

A compound 14 or 15, or a salt thereof, can be manufactured by removing the protective group from the nitrogen atom by a standard method (steps 1-4a and 1-5b).

For example, when the protection is achieved with a group that is removed with a tert-butyloxycarbonyl group or another such acid, the protective group can be removed using hydrochloric acid, sulfuric acid, trifluoroacetic acid, p-toluenesulfonic acid, methanesulfonic acid, or another such acid. The deprotection here can be performed by diluting or dissolving the acid with an organic solvent, and the reaction can be conducted at temperature between −50° C. and 50° C. Examples of the organic solvent include ethanol, methanol, tetrahydrofuran, N,N-dimethylformamide, dichloromethane, chloroform, 1,2-dichloroethane, and mixtures of these solvents.

Further, when the protection is achieved with a group that is removed by hydrogenolysis of a benzyloxycarbonyl group, for example, the protective group can be removed by a hydrogenolysis reaction using a metal catalyst such as palladium. The solvent can be ethanol, methanol, tetrahydrofuran, ethyl acetate, and other such solvents that do not participate in the reaction, and mixtures of these solvents. The reaction can be conducted between 0° C. and 100° C. Hydrogen gas can also be used for this reaction, and a formic acid/ammonium formate combination can also be used.

Further, when the protection is achieved with a group that is removed with a group such as a fluorenyloxycarbonyl group that is removed with a base, deprotection can be accomplished using a base such as diethylamine, piperidine, ammonia, sodium hydroxide, or potassium hydroxide. These bases can be used alone, or after being diluted, dissolved, or suspended with a solvent. Solvents that can be used here include water, ethanol, methanol, tetrahydrofuran, N,N-dimethylformamide, dichloromethane, chloroform, 1,2-dichloroethane, and so forth, as well as mixtures of these solvents. The reaction can be conducted at a temperature between 0° C. and close to the boiling point of the solvent.

Further, when the protection is achieved with a group that is removed with a metal catalyst such as allyloxycarbonyl, deprotection can be accomplished by using tetrakis(triphenylphosphine)palladium or the like as a catalyst or reagent. The reaction here can be conducted in dichloromethane, chloroform, tetrahydrofuran, or another such solvent that will not participate in the reaction, and at a temperature between 0° C. and close to the boiling point of the solvent.

be obtained when sodium fluoride, potassium fluoride, or cesium fluoride is present in the reaction system. The reaction is conducted in tetrahydrofuran, dioxane, dichloromethane, chloroform, 1,2-dichloroethane, toluene, or another solvent that will not participate in the reaction, or in a mixture of these solvents, and is commenced between −78° C. and room temperature, and then continued between room temperature and close to the boiling point of the solvent.

In this case, the steric configuration of the 4-position of compounds 16 and 18, which are the synthesis raw materials, may be either the (R) configuration or the (S) configuration, and a 4-fluoride compound 20 of (4R) configuration can be obtained in either case. The compound 20 thus obtained is deprotected by a standard method to obtain a compound 21 or a salt thereof.

Of the compounds expressed by Formula 4, when $R_5$ is a hydrogen atom and $R_6$ is an alkoxy group, a dimethylamino group, or an ethylamino group, the compound can be manufactured by the synthesis route shown in Scheme 3. The methyl or ethyl(2S,4R)-N-protected-4-hydroxy-2-pyrrolidinecarboxylate expressed by compound 22 is used as the syn-

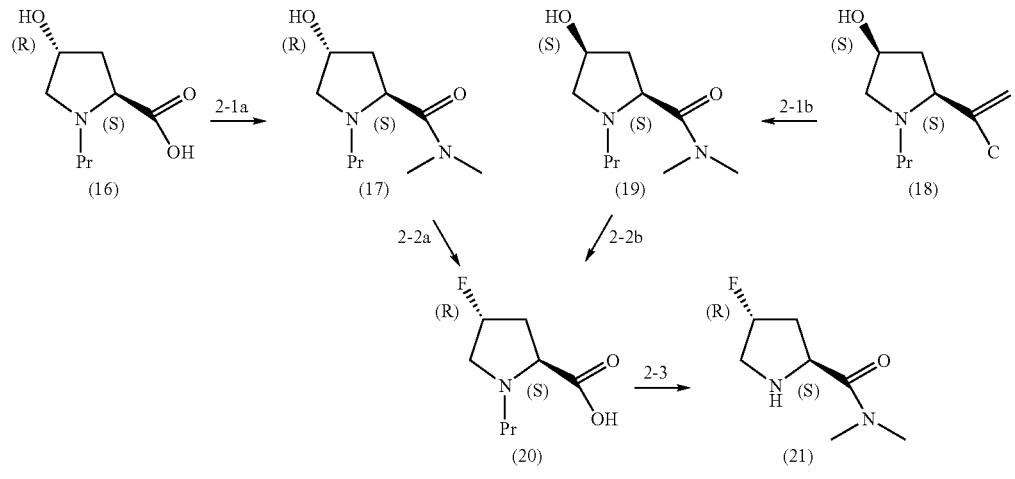

(wherein, Pr is the same as above)

(4R)- or (4S)-4-hydroxy-L-proline or (4R)- or (4S)-4-hydroxy-D-proline can be purchased commercially.

Of the compounds defined by Formula 4, (4R)-4-fluoro-N,N-dimethyl-L-prolinamide (21) can be manufactured by the synthesis route shown in Scheme 2.

Compound 16 or 18, that is, (4R)-N-protected-4-hydroxy-L-proline (16) or (4S)-N-protected-4-hydroxy-L-proline (18), is used as the synthesis raw material, N,N-dimethylamidation is performed according to a standard method for forming amide bonds in step 2-1a and 2-1b, and then fluorination is performed in steps 2-2a and 2-2b using a fluorination agent, and particularly a mixture of 1,1,2,3,3,3-hexafluoro-1-(diethylamino)propane and 1,2,3,3,3-pentafluoro-1-(diethylamino)-2-propene. In this fluorination, good results will thesis raw material, and fluorine of (4S) configuration is introduced by standard fluorination (step 3-1) of a hydroxyl group. The compound 23 thus obtained can be deprotected by a standard method (step 3-5) to obtain a methyl or ethyl(4R)-4-fluoro-L-prolinate form 27 or a salt thereof. Meanwhile, compound 23 can have its ester hydrolyzed (step 3-2) by a standard method to manufacture a carboxylic acid form 24. The carboxylic acid form 24 thus obtained can be amidated (step 3-3) according to a standard method for forming peptide bonds, and then the protective group of the nitrogen atom can be removed by a standard method (step 3-4) to manufacture a (4S)-4-fluoro-N,N-dimethyl or —N-ethyl-L-prolinamide form 26 or a salt thereof.

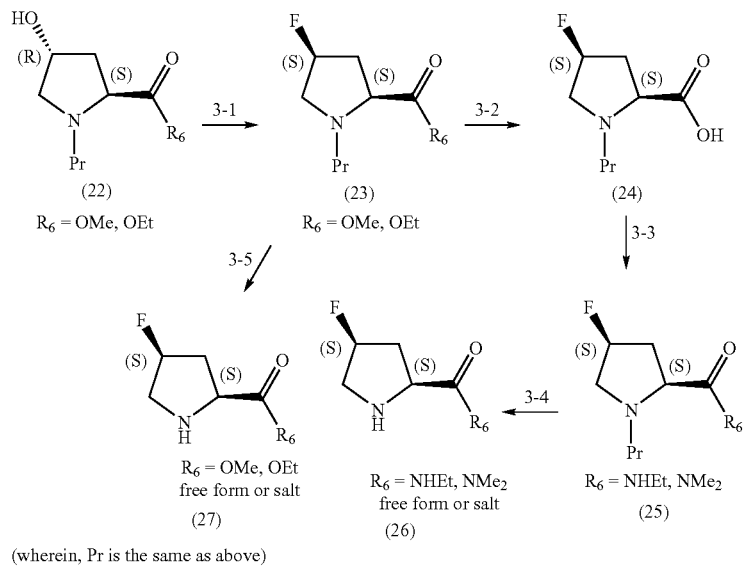

Scheme 3

(wherein, Pr is the same as above)

The hydrolysis of the ester can be accomplished, for example, by using a base such as potassium carbonate or another metal carbonate, or sodium hydroxide or another metal hydroxide. The reaction solvent here can be methanol, ethanol, or another alcohol, tetrahydrofuran, dioxane, N,N-dimethylformamide, water, or the like, or a mixture of these solvents. The reaction can be conducted at a temperature between −20° C. and close to the boiling point of the reaction solvent.

When the protection is achieved with a group that is removed with the acid of another ester, such as a tert-butyl ester, the protective group can be removed using hydrochloric acid, sulfuric acid, trifluoroacetic acid, p-toluenesulfonic acid, methanesulfonic acid, or another such acid. The deprotection here can be performed by diluting or dissolving the acid with an organic solvent or water, and the reaction can be conducted at temperature between −50° C. and +50° C. Examples of the organic solvent include ethanol, methanol, tetrahydrofuran, N,N-dimethylformamide, dichloromethane, chloroform, 1,2-dichloroethane, and mixtures of these solvents.

Further, when the protection is achieved with a group that is removed by hydrogenolysis of a benzyl ester or the like, the protective group can be removed by a hydrogenolysis reaction using a metal catalyst such as palladium. The solvent can be ethanol, methanol, tetrahydrofuran, ethyl acetate, and other such solvents that do not participate in the reaction, and mixtures of these solvents. The reaction can be conducted between 0° C. and 100° C. Hydrogen gas can also be used for this reaction, and a formic acid/ammonium formate combination can also be used.

Further, when the protection is achieved with a group that is removed with a metal catalyst such as an allyl ester, deprotection can be accomplished by using tetrakis(triphenylphosphine)palladium or the like as a catalyst or reagent. The reaction here can be conducted in dichloromethane, chloroform, tetrahydrofuran, or another such solvent that will not participate in the reaction, and at a temperature between 0° C. and close to the boiling point of the solvent.

Of the compounds expressed by Formula 4, when $R_5$ is a fluorine atom and $R_6$ is an dimethylamino group or an ethylamino group, the compound can be manufactured by the synthesis route shown in Scheme 4. 4,4-difluoro-N-protected-2-pyrrolidine carboxylate, which is one of the above-mentioned compounds 13 in Scheme 1, can be used as the synthesis raw material, and a carboxylic acid form 28 can be obtained by hydrolysis in step 4-1. The carboxylic acid form 28 thus obtained is subjected to amide bond formation by a standard method to obtain compound 29 (step 4-2). The protective group of the nitrogen atom is removed by a standard method (step 4-3) to obtain compound 30 or a salt thereof.

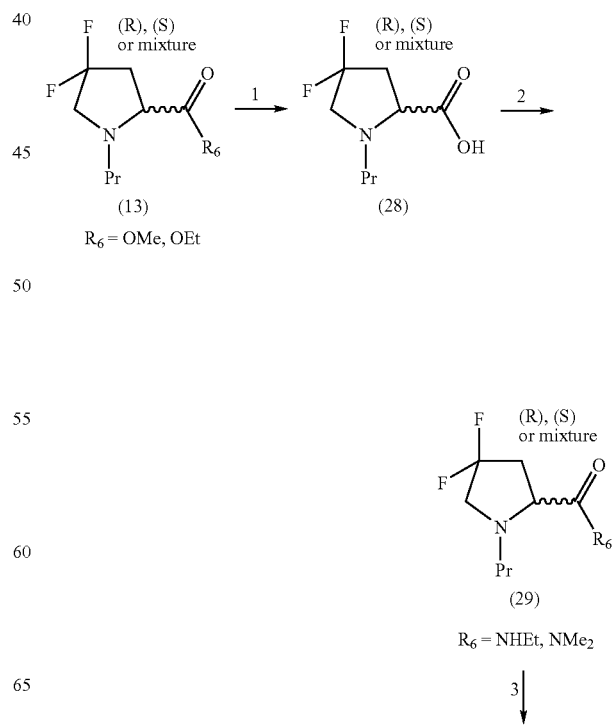

Scheme 4

-continued

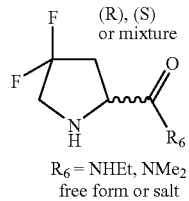

$R_6$ = NHEt, NMe$_2$
free form or salt (wherein Pr is the same as above.)

The present invention will now be described in more specific terms by giving examples and test examples. In these examples, "silica gel 60" and "silica gel 60N" refer to silica gels marketed by Kanto Chemical. "Chromatorex NH" refers to a silica gel marketed by Fuji Silysia. The progress of the reaction was tracked by thin layer chromatography (TLC) using a 0.25 mm silica gel 60F$_{254}$ plate (made by Merck). The coloring of the TLC plate was observed using UV (254 nm) or a 20% sodium phosphomolybdate/ethanol solution.

The $^1$H-NMR spectrum uses tetramethylsilane as an internal reference, and the chemical shift was given in ppm.

EXAMPLE 1

Synthesis of (4R)-1-[5-chloro-1-[2,4-dimethoxyphenyl)sulfonyl]-3-(2-methoxyphenyl)-2-oxo-2,3-dihydro-1H-indol-3-yl]-4-fluoro-N,N-dimethyl-L-prolinamide (levorotatory isomer)

Step 1-1a: Synthesis of tert-butyl(2S,4R)-2-[(dimethylamino)carbonyl]-4-hydroxypyrrolidine-1-carboxylate 24.9 g of 1-hydroxybenzotriazole monohydrate and 24.9 g of 1-ethyl-3-(3-dimethylaminopropyl)carbodiimide hydrochloride were added under ice cooling to a 250 mL tetrahydrofuran solution of 25.1 g of (4R)-1-(tert-butoxycarbonyl)-4-hydroxy-L-proline and stirred for 15 minutes. 10.7 g of a 50% dimethylamine aqueous solution was added dropwise over a period of 10 minutes to the reaction mixture, and the reaction mixture was stirred for 15 hours at room temperature. The solvent was distilled off under reduced pressure, after which 100 mL of a saturated sodium hydrogencarbonate aqueous solution was added and extraction was performed with chloroform (50 mL×2). The extract was dried with anhydrous sodium sulfate, the drying agent was filtered off, and the reaction mixture was concentrated under reduced pressure. The residue was purified by column chromatography (silica gel 60N, mobile phase: chloroform/methanol=20/1 to 9/1; v/v) to obtain 26.2 g of the titled compound (colorless solid).

MS (ESI pos.) m/z: 281([M+Na]$^+$) $^1$H-NMR (300 MHz, CDCl$_3$) δ (ppm); 1.40 & 1.45 (each-s, 9H), 1.95-2.36 (m, 3H), 2.97 & 2.98 (each-s, 3H), 3.08 & 3.13 (each-s, 3H), 3.41-3.62 (m, 1H), 3.63-3.76 (m, 1H), 4.46-4.60 (m, 1H), 4.69-4.87 (m, 1H)

Step 1-2a: Synthesis of tert-butyl(2S,4R)-2-[(dimethylamino)carbonyl]-4-fluoropyrrolidine-1-carboxylate 26.6 g of a mixture (approximately 3:1) of 1,1,2,3,3,3-hexafluoro-1-(diethylamino)propane and 1,2,3,3,3-pentafluoro-1-(diethylamino)-2-propene was added dropwise over a period of 10 minutes under ice cooling to a suspension of 25.7 g of the compound obtained in step 1-1a and 5.00 g of sodium fluoride in 260 mL of dichloromethane, after which the reaction mixture was stirred for 16 hours at room temperature. 100 mL of a 5% potassium carbonate aqueous solution was added under ice cooling to the reaction solution, and the reaction mixture was stirred for 30 minutes at the same temperature. After liquid separation, the aqueous layer thus obtained was extracted with chloroform, and the combined organic layer was washed with 50 mL of saturated brine and dried with magnesium sulfate, after which the drying agent was filtered off and the solvent was distilled off under reduced pressure. The residue thus obtained was subjected to column chromatography (silica gel 60, mobile phase: ethyl acetate/n-hexane=1/1 to 10/0; v/v) to obtain 12.2 g of the titled compound (pale yellow solid).

MS (ESI pos.) m/z: 283([M+Na]$^+$) $^1$H-NMR (300 MHz, CDCl$_3$) δ (ppm); 1.42 & 1.46 (each-s, 9H), 2.00-2.26 (m, 1H), 2.36-2.55 (m, 1H), 2.98 & 2.99 (each-s, 3H), 3.10 & 3.16 (each-s, 3H), 3.58-3.99 (m, 2H), 4.71-4.92 (m, 1H), 5.12-5.38 (m, 1H)

Step 1-1b: Synthesis of tert-butyl(2S,4S)-2-[(dimethylamino)carbonyl]-4-hydroxypyrrolidine-1-carboxylate 9.95 g of 1-ethyl-3-(3-dimethylaminopropyl)carbodiimide hydrochloride was added under ice cooling to a 100 mL tetrahydrofuran solution of 10.0 g of (4S)-1-(tert-butoxycarbonyl)-4-hydroxy-L-proline and 8.77 g of 1-hydroxybenzotriazole monohydrate, and the reaction mixture was stirred for 30 minutes at the same temperature. 15.6 g of a 50% dimethylamine aqueous solution was than added to the reaction solution, after which the reaction mixture was stirred for 1 hour at room temperature. 100 mL of chloroform and 50 mL of a 5% potassium carbonate aqueous solution were added to the reaction solution, liquid separation was performed, the aqueous layer was extracted with chloroform (30 mL×2), and the combined organic layer was washed with 30 mL of saturated brine and dried with magnesium sulfate, after which the drying agent was filtered off and the solvent was distilled off under reduced pressure. The residue thus obtained was subjected to column chromatography (silica gel 60, mobile phase: ethyl acetate/n-hexane=1/1 to 10/0; v/v) to obtain 8.66 g of the titled compound (colorless solid).

MS (ESI pos.) m/z: 281([M+Na]$^+$) $^1$H-NMR (300 MHz, CDCl$_3$) δ (ppm); 1.42 & 1.45 (each-s, 9H), 1.91-1.99 (m, 1H), 2.17-2.35 (m, 1H), 3.02 & 3.03 (each-s, 3H), 3.16 & 3.27 (each-s, 3H), 3.48-3.56 (m, 1H), 3.64-3.86 (m, 1H), 4.26-4.37 (m, 1H), 4.66-4.84 (m, 1H), 5.28-5.83 (m, 1H)

Step 1-2b: Synthesis of tert-butyl(2S,4R)-2-[(dimethylamino)carbonyl]-4-fluoropyrrolidine-1-carboxylate 8.85 g of a mixture (approximately 3:1) of 1,1,2,3,3,3-hexafluoro-1-(diethylamino)propane and 1,2,3,3,3-pentafluoro-1-(diethylamino)-2-propene was added dropwise over a period of 2 minutes under ice cooling to a suspension of 8.54 g of the compound obtained in step 1-1b and 1.67 g of sodium fluoride in 90 mL of dichloromethane, after which the reaction mixture was stirred for 15 hours at room temperature. 200 mL of a saturated sodium hydrogencarbonate aqueous solution was added dropwise to the reaction solution over a period of 3 minutes, and the reaction mixture was stirred for 1 hour. After liquid separation, the aqueous layer was extracted with chloroform (30 mL×2), and the combined organic layer was washed with 50 mL of saturated brine and dried with magnesium sulfate, after which the drying agent was filtered off and the reaction mixture was concentrated under reduced pressure. The residue thus obtained was subjected to column chromatography (silica gel 60, mobile phase: ethyl acetate/n-hexane=1/1 to 10/0; v/v) to obtain 7.54 g of the titled compound (pale yellow solid).

Step 1-3: Synthesis of (4R)-4-fluoro-N,N-dimethyl-L-prolinamide trifluoroacetate 10.5 mL of trifluoroacetic acid was added under ice cooling to a 25 mL chloroform solution of 3.50 g of the compound obtained in step 1-2b, after which the reaction mixture was stirred for 3 hours at room temperature. The solvent was then distilled off under reduced pressure, which gave 7.27 g of residue (yellow oily substance). This compound was used in the following reaction without being purified.

MS (ESI pos.) m/z: 161 ([M+H]$^+$) $^1$H-NMR (300 MHz, DMSO-d$_6$) δ (ppm); 1.97-2.21 (m, 1H), 2.68-2.87 (m, 1H), 2.92 (s, 3H), 3.02 (s, 3H), 3.37-3.62 (m, 2H), 4.72-4.85 (m, 1H), 5.36-5.60 (m, 1H), 8.83 (brs, 1H), 9.99 (brs, 1H)

Step 1-4: Synthesis of (4R)-1-[5-chloro-3-(2-methoxyphenyl)-2-oxo-2,3-dihydro-1H-indol-3-yl]-4-fluoro-N,N-dimethyl-L-prolinamide 7.47 g of triethylamine was added under ice cooling to a suspension of 3.78 g of 3,5-dichloro-3-(2-methoxyphenyl)-1,3-dihydro-2H-indol-2-one and the compound (unpurified) obtained in step 1-3 in 40 mL of chloroform under a nitrogen atmosphere, after which the reaction mixture was stirred for 13 hours at room temperature. 40 mL of a 5% potassium carbonate aqueous solution was poured into the reaction solution under stirring, and extraction was performed with chloroform (30 mL×2). The combined organic layer was washed with 50 mL of saturated brine and dried with magnesium sulfate, then the drying agent was filtered off and the solvent was distilled off under reduced pressure to obtain 6.43 g of a brown solid. This was separated and purified by column chromatography (silica gel 60, mobile phase: ethyl acetate/aceton=4/1; v/v) to obtain two kinds of diastereoisomer of the titled compound in amounts of 2.06 g (isomer A: colorless powder) and 2.74 g (isomer B: colorless powder).

Isomer A: [α]$_D^{29}$=+129° (c=0.578, chloroform) MS (ESI pos.) m/z: 454([M+Na]$^+$), (ESI neg.) m/z: 430([M−H]$^-$) $^1$H-NMR (300 MHz, DMSO-d$_6$) δ (ppm); 1.65-1.94 (m, 1H), 2.17-2.35 (m, 1H), 2.42-2.85 (m, 6H), 3.22-3.56 (m, 1H), 3.47 (s, 3H), 3.75-3.97 (m, 2H), 5.05-5.31 (m, 1H), 6.50 (s, 1H), 6.82 (d, J=8.1 Hz, 1H), 6.92 (d, J=8.2 Hz, 1H), 7.07-7.21 (m, 2H), 7.29 (t, J=7.5 Hz, 1H), 8.05 (d, J=7.5 Hz, 1H), 10.52 (s, 1H)

Isomer B: [α]$_D^{28}$=−188° (c=0.219, chloroform) MS (ESI pos.) m/z: 454([M+Na]$^+$), (ESI neg.) m/z: 430([M−H]$^-$) $^1$H-NMR (300 MHz, DMSO-d$_6$) δ (ppm); 1.79-1.99 (m, 1H), 2.23-2.54 (m, 7H), 2.88-3.06 (m, 1H), 3.42-3.72 (m, 1H), 3.46 (s, 3H), 4.58-4.70 (m, 1H), 5.18-5.43 (m, 1H), 6.74 (d, J=8.2 Hz, 1H), 6.83 (d, J=2.2 Hz, 1H), 6.91 (dd, J=8.2, 1.09 Hz, 1H), 6.97-7.05 (m, 1H), 7.15-7.20 (m, 1H), 7.23-7.31 (m, 1H), 7.86 (dd, J=7.7, 1.5 Hz, 1H), 10.33 (s, 1H)

Step 1-5: Synthesis of (4R)-1-[5-chloro-1-[(2,4-dimethoxyphenyl)sulfonyl]-3-(2-methoxyphenyl)-2-oxo-2,3-dihydro-1H-indol-3-yl]-4-fluoro-N,N-dimethyl-L-prolinamide (levorotatory isomer)

2.00 g of isomer B obtained in step 1-4 was added under ice cooling to a 20 mL dimethylformamide solution of 0.215 g of sodium hydride under a nitrogen atmosphere, and the reaction mixture was stirred for 40 minutes. 5 mL dimethylformamide solution of 1.27 g of 2,4-dimethoxybenzenesulfonyl chloride was added dropwise to the reaction mixture. The reaction mixture was stirred for 35 minutes at the same temperature, after which 50 mL of chloroform and 50 mL of a 5% potassium carbonate aqueous solution were added, and the reaction mixture was stirred for another 1 hour at room temperature. After liquid separation, the aqueous layer was extracted with chloroform (15 mL×2), and the combined organic layer was dried with magnesium sulfate, after which the drying agent was filtered off and the solvent was distilled off under reduced pressure to obtain 3.74 g of residue (amorphous, pale yellow). The residue thus obtained was subjected to column chromatography (silica gel 60, mobile phase: ethyl acetate/n-hexane=1/1; v/v) to obtain 2.30 g of the titled compound (amorphous, colorless amorphous).

[α]$_D^{28}$=−199° (c=0.590, chloroform) MS (ESI pos.) m/z: 654([M+Na]$^+$) $^1$H-NMR (300 MHz, CDCl$_3$) δ (ppm); 1.87-3.94 (m, 4H), 2.33 (s, 3H), 2.76 (s, 3H), 3.56-3.79 (m, 6H), 3.86 (s, 3H), 4.76-5.00 (m, 1H), 5.15-5.43 (m, 1H), 6.43 (d, J=2.2 Hz, 1H), 6.58-6.64 (m, 1H), 6.78 (d, J=8.4 Hz, 1H), 6.92-7.00 (m, 1H), 7.07 (brs, 1H), 7.20-7.31 (m, 2H), 7.72-7.81 (m, 1H), 7.92 (d, J=8.7 Hz, 1H), 8.16 (d, J=8.9 Hz, 1H)

EXAMPLE 2

Synthesis of (4S)-1-[5-chloro-1-[(2,4-dimethoxyphenyl)sulfonyl]-3-(2-methoxyphenyl)-2-oxo-2,3-dihydro-1H-indol-3-yl]-4-fluoro-N,N-dimethyl-L-prolinamide (levorotatory isomer)

Step 2-1: Synthesis of 1-tert-butyl-2-methyl(2S,4S)-4-fluoropyrrolidine-1,2-dicarboxylate 32.8 g of a mixture (approximately 3:1) of 1,1,2,3,3,3-hexafluoro-1-(diethylamino)propane and 1,2,3,3,3-pentafluoro-1-(diethylamino)-2-propene was added dropwise over a period of 10 minutes under ice cooling to a suspension of 30.0 g of the 1-tert-butyl-2-methyl(2S,4R)-4-hydroxypyrrolidine-1,2-dicarboxylate and 6.16 g of sodium fluoride in 180 mL of dichloromethane, after which the reaction mixture was stirred for 15 hours at room temperature. The reaction solution was poured into 200 mL of a saturated sodium hydrogencarbonate aqueous solution under stirring and ice cooling, and the reaction mixture was stirred for 15 minutes. After the reaction mixture was allowed to stand and undergo liquid separation, the organic layer thus obtained distilled under reduced pressure to remove the solvent and obtain a residue. The aqueous layer was extracted with 60 mL of ethyl acetate and combined with the above-mentioned residue. The organic layer was washed with 40 mL of 10% potassium hydrogensulfate aqueous solution and saturated brine and dried with magnesium sulfate, after which the drying agent was filtered off and the solvent was distilled off under reduced pressure. The residue thus obtained was distilled under reduced pressure (b.p. 81 to 83° C./11 hPa) to remove the unnecessary components and obtain 36.8 g of residue (yellow oily substance). The residue thus obtained was subjected to column chromatography (silica gel 60, mobile phase: ethyl acetate/n-hexane=1/1; v/v) to obtain 34.6 g of the titled compound (colorless oily substance).

MS (ESI pos.) m/z: 270([M+Na]$^+$) $^1$H-NMR (200 MHz, DMSO-d$_6$) δ (ppm); 1.35 & 1.41 (each-s, 9H), 2.13-2.76 (m, 2H), 3.19-3.74 (m, 5H), 4.33-4.45 (m, 1H), 5.13-5.39 (m, 1H)

Step 2-2: Synthesis of (4S)-1-(tert-butoxycarbonyl)-4-fluoro-L-proline

A 181 mL methanol solution of 30.2 g of the compound obtained in step 2-1 was added dropwise over a period of 60 minutes under stirring to 86 mL of a 2 mol/L sodium hydroxide aqueous solution, after which the reaction mixture was stirred for 16 hours at room temperature. The methanol was distilled off under reduced pressure, 136 mL of toluene was added and stirred, and then the aqueous layer was separated and stirred under ice cooling. 122 mL of 2 mol/L hydrochloric acid was added dropwise over a period of 40 minutes, after which extraction was performed with ethyl acetate (230 mL×2), the combined organic layer was washed with 128 mL of saturated brine and dried with sodium sulfate, then the drying agent was filtered off and the solvent was distilled off under reduced pressure to obtain 25.1 g of a colorless solid. 91 mL of diisopropyl ether was added and stirred for 2 hours at room temperature, after which the crystals were filtered off to obtain 20.2 g of the titled compound (colorless solid). The filtrate was concentrated under reduced pressure, and 9 mL of diisopropyl ether was added and stirred for 2 hours at room temperature, after which the crystals were filtered off to obtain 0.54 g of the titled compound (colorless solid).

MS (ESI neg.) m/z: 232([M−H]$^-$) $^1$H-NMR (300 MHz, DMSO-d$_6$) δ (ppm); 1.36 & 1.41 (each-s, 9H) 2.13-2.63 (m, 2H), 3.29-3.71 (m, 2H), 4.28 (t, J=9.1 Hz, 1H), 5.13-5.39 (m, 1H) 12.55 (brs, 1H)

Step 2-3: Synthesis of tert-butyl(2S,4S)-2-[(dimethylamino)carbonyl]-4-fluoropyrrolidine-1-carboxylate 19.6 g of 1-ethyl-3-(3-dimethylaminopropyl)carbodiimide hydrochloride was added under ice cooling to a 200 mL tetrahydrofuran solution of 19.9 g of the compound obtained in step 2-2 and 17.3 g of 1-hydroxybenzotriazole monohydrate, and the reaction mixture was stirred for 30 minutes at the same temperature. After this, 9.24 g of a 50% dimethylamine aqueous solution was added to the reaction solution, and the reaction mixture was stirred for 1 hour while the temperature was raised to room temperature. 150 mL of solvent was distilled off under reduced pressure, and to the residue thus obtained was added 100 mL of chloroform and 100 mL of a 10% potassium carbonate aqueous solution. After liquid separation, the aqueous layer was extracted with chloroform, and the combined organic layer was washed with saturated brine and then dried with magnesium sulfate, after which the drying agent was filtered off and the solvent was distilled off under reduced pressure. The residue thus obtained was subjected to column chromatography (silica gel 60, mobile phase: ethyl acetate/n-hexane=1/1 to 10/0; v/v) to obtain 20.5 g of the titled compound (colorless solid).

MS (ESI pos.) m/z: 283([M+Na]$^+$) $^1$H-NMR (300 MHz, DMSO-d$_6$) δ (ppm); 1.31 & 1.39 (each-s, 9H), 1.93-2.10 (m, 1H), 2.40-2.71 (m, 1H), 2.81 & 2.83 (each-s, 3H), 2.97 (s, 3H), 3.42-3.79 (m, 2H), 4.59-4.71 (m, 1H), 5.10-5.37 (m, 1H)

Step 2-4: Synthesis of (4S)-4-fluoro-N,N-dimethyl-L-prolinamide trifluoroacetate 18 mL of trifluoroacetic acid was added under ice cooling to a 60 mL chloroform solution of 5.98 g of the compound obtained in step 2-3, and the reaction mixture was stirred for 2 hours at the same temperature. After this, the solvent was distilled off under reduced pressure to obtain 12.1 g of residue (colorless oily substance). This compound was used in the following reaction without being purified.

MS (ESI pos.) m/z: 161([M+H]$^+$), 183([M+Na]$^+$) $^1$H-NMR (300 MHz, DMSO-d$_6$) δ (ppm); 2.12-2.30 (m, 1H), 2.68-3.02 (m, 1H), 2.93 (s, 3H), 2.98 (s, 3H), 3.27-3.53 (m, 1H), 3.59-3.77 (m, 1H), 4.67-4.81 (m, 1H), 5.32-5.55 (m, 1H), 8.83 (brs, 1H), 10.19 (brs, 1H)

Step 2-5: Synthesis of (4S)-1-[5-chloro-3-(2-methoxyphenyl)-2-oxo-2,3-dihydro-1H-indol-3-yl]-4-fluoro-N,N-dimethyl-L-prolinamide 12.7 g of triethylamine was added under ice cooling to a chloroform solution of 6.44 g of 3,5-dichloro-3-(2-methoxyphenyl)-1,3-dihydro-2H-indol-2-one and the compound obtained in step 2-4 (23.0 mmol, crude product), after which the reaction mixture was stirred for 24.5 hours at room temperature. The reaction solution was poured into 200 mL of a 5% potassium carbonate aqueous solution under stirring, and extraction was performed with chloroform. The combined organic layer was washed with saturated brine and dried with magnesium sulfate, the drying agent was filtered off, and the solvent was distilled off under reduced pressure to obtain 12.2 g of residue (Mars brown solid). The residue thus obtained was suspended in 60 mL of a mixed solvent of chloroform and methanol (1:1; v/v), and the insolubles were filtered off to obtain 3.64 g of the titled compound (isomer B; colorless powder). The filtrate was concentrated, and the residue thus obtained was purified by column chromatography (first time: silica gel 60, mobile phase: ethyl acetate/n-hexane=1/3 to 10/0, v/v; second time: Chromatorex NH, mobile phase: chloroform/methanol=13/1, v/v) to obtain 340 mg of the titled compound (isomer A, colorless powder).

Isomer A: [α]$_D^{29}$=+32° (c=0.224, methanol) MS (ESI pos.) m/z: 454([M+Na]$^+$), (ESI neg.) m/z: 430([M−H]$^-$) $^1$H-NMR (300 MHz, CDCl$_3$) δ (ppm); 2.03-2.24 (m, 1H), 2.60-2.95 (m, 1H), 2.70 (s, 3H), 3.23 (s, 3H), 3.42-3.84 (m, 3H), 3.58 (s, 3H), 5.01-5.28 (m, 1H), 6.75 (d, J=8.2 Hz, 1H), 6.79-6.91 (m, 2H), 7.07-7.20 (m, 2H), 7.23-7.33 (m, 1H), 8.00 (d, J=7.5 Hz, 1H), 9.54 (brs, 1H)

Isomer B: [α]$_D^{28}$=−198° (c=0.733, N,N-dimethylformamide) MS (ESI pos.) m/z: 454([M+Na]$^+$), (ESI neg.) m/z: 430([M−H]$^-$) $^1$H-NMR (300 MHz, DMSO-d$_6$) δ (ppm); 1.67-1.84 (m, 1H), 2.20-3.55 (m, 3H), 2.56 (s, 3H), 2.57 (s, 3H), 3.48 (s, 3H), 4.49-4.58 (m, 1H), 5.12-5.40 (m, 1H), 6.77 (d, J=8.2 Hz, 1H), 6.81 (d, J=2.0 Hz, 1H), 6.93 (dd, J=8.2, 1.1 Hz, 1H), 6.97-7.05 (m, 1H), 7.18 (dd, J=8.3, 2.3 Hz, 1H), 7.23-7.31 (m, 1H), 7.60-7.70 (m, 1H), 10.44 (brs, 1H)

Step 2-6: Synthesis of (4S)-1-[5-chloro-1-[(2,4-dimethoxyphenyl)sulfonyl]-3-(2-methoxyphenyl)-2-oxo-2,3-dihydro-1H-indol-3-yl]-4-fluoro-N,N-dimethyl-L-prolinamide (levorotatory isomer)

1.50 g of the compound obtained in step 2-5 (isomer B) was used as the starting raw material to obtain 1.70 g of the titled compound (colorless, amorphous) by the same method as in step 1-5.

$[\alpha]_D^{26}$=−222° (c=0.654, chloroform) MS (ESI pos.) m/z: 654([M+Na]$^+$) $^1$H-NMR (300 MHz, CDCl$_3$) δ (ppm); 1.74-1.92 (m, 1H), 1.97-2.23 (m, 1H), 2.45 (s, 3H), 2.49-2.70 (m, 1H), 2.85 (s, 3H), 3.17-3.34 (m, 1H), 3.62 (s, 3H), 3.67 (s, 3H), 3.88 (s, 3H), 4.30-4.59 (m, 1H), 4.69 (dd, J=9.6, 3.7 Hz, 1H), 6.46 (d, J=2.2 Hz, 1H), 6.63 (dd, J=8.9, 2.3 Hz, 1H), 6.77 (dd, J=8.2, 0.9 Hz, 1H), 6.94-7.03 (m, 1H), 7.15-7.32 (m, 3H), 7.88-7.94 (m, 2H), 8.15 (d, J=8.9 Hz, 1H)

EXAMPLE 3

Synthesis of 1-[5-chloro-1-[(2,4-dimethoxyphenyl)sulfonyl]-3-(2-methoxyphenyl)-2-oxo-2,3-dihydro-1H-indol-3-yl]-4,4-difluoro-N,N-dimethyl-L-prolinamide (levorotatory isomer)

Step 3-1: Synthesis of 1-tert-butyl 2-methyl(2S)-4-oxopyrrolidine-1,2-dicarboxylate 150 g of 1-tert-butyl 2-methyl(2S,4R)-4-hydroxypyrrolidine-1,2-dicarboxylate, 264 g of pyridinium chlorochromate, and 75 g of celite were stirred in 2 L of chloroform at room temperature. During this stirring, another 100 g of pyridinium chlorochromate was added, and the reaction mixture was stirred for a total of 7 days. The reaction solution was filtered through celite (washed with 500 mL of chloroform), and the filtrate was concentrated under reduced pressure to obtain 197 g of black oil. The residue thus obtained was purified by column chromatography (silica gel 60, mobile phase: ethyl acetate/n-hexane=2/1; v/v) to obtain 119 g of the titled compound (yellow oily substance).

MS (ESI neg.) m/z: 242([M−H]$^−$) $^1$H-NMR (300 MHz, CDCl$_3$) δ (ppm); 1.30-1.50 (m, 9H), 2.59 (dd, J=18.9, 2.6 Hz, 1H), 2.84-3.05 (m, 1H), 3.77 (s, 3H), 3.86-4.03 (m, 2H), 4.67-4.92 (m, 1H)

Step 3-2: Synthesis of 1-tert-butyl 2-methyl(2S)-4,4-difluoropyrrolidine-1,2-dicarboxylate 36.0 g of [bis(2-methoxyethyl)amino]sulfur trifluoride was added dropwise over a period of 5 minutes under ice cooling to a 150 mL chloroform solution of 18.0 g of the compound obtained in step 3-1, after which the reaction mixture was stirred for 19 hours at room temperature. The reaction solution was added dropwise over a period of 10 minutes under ice cooling to 300 mL of a saturated potassium carbonate aqueous solution. After liquid separation, the aqueous layer was extracted with chloroform (30 mL×2), and the combined organic layer was washed with 30 mL of saturated brine and dried with magnesium sulfate, and the drying agent was filtered off, after which the solvent was distilled off under reduced pressure. The residue thus obtained was purified by column chromatography (silica gel 60, mobile phase: ethyl acetate/n-hexane=1/4; v/v) to obtain 15.4 g of the titled compound (yellow oily substance).

MS (ESI pos.) m/z: 288([M+Na]$^+$) $^1$H-NMR (300 MHz, CDCl$_3$) δ (ppm); 1.43 & 1.46 (each-s, 9H), 2.36-2.56 (m, 1H), 2.58-2.82 (m, 1H), 3.69-3.92 (m, 2H), 3.77 (s, 3H) 4.40-4.61 (m, 1H)

Step 3-3: Synthesis of 1-(tert-butoxycarbonyl)-4,4-difluoro-L-proline 40 mL of a 2 mol/L sodium hydroxide aqueous solution was added dropwise over a period of 4 minutes under ice cooling to a 152 mL methanol solution of 15.2 g of the compound obtained in step 3-2, after which the reaction mixture was stirred for 2.5 hours at the same temperature. Upon completion of the reaction, the methanol was distilled off under reduced pressure, 100 mL of chloroform was added to the aqueous layer thus obtained, and then 90 mL of 1 mol/L hydrochloric acid was added dropwise over a period of 6 minutes under ice cooling. Once it was confirmed that the aqueous layer was acidic, liquid separation was performed, and the aqueous layer was extracted with chloroform (30 mL×2). The combined organic layer was washed with 50 mL of saturated brine and dried with magnesium sulfate, then the drying agent was filtered off and the solvent was distilled off under reduced pressure to obtain 14.1 g of residue (white solid). The residue thus obtained was crystallized from diisopropyl ether/n-hexane to obtain 12.6 g of the titled compound (colorless crystals).

MS (ESI neg.) m/z: 250([M−H]$^−$) $^1$H-NMR (300 MHz, DMSO-d$_6$) δ (ppm); 1.36 & 1.41 (each-s, 9H), 2.31-2.53 (m, 1H), 2.69-3.02 (m, 1H), 3.59-3.86 (m, 2H) 4.30-4.43 (m, 1H), 12.98 (brs, 1H)

Step 3-4: Synthesis of tert-butyl(2S)-2-[(dimethylamino)carbonyl]-4,4-difluoropyrrolidin-1-carboxylate A 40 mL tetrahydrofuran solution of 4.00 g of the compound obtained in step 3-3 and 3.23 g of 1-hydroxybenzotriazole monohydrate was stirred for 30 minutes under ice cooling. 3.66 g of 1-ethyl-3-(3-dimethylaminopropyl)carbodiimide hydrochloride was then added, and the reaction mixture was stirred for 30 minutes at the same temperature. 2.15 g of a 50% dimethylamine aqueous solution was added to the reaction solution, after which the reaction mixture was stirred for 1 hour at room temperature. 60 mL of chloroform and 50 mL of a 5% potassium carbonate aqueous solution were added to the reaction solution, liquid separation was performed, the aqueous layer was extracted with chloroform (50 mL×2), the combined organic layer was washed with 30 mL of saturated brine and then dried with magnesium sulfate, and the drying agent was filtered off, after which the solvent was distilled off under reduced pressure. The residue thus obtained was subjected to column chromatography (silica gel 60, mobile phase: ethyl acetate/n-hexane=1/1 to 10/0; v/v) to obtain 4.02 g of the titled compound (colorless solid).

MS (ESI pos.) m/z: 301([M+Na]$^+$) $^1$H-NMR (300 MHz, CDCl$_3$) δ (ppm); 1.41 & 1.46 (each-s, 9H), 2.28-2.48 (m, 1H), 2.55-2.73 (m, 1H), 2.99 & 3.00 (each-s, 3H), 3.06 & 3.10 (each-s, 3H), 3.75-4.02 (m, 2H), 4.68-4.91 (m, 1H)

Step 3-5: Synthesis of 4,4-difluoro-N,N-dimethyl-L-prolinamide trifluoroacetate 11 mL of trifluoroacetic acid was added under ice cooling to a 40 mL chloroform solution of 3.85 g of the compound obtained in step 3-4, and the reaction mixture was stirred for 2 hours at room temperature. The solvent was then distilled off under reduced pressure to obtain 8.02 g of residue (pale yellow oily substance). This compound was used in the following reaction without being purified.

MS (ESI pos.) m/z: 179 ([M+H]$^+$) $^1$H-NMR (300 MHz, DMSO-d$_6$) δ (ppm); 2.43-2.62 (m, 1H), 2.89-3.18 (m, 1H), 2.92 (s, 3H), 2.98 (s, 3H), 3.65-3.88 (m, 2H), 4.97 (t, J=8.7 Hz, 1H)

Step 3-6: Synthesis of 1-[5-(chloro-3-(2-methoxyphenyl)-2-oxo-2,3-dihydro-1H-indol-3-yl)-4,4-difluoro-N,N-dimethyl-L-prolinamide 7.64 g of triethylamine was added under ice cooling and a nitrogen atmosphere to a 40 mL chloroform solution of 3.88 g of 3,5-dichloro-3-(2-methoxyphenyl)-1,3-dihydro-2H-indol-2-one and the compound (unpurified) obtained in step 3-5, after which the reaction mixture was stirred for 15.5 hours at room temperature. The reaction solution was poured into 50 mL of a 5% potassium carbonate aqueous solution under stirring, and extraction was performed with chloroform (30 mL×2). The combined organic layer was washed with saturated brine and dried with magnesium sulfate, after which the drying agent was filtered off and the solvent was distilled off under reduced pressure to obtain 5.82 g of residue (Mars brown solid). This residue was separated and purified by column chromatography (silica gel 60, mobile phase: first time: ethyl acetate, second time: ethyl acetate/n-hexane=4/1; v/v) to obtain two kinds of diastereoisomer of the titled compound in amounts of 2.23 g (isomer A: colorless powder) and 2.70 g (isomer B: colorless powder).

Isomer A: [α]$_D^{29}$=+116° (c=0.425, chloroform) MS (ESI pos.) m/z: 472([M+Na]$^+$), (ESI neg.) m/z: 448([M–H]$^-$) $^1$H-NMR (300 MHz, DMSO-d$_6$) δ (ppm); 1.96-2.16 (m, 1H), 2.47-2.58 (m, 6H), 2.59-2.78 (m, 1H), 3.24-3.53 (m, 1H), 3.49 (s, 3H), 3.72-3.99 (m, 2H), 6.54 (d, J=2.2 Hz, 1H), 6.85 (d, J=8.2 Hz, 1H), 6.94 (dd, J=8.2, 0.9 Hz, 1H), 7.09-7.17 (m, 1H), 7.20 (dd, J=8.3, 2.3 Hz, 1H), 7.26-7.35 (m, 1H), 8.05 (dd, J=7.7, 1.6 Hz, 1H), 10.68 (s, 1H)

Isomer B: [α]$_D^{28}$=159° (c=0.296, chloroform) MS (ESI pos.) m/z: 472([M+Na]$^+$), (ESI neg.) m/z: 448([M–H]$^-$) $^1$H-NMR (300 MHz, DMSO-d$_6$) δ (ppm); 1.94-2.13 (m, 1H), 2.36-2.53 (m, 6H), 2.68-2.93 (m, 1H), 3.07-3.20 (m, 1H), 3.46 (s, 3H), 3.84-4.03 (m, 1H), 4.56-4.63 (m, 1H), 6.77 (d, J=8.2 Hz, 1H), 6.86 (d, J=2.2 Hz, 1H), 6.93 (dd, J=8.2, 1.1 Hz, 1H), 7.02-7.10 (m, 1H), 7.20 (dd, J=8.4, 2.2 Hz, 1H), 7.25-7.33 (m, 1H), 7.77 (dd, J=7.9, 1.8 Hz, 1H), 10.39 (s, 1H)

Step 3-7: Synthesis of 1-[5-chloro-1-[(2,4-dimethoxyphenyl)sulfonyl]-3-(2-methoxyphenyl)-2-oxo-2,3-dihydro-1H-indol-3-yl]-4,4-difluoro-N,N-dimethyl-L-prolinamide (levorotatory isomer)

1.94 g of the compound obtained in step 3-6 (isomer B) was used as the starting raw material to obtain 2.31 g of the titled compound (colorless, amorphous) by the same method as in step 1-5.

[α]$_D^{28}$=–191° (c=0.595, chloroform) MS (ESI pos.) m/z: 672([M+Na]$^+$) $^1$H-NMR (300 MHz, CDCl$_3$) δ (ppm); 2.06-3.88 (m, 7H), 2.41 (s, 3H), 2.76 (s, 3H), 3.69 (s, 3H), 3.87 (s, 3H), 4.79-4.97 (m, 1H), 6.44 (d, J=2.3 Hz, 1H), 6.58-6.63 (m, 1H), 6.78 (d, J=8.2 Hz, 1H), 6.95-7.03 (m, 1H), 7.03-7.11 (m, 1H), 7.20-7.30 (m, 2H), 7.81-7.88 (m, 1H), 7.92 (d, J=8.9 Hz, 1H), 8.14 (d, J=8.9 Hz, 1H)

EXAMPLE 4

Synthesis of methyl(4S)-1-[5-chloro-1-[(2,4-dimethoxyphenyl)sulfonyl]-3-(2-methoxyphenyl)-2-oxo-2,3-dihydro-1H-indol-3-yl]-4-fluoro-L-prolinate (diastereoisomer mixture)

Step 4-1: Synthesis of methyl(4S)-4-fluoro-L-prolinate trfluoroacetate 1.5 g of the compound obtained in step 2-1 was used as the raw material to obtain 2.56 g of the titled compound (yellow oily substance) by the same method as in step 1-3.

MS (ESI pos.) m/z: 270 ([M+Na]$^+$) $^1$H-NMR (300 MHz, DMSO-d$_6$) δ (ppm); 2.23-2.76 (m, 2H), 3.20-3.87 (m, 2H), 3.78 (s, 3H), 4.69 (dd, J=10.1, 3.9 Hz, 1H), 5.32-5.64 (m, 1H).

Step 4-2: Synthesis of methyl(4S)-1-[5-chloro-3-(2-methoxyphenyl)-2-oxo-2,3-dihydro-1H-indol-3-yl]-4-fluoro-L-prolinate 2.79 g of triethylamine was added under ice cooling and a nitrogen atmosphere to a 50 mL chloroform solution of 1.70 g of 3,5-dichloro-3-(2-methoxyphenyl)-1,3-dihydro-2H-indol-2-one and 1.03 g of the compound obtained in step 4-1, after which the reaction mixture was raised to room temperature and stirred for 13 hours at the same temperature. The reaction solution was stirred while a 50 mL saturated sodium hydrogencarbonate aqueous solution was added, and the reaction mixture was stirred for 15 minutes. After liquid separation, the aqueous layer thus obtained was extracted with chloroform. The combined organic layer was washed with saturated brine and dried with magnesium sulfate, after which the drying agent was filtered off and the solvent was distilled off under reduced pressure to obtain 2.54 g of residue (yellow, amorphous). The residue thus obtained purified by column chromatography (silica gel 60, mobile phase: ethyl acetate), and stirred and washed in diisopropyl ether to obtain 1.98 g of a diastereoisomer mixture of the titled compound (pale green, amorphous).

MS (ESI pos.) m/z: 441 ([M+Na]$^+$), (ESI neg.) m/z: 417 ([M–H]$^-$) $^1$H-NMR (300 MHz, CDCl$_3$) δ (ppm); 2.14-5.34 (m, 12H), 6.71-8.31 (m, 8H)

Step 4-3: Synthesis of methyl(4S)-1-[5-chloro-1-[(2,4-dimethoxyphenyl)sulfonyl]-3-(2-methoxyphenyl)-2-oxo-2,3-dihydro-1H-indol-3-yl]-4-fluoro-L-prolinate (diastereoisomer mixture)

1.00 g of the compound obtained in step 4-2 was used as the raw material to obtain 1.31 g of the titled compound (diastereoisomer mixture; colorless, amorphous) by the same method as in step 1-5.

MS (ESI pos.) m/z: 641 ([M+Na]$^+$) $^1$H-NMR (300 MHz, CDCl$_3$) δ (ppm); 1.47-5.01 (m, 18H), 6.42-8.22 (m, 10H)

EXAMPLE 5

Synthesis of tert-butyl 1-[5-chloro-1-[(2,4-dimethoxyphenyl)sulfonyl]-3-(2-methoxyphenyl)-2-oxo-2,3-dihydro-1H-indol-3-yl]-4-fluoro-L-prolinate (levorotatory isomer)

Step 5-1: Synthesis of 1-benzyl 2-methyl(2S)-4-fluoropyrrolidine-1,2-dicarboxylate 5.11 g of a mixture (approximately 3:1) of 1,1,2,3,3,3-hexafluoro-1-(diethylamino)propane and 1,2,3,3,3-pentafluoro-1-(diethylamino)-2-propene was added dropwise over a period of 10 minutes, and under ice cooling, to a suspension of 5.33 g of 1-benzyl 2-methyl(2S,4S)-4-hydroxypyrrolidine-1,2-dicarboxylate and 962 mg of sodium fluoride in 53 mL of dichloromethane, after which the reaction mixture was stirred for 16 hours at room temperature. After this, 100 mL of a 5% potassium carbonate aqueous solution was added under ice cooling to the reaction solution, and the reaction mixture was stirred for 30 minutes at the same temperature. After liquid separation, the aqueous layer thus obtained was extracted with chloroform (30 mL×2), and the combined organic layer was washed with 50 mL of saturated brine and dried with magnesium sulfate, after which the drying agent was filtered off and the solvent was distilled off under reduced pressure. The residue thus obtained was subjected to column chromatography (silica gel 60, mobile phase: ethyl acetate/n-hexane=3/7; v/v) to obtain 1.50 g of the titled compound (colorless oil).

MS (ESI pos.) m/z: 304 ([M+Na]$^+$) $^1$H-NMR (300 MHz, CDCl$_3$) δ (ppm); 2.00-2.26 (m, 1H), 2.37-2.71 (m, 1H), 3.48-3.80 (m, 4H), 3.83-4.09 (m, 1H), 4.46-4.59 (m, 1H), 5.00-5.52 (m, 3H), 7.26-7.44 (m, 5H)

Step 5-2: Synthesis of
1-[(benzyloxy)carbonyl]-4-fluoro-L-proline 3.6 mL of a 2 mol/L sodium hydroxide aqueous solution was added under ice cooling to a 15 mL methanol solution of 1.45 g of the compound obtained in step 5-1, and the reaction mixture was stirred for 4 hours at room temperature. The methanol was distilled off under reduced pressure, 30 mL of ethyl acetate was added, and the pH was adjusted to 2 with 1 mol/L hydrochloric acid under ice cooling. After liquid separation, the aqueous layer was extracted with ethyl acetate (10 mL×2), the combined organic layer was washed with 10 mL of saturated brine and dried with magnesium sulfate, and the drying agent was then filtered off and the solvent was distilled off under reduced pressure to obtain 1.98 g of a pale yellow oil. The residue thus obtained was subjected to column chromatography (silica gel 60, mobile phase: ethyl acetate) to obtain 1.46 g of the titled compound (pale yellow oily substance).

MS (ESI pos.) m/z: 290 ([M+H]$^+$) $^1$H-NMR (300 MHz, CDCl$_3$) δ (ppm); 2.21-2.47 (m, 1H), 2.55-2.79 (m, 1H), 3.51-3.76 (m, 1H), 3.91-4.15 (m, 1H), 4.41-4.65 (m, 1H), 5.08-5.36 (m, 3H), 6.89-7.47 (m, 6H)

Step 5-3: Synthesis of 1-benzyl 2-tert-butyl(2S)-4-fluoropyrrolidine-1,2-dicarboxylate A 28 mL t-butyl alcohol solution of 1.40 g of the compound obtained in step 5-2, 4.57 g of di-tert-butyl dicarbonate, and 192 mg of 4-(dimethylamino)pyridine was stirred for 16 hours at room temperature. The reaction solution was concentrated under reduced pressure, after which the residue thus obtained was purified by column chromatography (silica gel 60, mobile phase: ethyl acetate/n-hexane=1/4; v/v) to obtain 1.35 g of the titled compound (colorless oily substance).

MS (ESI pos.) m/z: 346 ([M+Na]$^+$) $^1$H-NMR (300 MHz, CDCl$_3$) δ (ppm); 1.29-1.51 (m, 9H), 1.96-2.23 (m, 1H), 2.51-2.71 (m, 1H), 3.55-3.76 (m, 1H), 3.83-4.09 (m, 1H), 4.41 (q, J=8.3 Hz, 1H), 5.08-5.33 (m, 3H), 7.24-7.40 (m, 5H)

Step 5-4: Synthesis of tert-butyl 4-fluoro-L-prolinate 1.25 g of the compound obtained in step 5-3 and 250 mg of 10% palladium-carbon were stirred for 1 hour at room temperature and under a hydrogen atmosphere in 12.5 mL of methanol. The insolubles were filtered off and the filtrate was concentrated under reduced pressure to obtain 704 mg of the titled compound (colorless oily substance).

MS (ESI pos.) m/z: 190 ([M+H]$^+$) $^1$H-NMR (300 MHz, CDCl$_3$) δ (ppm); 1.47 (s, 9H), 1.86-2.18 (m, 2H), 2.31-2.49 (m, 1H), 3.10-3.29 (m, 2H), 3.90 (t, J=7.9 Hz, 1H), 5.10-5.34 (m, 1H)

Step 5-5: Synthesis of tert-butyl 1-[5-chloro-3-(2-methoxyphenyl)-2-oxo-2,3-dihydro-1H-indol-3-yl]-4-fluoro-L-prolinate 2.09 g of triethylamine was added under ice cooling to an 11 mL chloroform solution of 1.06 g of 3,5-dichloro-3-(2-methoxyphenyl)-1,3-dihydro-2H-indol-2-one and 685 mg of the compound obtained in step 5-4 under a nitrogen atmosphere, after which the reaction mixture was raised to room temperature and stirred for 13 hours at that temperature. 10 mL of a 5% potassium carbonate aqueous solution was added to the reaction solution under stirring, and the reaction mixture was stirred for 15 minutes. After liquid separation, the aqueous layer thus obtained was extracted with chloroform. The combined organic layer was washed with saturated brine and dried with magnesium sulfate, then the drying agent was filtered off and the solvent was distilled off under reduced pressure to obtain 1.69 g of residue (colorless, amorphous). The residue thus obtained was separated and purified by column chromatography (silica gel 60, mobile phase: ethyl acetate/n-hexane=2/3; v/v) to obtain two kinds of diastereoisomer of the titled compound in amounts of 678 mg (isomer A: colorless solid) and 839 mg (isomer B: colorless, amorphous).

Isomer A: $[α]_D^{29}$=+75.7° (c=0.228 chloroform) MS (ESI pos.) m/z: 483 ([M+Na]$^+$), (ESI neg.) m/z: 459 ([M−H]$^−$) $^1$H-NMR (300 MHz, CDCl$_3$) δ (ppm); 1.29 (s, 9H), 1.84-2.06 (m, 1H), 2.33-2.49 (m, 1H), 3.40-3.65 (m, 2H), 3.56 (s, 3H), 3.95-4.11 (m, 1H), 5.02-5.26 (m, 1H), 6.73-6.84 (m, 3H), 7.08-7.15 (m, 2H), 7.25-7.32 (m, 1H), 8.03 (s, 1H), 8.12 (dd, J=7.7, 1.8 Hz, 1H)

Isomer B: $[α]_D^{28}$=−169° (c=0.197, chloroform) MS (ESI pos.) m/z: 483 ([M+Na]$^+$), (ESI neg.) m/z: 459 ([M−H]$^−$) $^1$H-NMR (300 MHz, CDCl$_3$) δ (ppm); 1.29 (s, 9H), 1.95-2.19 (m, 1H), 2.42-2.65 (m, 1H), 3.17-3.39 (m, 1H), 3.49-3.70 (m, 1H), 3.58 (s, 3H), 4.10-4.23 (m, 1H), 5.14-5.39 (m, 1H), 6.72 (d, J=8.2 Hz, 1H), 6.81 (dd, J=8.2, 1.0 Hz, 1H), 6.92 (d, J=2.0 Hz, 1H), 7.01-7.09 (m, 1H), 7.14 (dd, J=8.2, 2.2 Hz, 1H), 7.23-7.39 (m, 2H), 7.91 (dd, J=7.7, 1.8 Hz, 1H)

Step 5-6: Synthesis of tert-butyl 1-[5-chloro-1-[(2,4-dimethoxyphenyl)sulfonyl]-3-(2-methoxyphenyl)-2-oxo-2,3-dihydro-1H-indol-3-yl]-4-fluoro-L-prolinate (levorotatory isomer)

300 mg of the compound obtained in step 5-5 (isomer B) was used as the starting raw material to obtain 350 mg of the titled compound (colorless, amorphous) by the same method as in step 1-5.

$[α]_D^{28}$=−167° (c=0.209, chloroform) MS (ESI pos.) m/z: 683 ([M+Na]$^+$) $^1$H-NMR (300 MHz, CDCl$_3$) δ (ppm); 1.33 (s, 9H), 1.47-3.95 (m, 7H), 3.69 (s, 3H), 3.86 (s, 3H), 4.17-4.30 (m, 1H), 5.00-5.30 (m, 1H), 6.43 (d, J=2.2 Hz, 1H), 6.59 (dd, J=8.9, 2.3 Hz, 1H), 6.77 (d, J=8.1 Hz, 1H), 6.93-7.04 (m, 2H), 7.20-7.28 (m, 2H), 7.79 (dd, J=7.8, 1.6 Hz, 1H), 7.89 (d, J=8.9 Hz, 1H), 8.17 (d, J=8.9 Hz, 1H)

EXAMPLE 6

Synthesis of 1-[5-chloro-1-[(2,4-dimethoxyphenyl)sulfonyl]-3-(2-methoxyphenyl)-2-oxo-2,3-dihydro-1H-indol-3-yl]-4-fluoro-N,N-dimethyl-D-prolinamide (levorotatory isomer)

Step 6-1: Synthesis of tert-butyl(2R,4R)-2-[(dimethylamino)carbonyl]-4-hydroxypyrrolidine-1-carboxylate A 25 mL N,N-dimethylformamide solution of 2.50 g of (4S)-1-(tert-butoxycarbonyl)-4-hydroxy-D-proline and 2.19 g of 1-hydroxybenzotriazole was stirred for 5 minutes under cooling, after which 2.49 g of 1-ethyl-3-(3-dimethylaminopropyl)carbodiimide hydrochloride was added, and the reaction mixture was stirred for 30 minutes at the same temperature. After this, 1.95 g of a 50% dimethylamine aqueous solution was added to the reaction solution, and the reaction mixture was stirred for 16 hours at room temperature. Then 100 mL of chloroform and 50 mL of a 5% potassium carbonate aqueous solution were added to the reaction solution, and liquid separation was performed, after which the aqueous layer was extracted with chloroform (30 mL×2), and the combined organic layer was washed with 30 mL of saturated brine and dried with magnesium sulfate, then the drying agent was then filtered off and the solvent was distilled off under reduced pressure. The residue thus obtained was subjected to column chromatography (silica gel 60, mobile phase: ethyl acetate) to obtain 2.74 g of the titled compound (pale yellow solid).

MS (ESI pos.) m/z: 281 ([M+Na]$^+$) $^1$H-NMR (300 MHz, CDCl$_3$) δ (ppm); 1.39-1.48 (m, 9H), 1.95 (d, J=13.8 Hz, 1H), 2.17-2.34 (m, 1H), 2.88-3.29 (m, 6H), 3.48-3.56 (m, 1H), 3.64-3.86 (m, 1H), 4.32 (q, J=4.8 Hz, 1H), 4.66-4.83 (m, 1H)

Step 6-2: Synthesis of tert-butyl(2R)-2-[(dimethylamino)carbonyl]-4-fluoropyrrolidine-1-carboxylate 2.89 g of a mixture (approximately 3:1) of 1,1,2,3,3,3-hexafluoro-1-(diethylamino)propane and 1,2,3,3,3-pentafluoro-1-(diethylamino)-2-propene was added dropwise over a period of 10 minutes, and under ice cooling, to a suspension of 2.64 g of the compound obtained in step 6-1 and 545 mg of sodium fluoride in 26 mL of dichloromethane, after which the reaction mixture was stirred for 16 hours at room temperature. After this, 100 mL of a 5% potassium carbonate aqueous solution was added under ice cooling to the reaction solution, and the reaction mixture was stirred for 30 minutes at the same temperature. After liquid separation, the aqueous layer thus obtained was extracted with chloroform (30 mL×2), and the combined organic layer was washed with 50 mL of saturated brine and dried with magnesium sulfate, after which the drying agent was filtered off and the solvent was distilled off under reduced pressure. The residue thus obtained was subjected to column chromatography (silica gel 60, mobile phase: ethyl acetate) to obtain 2.17 g of the titled compound (colorless solid).

MS (ESI pos.) m/z: 283 ([M+Na]$^+$) $^1$H-NMR (300 MHz, CDCl$_3$) δ (ppm); 1.39-1.50 (m, 9H), 2.00-2.29 (m, 1H), 2.36-2.55 (m, 1H), 2.95-3.18 (m, 6H), 3.58-3.98 (m, 2H), 4.71-4.90 (m, 1H), 5.12-5.36 (m, 1H)

Step 6-3: Synthesis of 4-fluoro-N,N-dimethyl-D-prolinamide trifluoroacetate 10 mL of trifluoroacetic acid was added under ice cooling to a 30 mL chloroform solution of 2.09 g of the compound obtained in step 6-2, after which the reaction mixture was stirred for 2 hours at room temperature. The reaction mixture was then concentrated under reduced pressure, which gave 3.42 g of residue (pale yellow oily substance). This compound was used in the following reaction without being purified.

MS (ESI pos.) m/z: 161 ([M+H]$^+$) $^1$H-NMR (300 MHz, DMSO-d$_6$) δ (ppm); 1.96-2.22 (m, 1H), 2.67-2.88 (m, 1H), 2.92 (s, 3H), 3.02 (s, 3H), 3.38-3.66 (m, 2H), 4.74-4.88 (m, 1H), 5.36-5.61 (m, 1H), 8.84 (s, 1H), 10.15 (s, 1H)

Step 6-4: Synthesis of 1-[5-chloro-3-(2-methoxyphenyl)-2-oxo-2,3-dihydro-1H-indol-3-yl]-4-fluoro-N,N-dimethyl-D-prolinamide 4.65 g of triethylamine was added under ice cooling and a nitrogen atmosphere to a 20 mL chloroform solution 2.36 g of 3,5-dichloro-3-(2-methoxyphenyl)-1,3-dihydro-2H-indol-2-one and the 3.30 g of the compound obtained in step 6-3, after which the temperature was raised to room temperature and the reaction mixture was stirred for 13 hours that temperature. 10 mL of a 5% potassium carbonate aqueous solution was added to the reaction solution under stirring, and the reaction mixture was stirred for 15 minutes. After liquid separation, the aqueous layer thus obtained was extracted with chloroform. The combined organic layer was washed with saturated brine and dried with magnesium sulfate, then the drying agent was filtered off and the solvent was distilled off under reduced pressure to obtain 3.94 g of residue (colorless, amorphous). The residue thus obtained was separated and purified by column chromatography (silica gel 60, mobile phase: acetone/ethyl acetate=1/3 to 2/3; v/v), and each [part] was stirred and washed in diisopropyl ether to obtain two kinds of diastereoisomer of the titled compound in amounts of 874 mg (isomer A: colorless solid) and 1.80 g (isomer B: colorless solid).

Isomer A: $[\alpha]_D^{29}$=−128° (c=0.227, chloroform) MS (ESI pos.) m/z: 454 ([M+Na]$^+$), (ESI neg.) m/z: 430 ([M−H]$^-$) $^1$H-NMR (300 MHz, DMSO-d$_6$) δ (ppm); 1.65-1.90 (m, 1H), 2.16-2.34 (m, 1H), 2.43-2.61 (m, 6H), 3.22-3.34 (m, 1H), 3.32 (s, 3H), 3.77-3.96 (m, 2H), 5.05-5.29 (m, 1H), 6.49 (d, J=2.3 Hz, 1H), 6.81 (d, J=8.2 Hz, 1H), 6.92 (dd, J=8.2, 0.9 Hz, 1H), 7.07-7.15 (m, 1H), 7.18 (dd, J=8.3, 2.3 Hz, 1H), 7.25-7.33 (m, 1H), 8.05 (dd, J=7.8, 1.7 Hz, 1H), 10.51 (s, 1H)

Isomer B: $[\alpha]_D^{28}$=+188° (c=0.215, chloroform) MS (ESI pos.) m/z: 454 ([M+Na]$^+$), (ESI neg.) m/z: 430 ([M−H]$^-$) $^1$H-NMR (300 MHz, DMSO-d$_6$) δ (ppm); 1.79-2.00 (m, 1H), 2.21-2.77 (m, 7H), 2.86-3.08 (m, 1H), 3.38-3.85 (m, 1H), 3.46 (s, 3H), 4.57-4.69 (m, 1H), 5.18-5.43 (m, 1H), 6.74 (d, J=8.2 Hz, 1H), 6.83 (d, J=2.2 Hz, 1H), 6.89-6.94 (m, 1H), 6.97-7.06 (m, 1H), 7.14-7.20 (m, 1H), 7.23-7.31 (m, 1H), 7.86 (dd, J=7.7, 1.6 Hz, 1H), 10.32 (s, 1H)

Step 6-5: Synthesis of 1-[5-chloro-1-[(2,4-dimethoxyphenyl)sulfonyl]-3-(2-methoxyphenyl)-2-oxo-2,3-dihydro-1H-indol-3-yl]-4-fluoro-N,N-dimethyl-D-prolinamide (levorotatory isomer)

200 mg of the compound obtained in step 6-4 (isomer A) was used as the starting raw material to obtain 272 mg of the titled compound (colorless, amorphous) by the same method as in step 1-5.

$[\alpha]_D^{28}$=−129° (c=0.209, chloroform) MS (ESI pos.) m/z: 632 ([M+H]$^+$) $^1$H-NMR (300 MHz, CDCl$_3$) δ (ppm); 1.77-2.02 (m, 1H), 2.12-2.29 (m, 1H), 2.55 (s, 3H), 2.73 (s, 3H), 3.27 (s, 3H), 3.31-3.53 (m, 1H), 3.71-3.91 (m, 1H), 3.79 (s, 3H), 3.87 (s, 3H), 4.05 (dd, J=9.6, 6.9 Hz, 1H), 4.95-5.19 (m, 1H), 6.49 (d, J=2.2 Hz, 1H), 6.61 (dd, J=8.9, 2.3 Hz, 1H), 6.73 (dd, J=8.1, 0.9 Hz, 1H), 6.86 (d, J=2.3 Hz, 1H), 7.05-7.13 (m, 1H), 7.21-7.29 (m, 2H), 7.91 (d, J=8.7 Hz, 1H), 8.15 (dd, J=7.8, 1.7 Hz, 1H), 8.21 (d, J=8.9 Hz, 1H)

EXAMPLE 7

Synthesis of 3-[(2S)-2-(azetidine-1-ylcarbonyl)-4-fluoropyrrolidin-1-yl]-5-chloro-1-[(2,4-dimethoxyphenyl)sulfonyl]-3-(2-methoxyphenyl)-1,3-dihydro-2H-indol-2-one (levorotatory isomer)

Step 7-1: Synthesis of tert-butyl(2S,4S)-2-(azetidin-1-ylcarbonyl)-4-hydroxypyrrolidine-1-carboxylate 2.19 g of 1-hydroxybenzotriazole monohydrate and 2.49 g of 1-ethyl-3-(3-dimethylaminopropyl)carbodiimide hydrochloride were added under ice cooling to a 25 mL N,N-dimethylformamide solution of 2.50 g of (4S)-1-(tert-butoxycarbonyl)-4-hydroxy-L-proline and stirred for 30 minutes. 1.23 g of trimethyleneimine was added dropwise over a period of 1 minute to the reaction mixture, and the reaction mixture was stirred for 16 hours at room temperature. 30 mL of ethyl acetate and 20 mL of a 5% potassium carbonate aqueous solution were added to the reaction solution and stirred for 30 minutes. After liquid separation, the aqueous layer was extracted with ethyl acetate (50 mL×2), and the combined organic layer was washed with water (50 mL×3) and 50 mL of saturated brine, and then dried with anhydrous magnesium sulfate, after which the drying agent was filtered off, and the reaction mixture was concentrated under reduced pressure. The residue was purified by column chromatography (silica gel 60, mobile phase: ethyl acetate) to obtain 2.81 g of the titled compound (pale yellow solid).

MS (ESI pos.) m/z: 293([M+Na]$^+$) $^1$H-NMR (300 MHz, CDCl$_3$) δ (ppm); 1.44-1.51 (m, 9H), 1.92-2.01 (m, 1H), 2.13-2.43 (m, 3H), 3.42-3.52 (m, 1H), 3.60-3.83 (m, 1H), 3.97-4.81 (m, 7H)

Step 7-2: Synthesis of tert-butyl(2S)-2-(azetidin-1-ylcarbonyl)-4-fluoropyrrolidine-1-carboxylate 2.68 g of a mixture (approximately 3:1) of 1,1,2,3,3,3-hexafluoro-1-(diethylamino)propane and 1,2,3,3,3-pentafluoro-1-(diethylamino)-2-propene was added dropwise over a period of 10 minutes under ice cooling to a suspension of 2.71 g of the compound obtained in step 7-1 and 505 mg of sodium fluoride in 27 mL of dichloromethane, after which the reaction mixture was stirred for 16 hours at room temperature. 100 mL of a 5% potassium carbonate aqueous solution was added under ice cooling to the reaction solution, and the reaction mixture was stirred for 30 minutes at the same temperature. After liquid separation, the aqueous layer thus obtained was extracted with chloroform (30 mL×2), and the combined organic layer was washed with 50 mL of saturated brine and dried with magnesium sulfate, after which the drying agent was filtered off and the solvent was distilled off under reduced pressure. The residue thus obtained was subjected to column chromatography (silica gel 60, mobile phase: ethyl acetate) to obtain 2.30 g of the titled compound (colorless oil).

MS (ESI pos.) m/z: 295([M+Na]$^+$) $^1$H-NMR (300 MHz, CDCl$_3$) δ (ppm); 1.35-1.52 (m, 9H), 2.02-2.50 (m, 4H), 3.54-4.65 (m, 7H), 5.09-5.35 (m, 1H)

Step 7-3: Synthesis of (2S)-2-(azetidin-1-ylcarbonyl)-4-fluoropyrrolidine trifluoroacetate 10 mL of trifluoroacetic acid was added under ice cooling to a 30 mL chloroform solution of 2.20 g of the compound obtained in step 7-2, after which the reaction mixture was stirred for 2 hours at room temperature. After this, the reaction mixture was concentrated under reduced pressure to obtain 3.82 g of residue (pale yellow oily substance). This compound was used in the following reaction without being purified.

MS (ESI pos.) m/z: 173([M+H]$^+$) $^1$H-NMR (300 MHz, DMSO-d$_6$) δ (ppm); 1.97-2.36 (m, 3H), 2.48-2.75 (m, 1H), 3.37-3.66 (m, 2H), 3.89-4.07 (m, 2H), 4.14-4.50 (m, 3H), 5.38-5.61 (m, 1H)

Step 7-4: Synthesis of 3-[(2S)-2-(azetidin-1-ylcarbonyl)-4-fluoropyrrolidin-1-yl]-5-chloro-3-(2-methoxyphenyl)-1,3-dihydro-2H-indol-2-one 4.67 g of triethylamine was added under ice cooling and a nitrogen atmosphere to a 20 mL chloroform solution of 2.37 g of 3,5-dichloro-3-(2-methoxyphenyl)-1,3-dihydro-2H-indol-2-one and the compound (unpurified) obtained in step 7-3, after which the temperature was raised to room temperature and the reaction mixture was stirred for 13 hours at that temperature. 10 mL of a 5% potassium carbonate aqueous solution was added to the reaction solution under stirring, and the reaction mixture was stirred for 15 minutes. After liquid separation, the aqueous layer thus obtained was extracted with chloroform. The combined organic layer was washed with saturated brine and dried with magnesium sulfate, then the drying agent was filtered off and the solvent was distilled off under reduced pressure to obtain 4.02 g of residue (Mars brown solid). This was separated and purified by column chromatography (silica gel 60, mobile phase: ethyl acetate/acetone=3/1 to 1/1; v/v) to obtain two kinds of diastereoisomer of the titled compound, which were stirred and washed with diisopropyl ether and obtained in amounts of 874 mg (isomer A: colorless solid) and 1.45 g (isomer B: colorless, amorphous).

Isomer A: $[\alpha]_D^{29}$=+168° (c=0.205, chloroform) MS (ESI pos.) m/z: 444 ([M+H]$^+$), (ESI neg.) m/z: 442 ([M−H]$^−$) $^1$H-NMR (300 MHz, DMSO-d$_6$) δ (ppm); 1.67-2.30 (m, 4H), 3.13-3.73 (m, 5H), 3.48 (s, 3H), 3.78-4.02 (m, 2H), 5.02-5.27 (m, 1H), 6.59 (d, J=2.2 Hz, 1H), 6.87 (d, J=8.2 Hz, 1H), 6.93 (dd, J=8.2, 1.1 Hz, 1H), 7.11 (dt, J=7.5, 1.2 Hz, 1H), 7.23-7.33 (m, 2H), 7.98 (dd, J=7.6, 1.7 Hz, 1H), 10.54 (s, 1H)

Isomer B: $[\alpha]_D^{28}$=−137° (c=0.223, chloroform) MS (ESI pos.) m/z: 466 ([M+Na]$^+$), (ESI neg.) m/z: 442 ([M−H]$^−$) $^1$H-NMR (300 MHz, DMSO-d$_6$) δ (ppm); 1.70-2.06 (m, 3H), 2.16-2.38 (m, 1H), 2.82-3.02 (m, 1H), 3.05-3.15 (m, 1H), 3.41-3.72 (m, 3H), 3.48 (s, 3H), 3.74-3.86 (m, 1H), 4.08-4.23 (m, 1H), 5.17-5.42 (m, 1H), 6.81-6.87 (m, 2H), 6.91-6.97 (m, 1H), 7.02-7.09 (m, 1H), 7.22-7.34 (m, 2H), 7.83 (dd, J=7.8, 1.7 Hz, 1H), 10.40 (s, 1H)

Step 7-5: Synthesis of 3-[(2S)-2-(azetidin-1-ylcarbonyl)-4-fluoropyrrolidin-1-yl]-5-chloro-1-[(2,4-dimethoxyphenyl)sulfonyl]-3-(2-methoxyphenyl)-1,3-dihydro-2H-indol-2-one (levorotatory isomer)

300 mg of the compound obtained in step 7-4 (isomer B) was used as the starting raw material to obtain 353 mg of the titled compound (colorless, amorphous) by the same method as in step 1-5.

$[\alpha]_D^{28}$=−204° (c=0.220, chloroform) MS (ESI pos.) m/z: 666 ($[M+Na]^+$) $^1$H-NMR (300 MHz, CDCl$_3$) δ (ppm); 1.50-4.00 (m, 19H), 4.36-4.47 (m, 1H), 5.13-5.41 (m, 1H), 6.42 (d, J=2.3 Hz, 1H), 6.60 (dd, J=8.9, 2.3 Hz, 1H), 6.80-6.86 (m, 1H), 7.06-7.13 (m, 2H), 7.24-7.34 (m, 2H), 7.86 (dd, J=7.9, 1.6 Hz, 1H), 7.93 (d, J=8.9 Hz, 1H), 8.15 (d, J=9.0 Hz, 1H)

EXAMPLE 8

Synthesis of 1-[5-chloro-1-[(2,4-dimethoxyphenyl)sulfonyl]-3-(2-methoxyphenyl)-2-oxo-2,3-dihydro-1H-indol-3-yl]-N-ethyl-4-fluoro-L-prolinamide (levorotatory isomer)

Step 8-1: Synthesis of benzyl(2S)-2-[(ethylamino)carbonyl]-4-fluoropyrrolidin-1-carboxylate 2.43 g of 1-hydroxybenzotriazole monohydrate and 2.75 g of 1-ethyl-3-(3-dimethylaminopropyl)carbodiimide hydrochloride were added under ice cooling to a 32 mL N,N-dimethylformamide solution of 3.02 g of the compound obtained in step 5-2, and the reaction mixture was stirred for 30 minutes. 1.16 g of a 70% ethylamine aqueous solution was added to the reaction mixture. The reaction mixture was raised to room temperature and stirred for 14 hours. 50 mL of ethyl acetate and 30 mL of a 5% potassium carbonate aqueous solution were added to the reaction solution, and the reaction mixture was stirred for 30 minutes at room temperature. After liquid separation, the aqueous layer was extracted with chloroform (20 mL×2), the combined organic layer was washed with saturated water (50 mL×2) and saturated brine (20 mL) and dried with magnesium sulfate, the drying agent was filtered off, and the reaction mixture was concentrated under reduced pressure. The residue was purified by column chromatography (silica gel 60, mobile phase: ethyl acetate/n-hexane=7/3; v/v) to obtain 1.92 g of the titled compound (colorless solid).

MS (ESI pos.) m/z: 317 ($[M+Na]^+$) $^1$H-NMR (300 MHz, CDCl$_3$) δ (ppm); 0.81-1.30 (m, 3H), 2.12-2.76 (m, 2H), 3.01-3.69 (m, 3H), 3.92-4.52 (m, 2H), 4.97-5.35 (m, 3H), 5.62-6.80 (m, 1H), 7.23-7.45 (m, 5H)

Step 8-2: Synthesis of N-ethyl-4-fluoro-L-prolinamide

A suspension of 1.80 g of the compound obtained in step 8-1 and 360 mg of 10% palladium-carbon in 36 mL of methanol was stirred for 3 hours at room temperature and under hydrogen atmosphere. The insolubles were filtered off and the reaction mixture was concentrated under reduced pressure to obtain 1.07 g of the titled compound. This compound was used in the following reaction without being purified.

MS (ESI pos.) m/z: 183 ($[M+Na]^+$) $^1$H-NMR (300 MHz, CDCl$_3$) δ (ppm); 1.14 (t, J=7.2 Hz, 3H), 1.93-2.18 (m, 1H), 2.26-2.87 (m, 3H), 3.17-3.38 (m, 3H), 3.98 (q, J=8.6 Hz, 1H), 5.07-5.30 (m, 1H), 7.56 (s, 1H)

Step 8-3: Synthesis of 1-[5-chloro-3-(2-methoxyphenyl)-2-oxo-2,3-dihydro-1H-indol-3-yl]-N-ethyl-4-fluoro-L-prolinamide 1.0 mL of triethylamine was added under ice cooling to a 15 mL chloroform solution of 1.02 g of 3,5-dichloro-3-(2-methoxyphenyl)-1,3-dihydro-2H-indol-2-one and 530 mg of the compound obtained in step 8-2, after which the reaction mixture was stirred for 18.5 hours at room temperature. 20 mL of a 5% potassium carbonate aqueous solution was poured into the reaction solution under stirring, and extraction was performed with chloroform (20 mL×2). The combined organic layer was washed with saturated brine and dried with sodium sulfate, then the drying agent was filtered off and the solvent was distilled off under reduced pressure. The residue thus obtained was separated and purified by column chromatography (silica gel 60, mobile phase: ethyl acetate/acetone=98/2; v/v) to obtain two kinds of diastereoisomer of the titled compound in amounts of 708 mg (isomer A: colorless, amorphous) and 501 mg (isomer B: colorless, amorphous).

Isomer A: $[\alpha]_D^{25}$=−171° (c=0.200, chloroform) MS (ESI pos.) m/z: 432($[M+H]^+$), (ESI pos.) m/z: 454($[M+Na]^+$), (ESI neg.) m/z: 430($[M−H]^-$) $^1$H-NMR (300 MHz, DMSO-d$_6$) δ (ppm); 0.85 (t, J=7.2 Hz, 3H), 1.86-2.06 (m, 1H), 2.16-2.41 (m, 1H), 2.72-2.95 (m, 3H), 3.38-3.58 (m, 4H), 4.07 (dd, J=8.6, 4.5 Hz, 1H), 5.09-5.39 (m, 1H), 6.71-6.85 (m, 2H), 6.89-7.19 (m, 3H), 7.21-7.32 (m, 1H), 7.39 (s, 1H), 7.76 (dd, J=7.7, 1.6 Hz, 1H), 10.41 (s, 1H)

Isomer B: $[\alpha]_D^{25}$=+54° (c=0.224, chloroform) MS (ESI pos.) m/z: 454($[M+Na]^+$), (ESI neg.) m/z: 430($[M−H]^-$) $^1$H-NMR (300 MHz, DMSO-d$_6$) δ (ppm); 0.89-0.98 (t, J=7.0 Hz, 3H), 1.71-1.96 (m, 1H), 2.08-2.28 (m, 1H), 2.80-2.94 (m, 2H), 3.20-3.55 (m, 5H), 3.74-3.91 (m, 1H), 4.98-5.25 (m, 1H), 6.53 (d, J=2.2 Hz, 1H), 6.73 (d, J=8.2 Hz, 1H), 6.92 (dd, J=8.2, 1.0 Hz, 1H), 7.06-7.15 (m, 2H), 7.25-7.35 (m, 1H), 7.47-7.55 (m, 1H), 8.13 (dd, J=7.8, 1.7 Hz, 1H), 10.50 (s, 1H)

Step 8-4: Synthesis of 1-[5-chloro-1-[(2,4-dimethoxyphenyl)sulfonyl]-3-(2-methoxyphenyl)-2-oxo-2,3-dihydro-1H-indol-3-yl]-N-ethyl-4-fluoro-L-prolinamide (levorotatory isomer)

200 mg of the compound obtained in step 8-3 (isomer A) was used as the starting raw material to obtain 65 mg of the titled compound (colorless, amorphous) by the same method as in step 1-5.

$[\alpha]_D^{25}$=−199° (c=0.153, chloroform) MS (ESI pos.) m/z: 632($[M+H]^+$), (ESI neg.) m/z: 630($[M−H]^-$) $^1$H-NMR (499 MHz, CDCl$_3$) δ (ppm); 0.78 (t, J=7.2 Hz, 3H), 1.96-2.92 (m, 5H), 3.18-3.35 (m, 1H), 3.54 (s, 3H), 3.68 (s, 3H), 3.83-3.96 (m, 4H), 4.96-5.20 (m, 1H), 6.27-6.32 (m, 1H), 6.44 (d, J=2.1 Hz, 1H), 6.62 (dd, J=9.0, 2.3 Hz, 1H), 6.75 (d, J=8.2 Hz, 1H), 6.94 (d, J=2.1 Hz, 1H), 6.98-7.03 (m, 1H), 7.19-7.28 (m, 2H), 7.71-7.75 (m, 1H), 7.88 (d, J=8.8 Hz, 1H), 8.14 (d, J=8.8 Hz, 1H)

EXAMPLE 9

Synthesis of (4R)-1-{3-(2,4-dimethoxyphenyl)-1-[(2,4-dimethoxyphenyl)sulfonyl]-5,6-dimethoxy-2-oxo-2,3-dihydro-1H-indol-3-yl}-4-fluoro-N,N-dimethyl-L-prolinamide (levorotatory isomer, dextrorotatory isomer)

Step 9-1: Synthesis of 3-(2,4-dimethoxyphenyl)-3-hydroxy-5,6-dimethoxy-1,3-dihydro-2H-indol-2-one 293 mg of 60% sodium hydride was added under ice cooling and a nitrogen gas flow to a suspension of 1.38 g of 5,6-dimethoxy-1H-indol-2,3-dione in 30 mL of tetrahydrofuran, and the reaction mixture was stirred for 1 hour at the same temperature. A Grignard's reagent generated in 20 mL of tetrahydrofuran using 3.61 g of 2,4-dimethoxybromobenzene and 486 mg of magnesium was added dropwise over a period of 3 minutes to the reaction mixture under ice cooling, after which the reaction mixture was stirred for 13 hours at room temperature. 20 mL of saturated aqueous ammonium chloride and 40 mL of ethyl acetate were added to the reaction solution, and the reaction mixture was stirred for 30 minutes at room temperature. After liquid separation, the aqueous layer was extracted with ethyl acetate (20 mL×2), the combined organic layer was washed with saturated brine and dried with magnesium sulfate, and the drying agent was then filtered off and the filtrate was concentrated under reduced pressure. The residue thus obtained was purified by column chromatography (silica gel 60, mobile phase: ethyl acetate) to obtain 1.37 g of the titled compound (brown solid).

MS (ESI pos.) m/z: 368 ([M+Na]$^+$) $^1$H-NMR (300 MHz, DMSO-D$_6$) δ (ppm); 3.43 (s, 3H), 3.55 (s, 3H), 3.75 (s, 6H), 6.16 (s, 1H), 6.40 (s, 1H), 6.44 (d, J=2.3 Hz, 1H), 6.47 (s, 1H), 6.59 (dd, J=8.6, 2.3 Hz, 1H), 7.68 (d, J=8.6 Hz, 1H), 9.98 (s, 1H)

Step 9-2: Synthesis of
(4R)-4-fluoro-N,N-dimethyl-L-prolinamide 15 mL of trifluoroacetic acid was added to a 50 mL chloroform solution of 5.00 g of the compound obtained in step 1-2a or 1-2b, and the reaction mixture was stirred for 2 hours at room temperature. The reaction solution was concentrated under reduced pressure, after which 100 mL of chloroform was added to the residue thus obtained, and a 5% potassium carbonate aqueous solution was added under ice cooling until the aqueous layer turned basic. After liquid separation, the aqueous layer was extracted with chloroform. The combined organic layer was washed with 30 mL of saturated brine and dried with magnesium sulfate, the drying agent was filtered off, and the reaction mixture was concentrated under reduced pressure. The residue thus obtained was purified by column chromatography (silica gel 60, mobile phase: chloroform/methanol/28% aqueous ammonia=10/1/0.1; v/v) to obtain 3.10 g of the titled compound (yellow oily substance).

MS (ESI pos.) m/z: 161 ([M+H]$^+$) $^1$H-NMR (300 MHz, CDCl$_3$) δ (ppm); 1.79-2.02 (m, 1H), 2.04-2.67 (m, 1H), 2.26-2.42 (m, 1H), 2.99 (s, 3H), 3.06-3.25 (m, 1H), 3.07 (s, 3H), 3.37 (ddd, J=33.0, 13.3, 4.3 Hz, 1H), 4.17 (dd, J=9.2, 6.7 Hz, 1H), 5.16-5.39 (m, 1H)

Step 9-3: Synthesis of (4R)-1-[3-(2,4-dimethoxyphenyl)-5,6-dimethoxy-2-oxo-2,3-dihydro-1H-indol-3-yl]-4-fluoro-N,N-dimethyl-L-prolinamide (mixture of diastereoisomers)

362 mL of thionyl chloride was added at −78° C. and under a nitrogen gas flow to a 14 mL chloroform solution of 700 mg of the compound obtained in step 9-1 and 240 mg of pyridine, and the reaction mixture was stirred for 30 minutes at the same temperature. After this, a 5 mL chloroform solution of 485 mg of the compound obtained in step 9-2 and 2.05 g of triethylamine was added over a period of 2 minutes, after which the temperature was raised to room temperature and the reaction mixture was stirred for 15 hours at that temperature. 50 mL of ethyl acetate and 30 mL of a 5% potassium carbonate aqueous solution were added to the reaction solution, and the reaction mixture was stirred for 5 minutes. After liquid separation, the aqueous layer was extracted with ethyl acetate (30 mL×2), the combined organic layer was washed with saturated brine and dried with magnesium sulfate, the drying agent was filtered off, and the reaction mixture was concentrated under reduced pressure. The residue thus obtained was purified by column chromatography (silica gel 60N, mobile phase: ethyl acetate/acetone=1/1; v/v) to obtain 697 mg of mixture of diastereoisomers of the titled compound (reddish-brown, amorphous).

MS (ESI pos.) m/z: 510 ([M+Na]$^+$) $^1$H-NMR (300 MHz, CDCl$_3$) δ (ppm); 1.82-5.47 (m, 24H), 6.35-6.67 (m, 4H), 7.44-8.15 (m, 2H)

Step 9-4: Synthesis of (4R)-1-{3-(2,4-dimethoxyphenyl)-1-[(2,4-dimethoxyphenyl)sulfonyl]-5,6-dimethoxy-2-oxo-2,3-dihydro-1H-indol-3-yl}-4-fluoro-N,N-dimethyl-L-prolinamide (levorotatory isomer, dextrorotatory isomer)

200 mg of the diastereoisomer mixture obtained in step 9-3 was added under ice cooling to a suspension of 18 mg of sodium hydride in 2 mL of N,N-dimethylformamide under a nitrogen atmosphere, and the reaction mixture was stirred for 1 hour at the same temperature. 107 mg of 2,4-dimethoxybenzenesulfonyl chloride was added and the reaction mixture was stirred for 30 minutes at the same temperature, after which 30 mL of ethyl acetate and 20 mL of a 5% potassium carbonate aqueous solution were added, and the reaction mixture was stirred for 15 minutes at room temperature. After liquid separation, the aqueous layer was extracted with ethyl acetate (20 mL×2), the combined organic layer was dried with magnesium sulfate, the drying agent was filtered off, and the solvent was distilled off under reduced pressure to obtain 300 mg of residue (brown oily substance). The residue thus obtained was separated and purified by column chromatography (silica gel 60N, mobile phase: ethyl acetate/acetone=3/1; v/v) to obtain two kinds of diastereoisomer of the titled compound in amounts of 30 mg (isomer A: reddish-brown, amorphous) and 27 mg (isomer B: reddish-brown, amorphous).

Isomer A: $[α]_D^{28}$=−169° (c=0.111, chloroform) MS (ESI pos.) m/z: 710 ([M+Na]$^+$) $^1$H-NMR (300 MHz, CDCl$_3$) δ (ppm); 1.85-5.44 (m, 9H), 2.38 (s, 3H), 2.78 (s, 3H), 3.64 (s, 3H), 3.75 (s, 3H), 3.77 (s, 3H), 3.86 (s, 3H), 3.95 (s, 3H), 6.34 (d, J=2.3 Hz, 1H), 6.40-6.48 (m, 2H), 6.55-6.63 (m, 2H), 7.62-7.69 (m, 2H), 8.16 (d, J=9.0 Hz, 1H)

Isomer B: $[α]_D^{28}$=+177° (c=0.104, chloroform) MS (ESI pos.) m/z: 710 ([M+Na]$^+$) $^1$H-NMR (300 MHz, CDCl$_3$) δ (ppm); 1.76-2.03 (m, 1H), 2.10-2.26 (m, 1H), 2.53-2.56 (m, 3H), 2.63 (s, 3H), 3.22 (s, 3H), 3.31-3.52 (m, 1H), 3.62-4.01 (m, 1H), 3.70 (s, 3H), 3.77 (s, 3H), 3.80 (s, 3H), 3.87 (s, 3H), 3.95 (s, 3H), 4.08-4.16 (m, 1H), 4.97-5.20 (m, 1H), 6.29 (d, J=2.3 Hz, 1H), 6.41 (s, 1H), 6.49 (d, J=2.3 Hz, 1H), 6.56-6.65 (m, 2H), 7.61 (s, 1H), 8.04 (d, J=8.6 Hz, 1H), 8.23 (d, J=9.0 Hz, 1H)

EXAMPLE 10

Synthesis of (4R)-1-[5-chloro-1-[(2,4-dimethoxyphenyl)sulfonyl]-3-(2-isopropylphenyl)-2-oxo-2,3-dihydro-1H-indol-3-yl]-4-fluoro-N,N-dimethyl-L-prolinamide (levorotatory isomer)

Step 10-1: Synthesis of 5-chloro-3-hydroxy-3-(2-isopropylphenyl)-1,3-dihydro-2H-indol-2-one Several drops of a 12 mL tetrahydrofuran solution of 8.2 g of 1-bromo-2-isopropylbenzene were added to a 5 mL tetrahydrofuran solution of 1.2 g of magnesium under a nitrogen atmosphere to initiate the reaction, after which the rest was gradually added drop-wise at a rate at which heating reflux was maintained. Upon completion of the dropping, the reaction mixture was refluxed for 0.5 hour in an oil bath, and then cooled to room temperature. A reagent prepared as above was gradually added drop-wise under ice cooling and a nitrogen atmosphere to a suspension of 3 g of 5-chloro-1H-indol-2,3-dione in 22 mL of tetrahydrofuran. Upon completion of the dropping, the temperature was raised to room temperature, and then the reaction mixture was stirred for 2 hours at that temperature. A 3N hydrochloric acid aqueous solution was poured into the reaction solution, and extraction was performed with ethyl acetate. The organic layer was washed with water and saturated brine and dried with magnesium sulfate, and the drying agent was then filtered off and the solvent was distilled off under reduced pressure. The residue was purified by column chromatography (silica gel 60, mobile phase: ethyl acetate/hexane=1/2; v/v) to obtain 4.9 g of the titled compound (pale yellow, amorphous).

MS (ESI pos.) m/z: 302([M+H]$^+$, 324([M+Na]$^+$), (ESI neg.) m/z: 300([M–H]$^-$) $^1$H-NMR (300 MHz, CDCl$_3$) δ (ppm); 0.71 (d, J=6.7 Hz, 3H), 1.13 (d, J=6.7 Hz, 3H), 2.31-2.66 (m, 1H), 3.94 (s, 1H), 6.73 (d, J=8.1 Hz, 1H), 7.00 (d, J=8.1 Hz, 1H), 7.16 (dd, J=8.4, 2.2 Hz, 1H), 7.21-7.46 (m, 1H), 7.87 (d, J=2.2 Hz, 1H), 8.79 (s, 1H)

Step 10-2: Synthesis of (4R)-1-[5-chloro-3-(2-isopropylphenyl)-2-oxo-2,3-dihydro-1H-indol-3-yl]-4-fluoro-N,N-dimethyl-L-prolinamide 0.6 mL of pyridine was added to a 15.6 mL chloroform solution of 1.5 g of the compound obtained in step 10-1, and a 1 mL chloroform solution of 0.54 mL of thionyl chloride was added dropwise under ice cooling, after which the reaction mixture was stirred for 1 hour at room temperature. Upon completion of the reaction, water was added and extraction was performed with chloroform. The organic layer was washed with saturated brine and dried with magnesium sulfate, after which the solvent was distilled off under reduced pressure. 3.5 mL of triethylamine was added to a 25 mL chloroform solution of the residue and the compound obtained in step 9-2, after which the reaction mixture was stirred for 60 hours at room temperature. Water was added to the reaction solution, extraction was performed with chloroform, and the organic layer was washed with saturated brine and dried with magnesium sulfate, after which the solvent was distilled off under reduced pressure. The residue was separated and purified by column chromatography (silica gel 60, mobile phase: methanol/chloroform=1/9; v/v, ethyl acetate) to obtain two kinds of diastereoisomer of the titled compound in amounts of 1.08 g (isomer A: colorless, amorphous) and 0.15 g (isomer B: colorless, amorphous).

Isomer A: $[\alpha]_D^{28}$=+110° (c=0.218 chloroform) MS (ESI pos.) m/z: 444([M+H]$^+$, 466([M+Na]$^+$), (ESI neg.) m/z: 442 ([M–H]$^-$) $^1$H-NMR (300 MHz, DMSO-d$_6$) δ (ppm); 0.45 (d, J=6.5 Hz, 3H), 1.08 (d, J=6.7 Hz, 3H), 2.18-2.42 (m, 2H), 2.46 (s, 3H), 2.57 (s, 3H), 3.18-3.51 (m, 1H), 3.62-3.95 (m, 2H), 5.09-5.27 (m, 1H), 6.47 (s, 1H), 6.91 (d, J=8.2 Hz, 1H), 7.10-7.49 (m, 4H), 8.11-8.60 (m, 1H), 10.87 (s, 1H)

Isomer B: $[\alpha]_D^{28}$=–136° (c=0.215, chloroform) MS (ESI pos.) m/z: 444([M+H]$^+$, 466([M+Na]$^+$), (ESI neg.) m/z: 442 ([M–H]$^-$) $^1$H-NMR (300 MHz, DMSO-d$_6$) δ (ppm); 0.34-0.58 (m, 3H), 1.06 (d, J=6.5 Hz, 3H), 1.75-2.03 (m, 1H), 2.31-2.64 (m, 5H), 2.87-3.23 (m, 1H), 3.43-3.74 (m, 1H), 4.46-4.65 (m, 1H), 5.24-5.43 (m, 1H), 6.72-6.93 (m, 2H), 7.13-7.38 (m, 4H), 7.99 (s, 1H), 10.62 (s, 1H)

Step 10-3: Synthesis of (4R)-1-[5-chloro-1-[(2,4-dimethoxyphenyl)sulfonyl]-3-(2-isopropylphenyl)-2-oxo-2,3-dihydro-1H-indol-3-yl]-4-fluoro-N,N-dimethyl-L-prolinamide (levorotatory isomer)

42 mg of the compound obtained in step 10-2 (isomer B) was used as the starting raw material to obtain 32 mg of the titled compound (colorless, amorphous) by the same method as in step 1-5.

$[\alpha]_D^{28}$=–177° (c=0.100, chloroform) MS (ESI pos.) m/z: 644([M+H]$^+$, 666([M+Na]$^+$), (ESI neg.) m/z: 642([M–H]$^-$) $^1$H-NMR (500 MHz, CDCl$_3$) δ (ppm); 0.34-0.84 (m, 6H), 1.66-2.81 (m, 11H), 3.26 (s, 1H), 3.60-3.94 (m, 6H), 5.14-5.57 (m, 1H), 6.39-6.70 (m, 2H), 6.80-7.35 (m, 5H), 7.82-8.32 (m, 3H)

EXAMPLE 11

Synthesis of (4R)-1-[1-[(2,4-dimethoxyphenyl)sulfonyl]-3-(2-hydroxyphenyl)-2-oxo-1,2,3,5,6,7-hexahydrocyclopenta[f]indol-3-yl]-4-fluoro-N,N-dimethyl-L-prolinamide (levorotatory isomer)

Step 11-1: Synthesis of 3-[2-(benzyloxy)phenyl]-3-hydroxy-3,5,6,7-tetrahydrocyclopenta[f]indol-2(1H)-one Several drops of a 6 mL diethyl ether solution of 5.3 g of 2-benzyloxybromobenzene were added to a suspension of 583 mg of magnesium in 2 mL of diethyl ether under a nitrogen atmosphere to initiate the reaction, after which the rest was gradually added dropwise at a rate at which heating reflux was maintained. Upon completion of the dropping, the reaction mixture was heated and refluxed for 2 hours in an oil bath, and then cooled to room temperature. A reagent prepared as above was gradually added dropwise under ice cooling and a nitrogen atmosphere to an 11 mL tetrahydrofuran solution of 1.5 g of 1,5,6,7-tetrahydrocyclopenta[f]indol-2,3-dione. Upon completion of the dropping, the temperature was raised to room temperature, and then the reaction mixture was stirred for 16 hours at that temperature. A 1 mol/L hydrochloric acid aqueous solution was poured into the reaction solution, and extraction was performed with ethyl acetate. The organic layer was washed with water and saturated brine and dried with magnesium sulfate, and the drying agent was then filtered off and the solvent was distilled off under reduced pressure. The residue was refined by column chromatography (silica gel 60, mobile phase: ethyl acetate/hexane=1/2; v/v) to obtain 1.10 g of the titled compound (colorless powder).

MS (ESI pos.) m/z: 394([M+Na]$^+$), (ESI neg.) m/z: 370 ([M–H]$^-$) $^1$H-NMR (300 MHz, DMSO-d$_6$) δ (ppm); 1.90-2.05 (m, 2H), 2.70 (t, J=7.4 Hz, 2H), 2.81 (t, J=7.5 Hz, 2H), 4.84 (s, 2H), 6.29 (s, 1H), 6.59 (d, J=9.0 Hz, 2H), 6.82-6.92 (m, 3H), 6.97-7.04 (m, 1H), 7.14-7.24 (m, 4H), 7.86 (dd, J=7.7, 1.8 Hz, 1H), 10.04 (s, 1H)

Step 11-2: Synthesis of (4R)-1-{3-[2-(benzyloxy)phenyl]-2-oxo-1,2,3,5,6,7-hexahydrocyclopenta[f]indol-3-yl}-4-fluoro-N,N-dimethyl-L-prolinamide (levorotatory isomer)

0.35 mL of pyridine was added to a 9 mL chloroform solution of 1.10 g of the compound obtained in step 11-1, and a 1 mL chloroform solution of 0.31 mL of thionyl chloride was added dropwise under ice cooling, after which the reaction mixture was stirred for 1 hour at room temperature. Upon completion of the reaction, the solvent was distilled off under reduced pressure. 4 mL of triethylamine was added under ice cooling to a 10 mL chloroform solution of the residue and the compound obtained in step 9-2, after which the reaction mixture was stirred for 15 hours at room temperature. Water was added to the reaction solution, extraction was performed with chloroform, and the organic layer was washed with saturated brine and dried with magnesium sulfate, after which the solvent was distilled off under reduced pressure. The residue was purified by column chromatography (silica gel 60, mobile phase: methanol/chloroform=1/9; v/v, ethyl acetate) to obtain 971 mg of the titled compound (pale yellow, amorphous).

$[\alpha]_D^{28}$=−69° (c=0.210, chloroform) MS (ESI pos.) m/z: 514([M+H]$^+$, 536([M+Na]$^+$), (ESI neg.) m/z: 512([M−H]$^-$) $^1$H-NMR (300 MHz, DMSO-d$_6$) δ (ppm); 1.82-2.05 (m, 3H), 2.16-2.91 (m, 3H), 2.32 (s, 3H), 2.63-2.73 (m, 2H), 2.78 (t, J=7.2 Hz, 2H), 4.81-4.97 (m, 2H), 5.22-5.40 (m, 1H), 6.55 (s, 1H), 6.66 (s, 3H), 6.79-7.07 (m, 4H), 7.09-7.26 (m, 4H), 7.88 (d, J=8.4 Hz, 2H), 9.99 (s, 1H)

Step 11-3: Synthesis of (4R)-1-{3-[2-(benzyloxy)phenyl]-1-[(2,4-dimethoxyphenyl)sulfonyl]-2-oxo-1,2,3,5,6,7-hexahydrocyclopenta[f]indol-3-yl}-4-fluoro-N,N-dimethyl-L-prolinamide (levorotatory isomer)

42 mg of the compound obtained in step 11-2 was used as the starting raw material to obtain 32 mg of the titled compound (colorless, amorphous) by the same method as in step 1-5.

$[\alpha]_D^{28}$=−67° (c=0.236, chloroform) MS (ESI pos.) m/z: 714([M+H]$^+$, 736([M+Na]$^+$) $^1$H-NMR (300 MHz, DMSO-d$_6$) δ (ppm); 1.77-1.97 (m, 1H), 1.98-3.10 (m, 4H), 2.00-2.14 (m, 2H), 2.34 (s, 3H), 2.44-2.56 (m, 3H), 2.67-2.84 (m, 2H), 2.96 (t, J=7.3 Hz, 2H), 3.52 (s, 3H), 3.76 (s, 3H), 4.39-4.96 (m, 2H), 5.19-5.38 (m, 1H), 6.46-6.78 (m, 6H), 6.88 (t, J=7.5 Hz, 1H), 6.97-7.18 (m, 4H), 7.70 (s, 1H), 7.78 (s, 1H), 8.00 (d, J=9.0 Hz, 1H)

Step 11-4: Synthesis of (4R)-1-[1-(2,4-dimethoxyphenyl)sulfonyl]-3-(2-hydroxyphenyl)-2-oxo-1,2,3,5,6,7-hexahydrocyclopenta[f]indol-3-yl]-4-fluoro-N,N-dimethyl-L-prolinamide (levorotatory isomer)

10 mg of 20% palladium hydroxide (50% water content) was added to a 1 mL methanol solution of 42 mg of the compound obtained in step 11-3, and the reaction mixture was stirred for 75 minutes at room temperature under a hydrogen atmosphere. Upon completion of the reaction, the palladium was filtered off with celite, and the filtrate was concentrated under reduced pressure. The residue thus obtained was purified by column chromatography (silica gel 60, mobile phase: ethyl acetate/hexane=3/1; v/v) to obtain 21 mg of the titled compound (colorless, amorphous).

$[\alpha]_D^{29}$=−203° (c=0.110, chloroform) MS (ESI pos.) m/z: 624([M+H]$^+$, 646([M+Na]$^+$, (ESI neg.) m/z: 622([M−H]$^-$) $^1$H-NMR (500 MHz, MeOH-d$_4$) δ (ppm); 1.90-2.14 (m, 4H), 2.15-2.33 (m, 1H), 2.50-3.00 (m, 11H), 3.40 (s, 3H), 3.46-3.64 (m, 1H), 3.84 (s, 3H), 5.15-5.26 (m, 1H), 6.51 (s, 1H), 6.59-6.68 (m, 3H), 6.70-6.83 (m, 3H), 7.09 (t, J=7.8 Hz, 1H), 7.29 (s, 1H), 7.70 (s, 1H), 7.98 (d, J=9.2 Hz, 1H)

EXAMPLE 12

Synthesis of (4R)-1-[1-[(2,4-dimethoxyphenyl)sulfonyl]-3-(2-fluorophenyl)-2-oxo-5-(trifluoromethyl)-2,3-dihydro-1H-indol-3-yl]-4-fluoro-N,N-dimethyl-L-prolinamide (levorotatory isomer)

Step 12-1: Synthesis of 3-(2-fluorophenyl)-3-hydroxy-5-(trifluoromethyl)-1,3-dihydro-2H-indol-2-one 16.8 mL of a hexane-cyclohexane solution of 1.0 mol/L sec-butyllithium was added dropwise under −78° C. cooling to a 15 mL tetrahydrofuran solution of 2 g of tert-butyl[4-(trifluoromethyl)phenyl]carbamate, and the reaction mixture was stirred for 1 hour. The temperature was then raised to −40° C., and the reaction mixture was stirred for 2.5 hours at that temperature. The reaction mixture was cooled back down to −78° C., a 7.5 mL tetrahydrofuran solution of 2.23 g of ethyl(2-fluorophenyl)(oxo)acetate was added dropwise, and the reaction mixture was stirred for 2 hours at the same temperature. The temperature was then raised to room temperature, and the reaction mixture was stirred for 12 hours. A saturated ammonium chloride aqueous solution was added to the reaction solution, extraction was performed with ethyl acetate, the organic layer was washed with saturated brine and dried with magnesium sulfate, and the solvent was distilled off under reduced pressure. The residue was purified by column chromatography (silica gel 60, mobile phase: ethyl acetate/hexane=1/1; v/v) to obtain 389 mg of the titled compound (colorless powder).

MS (ESI pos.) m/z: 334([M+Na]$^+$), (ESI neg.) m/z: 332 ([M−H]$^-$) $^1$H-NMR (300 MHz, DMSO-d$_6$) δ (ppm); 7.01-7.13 (m, 2H), 7.18 (d, J=1.9 Hz, 1H), 7.29-7.45 (m, 2H), 7.59-7.68 (m, 1H), 7.88-8.02 (m, 1H), 10.95 (s, 1H)

Step 12-2: Synthesis of (4R)-4-fluoro-1-[3-(2-fluorophenyl)-2-oxo-5-(trifluoromethyl)-2,3-dihydro-1H-indol-3-yl]-N,N-dimethyl-L-prolinamide (diastereoisomer mixture)

0.12 mL of pyridine was added to a 5 mL chloroform solution of 389 mg of the compound obtained in step 12-1, and a 1 mL chloroform solution of 0.11 mL of thionyl chloride was added dropwise under ice cooling, after which the reaction mixture was stirred for 0.5 hour at room temperature. 0.87 mL of triethylamine and a 3 mL chloroform solution of 240 mg of the compound obtained in step 9-2 were added under ice cooling to this reaction solution, after which the reaction mixture was stirred for 10 hours at room temperature. Water was added to the reaction solution, extraction was performed with chloroform, and the organic layer was washed with saturated brine and dried with magnesium sulfate, after which the solvent was distilled off under reduced pressure. The residue thus obtained was purified by column chromatography (silica gel 60, mobile phase: methanol/chloroform=1/99; v/v) to obtain 315 mg of a diastereoisomer mixture of the titled compound (colorless, amorphous).

MS (ESI pos.) m/z: 454([M+H]$^+$, 476([M+Na]$^+$), (ESI neg.) m/z: 452([M−H]$^-$) $^1$H-NMR (300 MHz, DMSO-d$_6$) δ (ppm); 1.75-4.65 (m, 11H), 5.12-5.41 (m, 1H), 6.89-8.15 (m, 7H), 10.88-11.10 (m, 1H)

Step 12-3: Synthesis of (4R)-1-[1-[(2,4-dimethoxyphenyl)sulfonyl]-3-(2-fluorophenyl)-2-oxo-5-(trifluoromethyl)-2,3-dihydro-1H-indol-3-yl]-4-fluoro-N,N-dimethyl-L-prolinamide (levorotatory isomer)

100 mg of the compound obtained in step 12-2 was used as the starting raw material to obtain 32 mg of the titled compound (colorless, amorphous) by the same method as in step 1-5.

$[\alpha]_D^{28}$=−258° (c=0.102, chloroform) MS (ESI pos.) m/z: 654([M+H]$^+$, 676([M+Na]$^+$) $^1$H-NMR (300 MHz, CDCl$_3$) δ (ppm); 1.93-2.19 (m, 1H), 2.24-2.47 (m, 1H), 2.39 (s, 3H), 2.72 (s, 3H), 2.94-3.11 (m, 1H), 3.57 (s, 3H), 3.59-3.81 (m, 1H), 3.88 (s, 3H), 4.61 (dd, J=8.8, 4.6 Hz, 1H), 5.18-5.36 (m, 1H), 6.44 (d, J=2.2 Hz, 1H), 6.60 (dd, J=8.9, 2.3 Hz, 1H), 6.71-6.84 (m, 1H), 7.14-7.32 (m, 3H), 7.60 (dd, J=8.7, 2.0 Hz, 1H), 7.91-8.02 (m, 1H), 8.12-8.23 (m, 2H)

EXAMPLE 13

Synthesis of (4R)-1-[5-chloro-1-[(2,4-dimethoxyphenyl)sulfonyl]-2-oxo-3-[2-(trifluoromethoxy)phenyl]-6-(trifluoromethyl)-2,3-dihydro-1H-indol-3-yl]-4-fluoro-N,N-dimethyl-L-prolinamide (levorotatory isomer)

Step 13-1: Synthesis of 5-chloro-3-hydroxy-3-[2-(trifluoromethoxy)phenyl]-6-(trifluoromethyl)-1,3-dihydro-2H-indol-2-one 21 mL of a heptane solution of 1.6 mol/L tert-butyllithium was added dropwise under −78° C. cooling to a 30 mL diethyl ether solution of 4.00 g of tert-butyl[4-chloro-3-(trifluoromethyl)phenyl]carbamate, and the reaction mixture was stirred for 1 hour. The temperature was then raised to −40° C., and the reaction mixture was stirred for 2.5 hours at that temperature. The reaction mixture was cooled back down to −78° C., a 15 mL tetrahydrofuran solution of 4.25 g of ethyl oxo[2-(trifluoromethoxy)phenyl]acetate was added dropwise, and the reaction mixture was stirred for 2 hours at the same temperature. The temperature was then raised to room temperature, and the reaction mixture was stirred for 15 hours. A saturated ammonium chloride aqueous solution was added to the reaction solution, extraction was performed with ethyl acetate, the organic layer was washed with saturated brine and dried with magnesium sulfate, and the solvent was distilled off under reduced pressure. The residue was purified by column chromatography (silica gel 60, mobile phase: ethyl acetate/hexane=1/4; v/v) to obtain 3.57 g of the titled compound (colorless powder).

MS (ESI neg.) m/z: 410([M−H]$^−$) $^1$H-NMR (300 MHz, DMSO-d$_6$) δ (ppm); 7.20 (s, 1H), 7.22-7.31 (m, 2H), 7.47-7.56 (m, 2H), 8.05-8.13 (m, 1H), 10.99 (s, 1H)

Step 13-2: Synthesis of (4R)-1-[5-chloro-2-oxo-3-[2-(trifluoromethoxy)phenyl]-6-(trifluoromethyl)-2,3-dihydro-1H-indol-3-yl]-4-fluoro-N,N-dimethyl-L-prolinamide 0.12 mL of pyridine was added to a 3 mL chloroform solution of 500 mg of the compound obtained in step 13-1, and 1 mL of a chloroform solution of 0.10 mL of thionyl chloride was added dropwise under ice cooling, after which the reaction mixture was stirred for 1 hour. Upon completion of the reaction, water was added and extraction was performed with chloroform. The organic layer was washed with saturated brine and dried with magnesium sulfate, and the solvent was distilled off under reduced pressure. 1.7 mL of triethylamine was added under ice cooling to a 4 mL chloroform solution of 1.45 mmol of a compound obtained by the same procedure as in step 9-2 and the residue obtained above, after which the reaction mixture was stirred for 12 hours at room temperature. Water was added to the reaction solution, extraction was performed with chloroform, the organic layer was washed with saturated brine and dried with magnesium sulfate, and then the solvent was distilled off under reduced pressure. The residue was separated and purified by column chromatography (silica gel 60, mobile phase: ethyl acetate/hexane=3/1; v/v) to obtain two kinds of diastereoisomer of the titled compound in amounts of 206 mg (isomer A: pale yellow, amorphous) and 174 mg (isomer B: pale yellow, amorphous).

Isomer A: $[\alpha]_D^{28}$=−19° (c=0.101 chloroform) MS (ESI pos.) m/z: 554([M+H]$^+$, 576([M+Na]$^+$), (ESI neg.) m/z: 552 ([M−H]$^−$) $^1$H-NMR (300 MHz, DMSO-d$_6$) δ (ppm); 1.75-2.00 (m, 1H), 2.36-2.60 (m, 1H), 2.40 (s, 3H), 2.56 (s, 3H), 3.09 (dd, J=20.9, 11.6 Hz, 1H), 3.57 (ddd, J=36.56, 12.0, 3.7 Hz, 1H), 4.70 (dd, J=8.6, 4.8 Hz, 1H), 5.19-5.49 (m, 1H), 7.09 (s, 1H), 7.21-7.31 (m, 1H), 7.37 (s, 1H), 7.49 (dd, J=6.1, 3.6 Hz, 2H), 8.15 (dd, J=6.1, 3.4 Hz, 1H), 10.89 (s, 1H)

Isomer B: $[\alpha]_D^{28}$=+51° (c=0.109, methanol) MS (ESI pos.) m/z: 554([M+H]$^+$, 576([M+Na]$^+$), (ESI neg.) m/z: 552 ([M−H]$^−$) $^1$H-NMR (300 MHz, DMSO-d$_6$) δ (ppm); 1.66-1.96 (m, 1H), 2.23-2.42 (m, 1H), 2.53 (s, 3H), 2.55 (s, 3H), 3.27-3.51 (m, 1H), 3.71-3.92 (m, 2H), 5.12-5.30 (m, 1H), 6.80 (s, 1H), 7.24 (s, 1H), 7.25-7.32 (m, 1H), 7.47-7.63 (m, 2H), 8.32 (dd, J=7.7, 1.9 Hz, 1H), 11.13 (s, 1H)

Step 13-3: Synthesis of (4R)-1-[5-chloro-1-[(2,4-dimethoxyphenyl)sulfonyl]-2-oxo-3-[2-(trifluoromethoxy) phenyl]-6-(trifluoromethyl)-2,3-dihydro-1H-indol-3-yl]-4-fluoro-N,N-dimethyl-L-prolinamide (levorotatory isomer)

97 mg of the compound obtained in step 13-2 (isomer A) was used as the starting raw material to obtain 113 mg of the titled compound (colorless, amorphous) by the same method as in step 1-5.

$[\alpha]_D^{28}$=−151° (c=0.215, chloroform) MS (ESI pos.) m/z: 754([M+H]$^+$, 776([M+Na]$^+$, (ESI neg.) m/z: 752([M−H]$^−$) $^1$H-NMR (300 MHz, CDCl$_3$) δ (ppm); 1.73-2.43 (m, 2H), 2.49 (s, 3H), 2.73 (s, 3H), 2.89 (s, 3H), 2.96 (s, 3H), 3.37-3.67 (m, 1H), 3.95-4.32 (m, 2H), 5.10-5.28 (m, 1H), 7.02 (s, 1H), 7.12-7.25 (m, 2H), 7.33-7.59 (m, 3H), 8.02 (s, 1H), 8.25 (s, 1H), 8.45 (dd, J=7.7, 1.9 Hz, 1H)

EXAMPLE 14

Synthesis of (4R)-1-[1-[(2,4-dimethoxyphenyl)sulfonyl]-3-(2-methoxyphenyl)-2-oxo-5-(trifluoromethoxy)-2,3-dihydro-1H-indol-3-yl]-4-fluoro-N,N-dimethyl-L-prolinamide (levorotatory isomer)

Step 14-1: Synthesis of (4R)-4-fluoro-1-[3-(2-methoxyphenyl)-2-oxo-5-(trifluoromethoxy)-2,3-dihydro-1H-indol-3-yl]-N,N-dimethyl-L-prolinamide 0.7 mL of thionyl chloride was added under ice cooling to a 10 mL chloroform solution of 2.24 g of 3-hydroxy-3-(2-methoxyphenyl)-5-(trifluoromethoxy)-1,3-dihydro-2H-indol-2-one and 800 mg of pyridine. The reaction mixture was stirred for 2.5 hours at the same temperature, after which the excess amounts of solvent and reagent were distilled off under reduced pressure. 22.1 g of triethylamine was added under ice cooling to a 15 mL chloroform solution of the residue thus obtained (without being isolated) and 6.57 mmol of (4R)-4-fluoro-N,N-dimethyl-L-prolinamide trifluoroacetate. The reaction mixture was stirred for 13.5 hours at room temperature, after which 20 mL of a 5% potassium carbonate aqueous solution was poured into the reaction mixture, and extraction was performed with chloroform (20 mL×3). The combined organic layer was washed with saturated brine and dried with sodium sulfate, after which the drying agent was filtered off and the solvent was distilled off under reduced pressure. The residue thus obtained was separated and purified by column chromatography (silica gel 60, mobile phase: ethyl acetate/acetone=25/1; v/v) to obtain two kinds of diastereoisomer of the titled compound in amounts of 761 mg (isomer A: colorless, amorphous) and 633 mg (isomer B: colorless, amorphous).

Isomer A: $[\alpha]_D^{25}$=+123° (c=0.291 chloroform) MS (ESI pos.) m/z: 482([M+H]$^+$), (ESI pos.) m/z: 504([M+Na]$^+$), (ESI neg.) m/z: 480([M−H]$^-$) $^1$H-NMR (300 MHz, DMSO-d$_6$) δ (ppm); 1.64-1.94 (m, 1H), 2.17-2.38 (m, 1H), 2.42-2.58 (m, 5H), 3.24-3.50 (m, 5H), 3.74-3.95 (m, 2H), 5.04-5.32 (m, 1H), 6.44 (d, J=1.7 Hz, 1H), 6.84-6.98 (m, 2H), 7.06-7.18 (m, 2H), 7.24-7.35 (m, 1H), 8.04 (dd, J=7.6, 1.7 Hz, 1H), 10.58 (s, 1H) $^1$H-NMR (300 MHz, CDCl$_3$) δ (ppm); 1.85-2.35 (m, 2H), 2.53 (s, 3H), 2.66 (s, 3H), 3.49-3.73 (m, 4H), 4.03-4.21 (m, 2H), 5.05-5.32 (m, 1H), 6.75 (d, J=2.2 Hz, 1H), 6.80-6.87 (m, 2H), 6.97-7.05 (m, 1H), 7.08-7.17 (m, 1H), 7.25-7.32 (m, 1H), 8.23 (dd, J=7.8, 1.7 Hz, 1H), 9.43 (s, 1H)

Isomer B: $[\alpha]_D^{25}$=−172° (c=0.287, chloroform) MS (ESI pos.) m/z: 504([M+Na]$^+$), (ESI neg.) m/z: 480([M−H]$^-$) $^1$H-NMR (300 MHz, DMSO-D$_6$) δ (ppm); 1.82-2.02 (m, 1H), 2.26-2.56 (m, 7H), 2.84-3.09 (m, 1H), 3.41-3.73 (m, 4H), 4.54-4.64 (m, 1H), 5.18-5.44 (m, 1H), 6.75-6.86 (m, 2H), 6.92 (d, J=8.1 Hz, 1H), 6.98-7.01 (m, 1H), 7.11-7.20 (m, 1H), 7.23-7.32 (m, 1H), 7.88 (dd, J=7.7, 1.3 Hz, 1H), 10.39 (s, 1H)

Step 14-2: Synthesis of (4R)-1-[1-[(2,4-dimethoxyphenyl)sulfonyl]-3-(2-methoxyphenyl)-2-oxo-5-(trifluoromethoxy)-2,3-dihydro-1H-indol-3-yl]-4-fluoro-N,N-dimethyl-L-prolinamide (levorotatory isomer)

254 mg of the compound obtained in step 14-1 (isomer B) was used as the starting raw material to obtain 242 mg of the titled compound (colorless, amorphous) by the same method as in step 1-5.

$[\alpha]_D^{25}$=−215° (c=0.227, chloroform) MS (ESI pos.) m/z: 682([M+H]$^+$), (ESI pos.) m/z: 704([M+Na]$^+$), (ESI neg.) m/z: 680([M−H]$^-$) $^1$H-NMR (499 MHz, CDCl$_3$) δ (ppm); 1.62-2.01 (m, 2H), 2.31 (s, 3H), 2.74 (s, 3H), 2.98-3.78 (m, 8H), 3.85 (s, 3H), 4.78-5.08 (m, 1H), 5.20-5.37 (m, 1H), 6.42 (d, J=2.1 Hz, 1H), 6.60 (dd, J=8.8, 2.4 Hz, 1H), 6.75-6.79 (m, 1H), 6.92-6.98 (m, 2H), 7.13-7.17 (m, 1H), 7.21-7.26 (m, 1H), 7.72-7.82 (m, 1H), 7.99 (d, J=9.1 Hz, 1H), 8.13-8.18 (m, 1H)

EXAMPLE 15

Synthesis of (4R)-1-[1-(2,4-dimethoxyphenyl)sulfonyl]-3-(2-methoxyphenyl)-5-methyl-2-oxo-2,3-dihydro-1H-indol-3-yl]-4-fluoro-N,N-dimethyl-L-prolinamide (levorotatory isomer, dextrorotatory isomer)

Step 15-1: Synthesis of (4R)-4-fluoro-1-[3-(2-methoxyphenyl)-5-methyl-2-oxo-2,3-dihydro-1H-indol-3-yl]-N,N-dimethyl-L-prolinamide 0.7 mL of thionyl chloride was added under ice cooling to a 10 mL chloroform solution of 800 mg of pyridine and 1.78 g of 3-hydroxy-3-(2-methoxyphenyl)-5-methyl-1,3-dihydro-2H-indol-2-one, and the reaction mixture was stirred for 1 hour at the same temperature, after which the excess amounts of solvent and reagent were distilled off under reduced pressure. 20.0 g of triethylamine was added under ice cooling to a 20 mL chloroform solution of the residue thus obtained (without being isolated) and 6.60 mmol of (4R)-4-fluoro-N,N-dimethyl-L-prolinamide trifluoroacetate. The reaction mixture was stirred for 14 hours at room temperature, after which 10 mL of a 5% potassium carbonate aqueous solution was poured into the reaction mixture, and extraction was performed with chloroform (20 mL×3). The combined organic layer was washed with saturated brine and dried with sodium sulfate, after which the drying agent was filtered off and the solvent was distilled off under reduced pressure. The residue thus obtained was purified by column chromatography (silica gel 60, mobile phase: first time: ethyl acetate/methanol=98/2 to 1/1; v/v, second time: ethyl acetate/acetone=20/1 to 10/1; v/v) to obtain 1.30 g of the titled compound (mixture of two kinds of diastereoisomer; colorless solid).

MS (ESI pos.) m/z: 412([M+H]$^+$), (ESI pos.) m/z: 434 ([M+Na]$^+$), (ESI neg.) m/z: 410([M−H]$^-$) $^1$H-NMR (300 MHz, DMSO-d$_6$) δ (ppm); 1.52-4.76 (m, 17H), 5.01-5.48 (m, 1H), 6.32-7.33 (m, 6H), 7.82-8.12 (m, 1H), 9.99-10.28 (m, 1H)

Step 15-2: Synthesis of (4R)-1-[1-[(2,4-dimethoxyphenyl)sulfonyl]-3-(2-methoxyphenyl)-5-methyl-2-oxo-2,3-dihydro-1H-indol-3-yl]-4-fluoro-N,N-dimethyl-L-prolinamide (levorotatory isomer, dextrorotatory isomer)

620 mg of the compound obtained in step 15-1 (diastereoisomer mixture) was added under ice cooling and a nitrogen atmosphere to a 10 mL N,N-dimethylformamide solution of 67 mg of sodium hydride, and the reaction mixture was stirred for 40 minutes. After this, a 2 mL N,N-dimethylformamide solution of 400 mg of 2,4-dimethoxybenzenesulfonyl chloride was added dropwise. The reaction mixture was stirred for 30 minutes at the same temperature, after which 5 mL of ethyl acetate and 10 mL of a 5% potassium carbonate aqueous solution were added, and the reaction mixture was stirred at room temperature overnight. The precipitated solids were filtered off and separated and purified by column chromatography (silica gel 60, mobile phase: ethyl acetate/acetone=99/1; v/v) to obtain two kinds of diastereoisomer of the titled compound in amounts of 184 mg (isomer A: colorless, amorphous) and 256 mg (isomer B: colorless, amorphous).

Isomer A: $[\alpha]_D^{25}$=−225° (c=0.187, chloroform) MS (ESI pos.) m/z: 612([M+H]$^+$), (ESI pos.) m/z: 634([M+Na]$^+$) $^1$H-NMR (499 MHz, CDCl$_3$) δ (ppm); 1.53-1.62 (m, 1H), 1.85-1.98 (m, 1H), 2.18-2.32 (m, 7H), 2.75 (s, 3H), 3.10-3.25 (m, 1H), 3.55-3.86 (m, 9H), 4.89-5.01 (br, 1H), 5.21-5.39 (m, 1H), 6.40 (d, J=1.8 Hz, 1H), 6.58 (dd, J=9.0, 2.3 Hz, 1H), 6.76 (d, J=7.9 Hz, 1H), 6.85-6.97 (m, 2H), 7.07 (dd, J=8.5, 1.2 Hz, 1H), 7.17-7.24 (m, 1H), 7.74-7.84 (m, 2H), 8.15 (d, J=8.8 Hz, 1H)

Isomer B: $[\alpha]_D^{25}$=+142° (c=0.240, chloroform) MS (ESI pos.) m/z: 612([M+H]$^+$), (ESI pos.) m/z: 634([M+Na]$^+$) $^1$H-NMR (499 MHz, CDCl$_3$) δ (ppm); 1.81-1.96 (m, 1H), 2.11-2.23 (m, 4H), 2.46 (s, 3H), 2.62 (s, 3H), 3.24 (s, 3H), 3.36-3.49 (m, 1H), 3.73-3.87 (m, 7H), 4.06-4.11 (m, 1H), 5.00-5.15 (m, 1H), 6.47 (d, J=2.4 Hz, 1H), 6.60 (dd, J=9.0, 2.3

Hz, 1H), 6.66-6.73 (m, 2H), 7.03-7.10 (m, 2H), 7.18-7.24 (m, 1H), 7.81 (d, J=8.2 Hz, 1H), 8.15-8.25 (m, 2H)

EXAMPLE 16

Synthesis of (4R)-1-[4,5-dichloro-1-[(2,4-dimethoxyphenyl)sulfonyl]-3-(2-methoxy-5-methylphenyl)-2-oxo-2,3-dihydro-1H-indol-3-yl]-4-fluoro-N,N-dimethyl-L-prolinamide (levorotatory isomer, dextrorotatory isomer)

Step 16-1: Synthesis of 4,5-dichloro-3-hydroxy-3-(2-methoxy-5-methylphenyl)-1,3-dihydro-2H-indol-2-one A 10 mL tetrahydrofuran solution of 3.02 g of 2-bromo-1-methoxy-4-methylbenzene was added dropwise under a nitrogen atmosphere to a suspension of 360 mg of magnesium in 10 mL of tetrahydrofuran, after which the reaction mixture was stirred for 30 minutes under heating and reflux, and then allowed to stand and cool to room temperature.

1.50 g of 4,5-dichloro-1H-indol-2,3-dione was added under ice cooling and a nitrogen atmosphere to a 40 mL tetrahydrofuran solution of 310 mg of sodium hydride, and the reaction mixture was stirred for 1 hour. After this, 20 mL of a previously prepared tetrahydrofuran solution of bromo(2-methoxy-5-methylphenyl)magnesium was added dropwise over a period of 20 minutes, and the reaction mixture was stirred for 4.5 hours at the same temperature, after which 50 mL of a saturated ammonium chloride aqueous solution was added, and the reaction mixture was stirred for 30 minutes at room temperature. After liquid separation, the aqueous layer was extracted with ethyl acetate (30 mL×3), the combined organic layer was washed with saturated brine and dried with sodium sulfate, and the drying agent was then filtered off and the solvent was distilled off under reduced pressure. The residue thus obtained was stirred and washed with isopropyl ether and the solids were filtered off to obtain 1.23 g of the titled compound (yellow solid).

MS (ESI pos.) m/z: 360([M+Na]$^+$), (ESI neg.) m/z: 336 ([M−H]$^−$) $^1$H-NMR (200 MHz, DMSO-d$_6$) δ (ppm); 2.31 (s, 3H), 3.38 (s, 3H), 6.64-6.87 (m, 3H), 7.00-7.13 (m, 1H), 7.42 (d, J=8.4 Hz, 1H), 7.68 (d, J=2.2 Hz, 1H), 10.61 (s, 1H)

Step 16-2: Synthesis of (4R)-1-[4,5-dichloro-3-(2-methoxy-5-methylphenyl)-2-oxo-2,3-dihydro-1H-indol-3-yl]-4-fluoro-N,N-dimethyl-L-prolinamide 0.18 mL of thionyl chloride was added under ice cooling to a 5 mL chloroform solution of 300 mg of pyridine and 600 mg of the compound obtained in step 16-1. The reaction mixture was stirred for 1 hour at the same temperature, after which a 5 mL chloroform solution of 430 mg of the compound obtained in step 9-2 was added without being isolated, after which 20 mL of triethylamine was added dropwise under ice cooling. The reaction mixture was stirred for 88 hours at room temperature, after which 10 mL of a 5% potassium carbonate aqueous solution was poured into the reaction mixture, and extraction was performed with chloroform (20 mL×3). The combined organic layer was washed with saturated brine and dried with sodium sulfate, and the drying agent was then filtered off and the solvent was distilled off under reduced pressure. The residue thus obtained was purified by column chromatography (silica gel 60, mobile phase: ethyl acetate) to obtain 640 mg of the titled compound (two kinds of diastereoisomer; beige, amorphous).

MS (ESI pos.) m/z: 480([M+H]$^+$), (ESI pos.) m/z: 502 ([M+Na]$^+$), (ESI neg.) m/z: 478([M−H]$^−$) $^1$H-NMR (300 MHz, DMSO-d$_6$) δ (ppm); 1.69-4.69 (m, 17H), 5.04-5.50 (m, 1H), 6.71-6.84 (m, 2H), 7.01-7.13 (m, 1H), 7.35-7.47 (m, 1H), 7.63-7.83 (m, 1H), 10.47-10.78 (m, 1H)

Step 16-3: Synthesis of (4R)-1-[4,5-dichloro-1-[(2,4-dimethoxyphenyl)sulfonyl]-3-(2-methoxy-5-methylphenyl)-2-oxo-2,3-dihydro-1H-indol-3-yl]-4-fluoro-N,N-dimethyl-L-prolinamide (levorotatory isomer, dextrorotatory isomer)

301 mg of the compound obtained in step 16-2 (diastereoisomer mixture) was added under ice cooling and a nitrogen atmosphere to a 3 mL tetrahydrofuran solution of 26 mg of sodium hydride, and the reaction mixture was stirred for 20 minutes. After this, a 2 mL tetrahydrofuran solution of 170 mg of 2,4-dimethoxybenzenesulfonyl chloride was added dropwise, and the reaction mixture was stirred for 2 hours at room temperature. Then 5 mL of ethylacetate and 10 mL of a 5% potassium carbonate aqueous solution were added and the reaction mixture was stirred for 30 minutes at room temperature. After liquid separation, the aqueous layer was extracted with ethyl acetate (10 mL×3), and the combined organic layer was dried with sodium sulfate, after which the drying agent was filtered off and the solvent was distilled off under reduced pressure. The residue thus obtained was separated and purified by column chromatography (silica gel 60, mobile phase: ethyl acetate/acetone=99/1; v/v) to obtain two kinds of diastereoisomer of the titled compound in amounts of 115 mg (isomer A: colorless, amorphous) and 127 mg (isomer B: colorless, amorphous).

Isomer A: [α]$_D^{25}$=−248° (c=0.183, chloroform) MS (ESI pos.) m/z: 680([M+H]$^+$), (ESI pos.) m/z: 702([M+Na]$^+$ $^1$H-NMR (499 MHz, CDCl$_3$) δ (ppm); 1.89 (s, 1H), 2.19-3.94 (m, 21H), 4.65-5.06 (m, 1H), 5.23-5.44 (m, 1H), 6.43 (s, 1H), 6.57 (dd, J=9.0, 2.3 Hz, 2H), 6.97-7.05 (m, 1H), 7.42 (d, J=8.8 Hz, 1H), 7.75 (s, 1H), 7.93 (d, J=8.5. Hz, 1H), 8.09-8.20 (m, 1H)

Isomer B: [α]$_D^{25}$=+211° (c=0.200, chloroform) MS (ESI pos.) m/z: 680([M+H]$^+$), (ESI pos.) m/z: 702([M+Na]$^+$) $^1$H-NMR (499 MHz, CDCl$_3$) δ (ppm); 1.88-2.23 (m, 2H), 2.33 (s, 3H), 2.55-2.81 (m, 6H), 3.36 (s, 3H), 3.47-3.63 (m, 1H), 3.79-3.88 (m, 7H), 4.07-4.19 (m, 1H), 4.95-5.19 (m, 1H), 6.48 (d, J=2.1 Hz, 1H), 6.57 (dd, J=8.8, 2.1 Hz, 1H), 6.63 (d, J=8.2 Hz, 1H), 6.99-7.07 (m, 1H), 7.41-7.48 (m, 1H), 7.67 (s, 1H), 7.92-8.01 (m, 1H), 8.13 (d, J=8.8 Hz, 1H)

EXAMPLE 17

Synthesis of (4R)-1-{5-chloro-3-(5-chloro-2-methoxyphenyl)-1-[(2,4-dimethoxyphenyl)sulfonyl]-4-methyl-2-oxo-2,3-dihydro-1H-indol-3-yl}-4-fluoro-N,N-dimethyl-L-prolinamide (levorotatory isomer)

Step 17-1: Synthesis of 5-chloro-3-(5-chloro-2-methoxyphenyl)-3-hydroxy-4-methyl-1,3-dihydro-2H-indol-2-one A 5 mL tetrahydrofuran solution of 4.75 g of 2-bromo-4-chloro-1-methoxybenzene was added dropwise under a nitrogen atmosphere to a suspension of 500 mg of magnesium in 10 mL of tetrahydrofuran, after which the reaction mixture was stirred while being heated and refluxed for 30 minutes, and then allowed to stand and cool to room temperature.

1.96 g of 5-chloro-4-methyl-1H-indol-2,3-dione was added under ice cooling and a nitrogen atmosphere to a 50 mL tetrahydrofuran solution of 440 mg of sodium hydride, and the reaction mixture was stirred for 1 hour. After this, a previously prepared 15 mL tetrahydrofuran solution of bromo(5-chloro-2-methoxyphenyl)magnesium was added dropwise over a period of 10 minutes. The reaction mixture was stirred for 3 hours at the same temperature, after which 50 mL of a saturated ammonium chloride aqueous solution was added, and the reaction mixture was stirred for another 30 minutes at room temperature. After liquid separation, the aqueous layer was extracted with ethyl acetate (30 mL×3), and the combined organic layer was washed with saturated brine and dried with sodium sulfate, and the drying agent was then filtered off and the solvent was distilled off under reduced pressure. The residue thus obtained was stirred and washed with isopropyl ether, and the solids were then filtered off to obtain 2.43 g of the titled compound (yellow solid).

MS (ESI neg.) m/z: 336([M−H]$^-$) $^1$H-NMR (300 MHz, DMSO-d$_6$) δ (ppm); 1.87 (s, 3H), 3.41 (s, 3H), 6.70 (dd, J=8.2, 0.4 Hz, 1H), 6.78 (s, 1H), 6.93 (d, J=8.7 Hz, 1H), 7.25 (dd, J=8.2, 0.4 Hz, 1H), 7.35 (dd, J=8.7, 2.8 Hz, 1H), 7.83 (d, J=2.8 Hz, 1H), 10.48 (s, 1H)

Step 17-2: Synthesis of (4R)-1-[5-chloro-3-(5-chloro-2-methoxyphenyl)-4-methyl-2-oxo-2,3-dihydro-1H-indol-3-yl]-4-fluoro-N,N-dimethyl-L-prolinamide 0.36 mL of thionyl chloride was added under ice cooling to a 10 mL chloroform solution of 420 mg of pyridine and 1.19 g of the compound obtained in step 17-1. The reaction mixture was stirred for 2 hours at the same temperature, after which the excess amounts of solvent and reagent were distilled off under reduced pressure. 3.60 g of triethylamine was added under ice cooling to a 15 mL chloroform solution of the residue thus obtained (without being isolated) and 3.53 mmol of (4R)-4-fluoro-N,N-dimethyl-L-prolinamide trifluoroacetate. The reaction mixture was stirred for 19 hours at room temperature, after which 20 mL of a 5% potassium carbonate aqueous solution was poured into the reaction mixture, and extraction was performed with chloroform (20 mL×2). The combined organic layer was washed with saturated brine and dried with sodium sulfate, after which the drying agent was filtered off and the solvent was distilled off under reduced pressure. The residue thus obtained was separated and purified by column chromatography (silica gel 60, mobile phase: ethyl acetate/acetone=98/2; v/v) to obtain two kinds of diastereoisomer of the titled compound in amounts of 880 mg (isomer A: orange solid) and 465 mg (isomer B: orange solid).

Isomer A: [α]$_D^{25}$=+205° (c=0.284 chloroform) MS (ESI pos.) m/z: 480([M+H]$^+$), (ESI pos.) m/z: 502([M+Na]$^+$), (ESI neg.) m/z: 478([M−H]$^-$) $^1$H-NMR (300 MHz, DMSO-d$_6$) δ (ppm); 1.63-1.92 (m, 4H), 2.18-2.43 (m, 4H), 2.46-2.57 (m, 3H), 3.27-3.57 (m, 4H), 3.88-4.09 (m, 2H), 5.06-5.33 (m, 1H), 6.70 (d, J=8.2 Hz, 1H), 6.97 (d, J=8.8 Hz, 1H), 7.26 (d, J=8.2 Hz, 1H), 7.36 (dd, J=8.8, 2.8 Hz, 1H), 7.87 (d, J=2.8 Hz, 1H), 10.58 (s, 1H)

Isomer B: [α]$_D^{25}$=−156° (c=0.175, chloroform) MS (ESI pos.) m/z: 480([M+H]$^+$), (ESI pos.) m/z: 502([M+Na]$^+$), (ESI neg.) m/z: 478([M−H]$^-$) $^1$H-NMR (300 MHz, DMSO-d$_6$) δ (ppm); 1.71-2.09 (m, 4H), 2.22-4.46 (m, 13H), 5.18-5.53 (m, 1H), 6.63 (d, J=8.2 Hz, 1H), 6.94 (d, J=8.7 Hz, 1H), 7.19-7.39 (m, 2H), 7.91 (d, J=2.3 Hz, 1H), 10.36 (s, 1H)

Step 17-3: Synthesis of (4R)-1-{5-chloro-3-(5-chloro-2-methoxyphenyl)-1-[(2,4-dimethoxyphenyl)sulfonyl]-4-methyl-2-oxo-2,3-dihydro-1H-indol-3-yl}-4-fluoro-N,N-dimethyl-L-prolinamide (levorotatory isomer)

258 mg of the compound obtained in step 17-2 (isomer B) was used as the starting raw material to obtain 183 mg of the titled compound (colorless, amorphous) by the same method as in step 1-5.

[α]$_D^{25}$=−249° (c=0.178, chloroform) MS (ESI pos.) m/z: 679([M+H]$^+$) $^1$H-NMR (499 MHz, CDCl$_3$) δ (ppm); 1.77-1.94 (m, 1H), 2.10-2.69 (m, 7H), 2.74-3.91 (m, 14H), 4.94 (br, 1H), 5.22-5.41 (m, 1H), 6.41 (s, 1H), 6.57 (dd, J=8.8, 2.1 Hz, 1H), 6.63-6.76 (m, 1H), 7.18 (dd, J=8.7, 2.6 Hz, 1H), 7.34 (d, J=8.8 Hz, 1H), 7.65-7.91 (m, 2H), 8.05-8.16 (m, 1H)

EXAMPLE 18

Synthesis of (4R)-1-{3-(1,3-benzodioxol-4-yl)-5-chloro-1-[(2,4-dimethoxyphenyl)sulfonyl]-2-oxo-2,3-dihydro-1H-indol-3-yl}-4-fluoro-N,N-dimethyl-L-prolinamide (levorotatory isomer, dextrorotatory isomer)

Step 18-1: Synthesis of (4R)-1-[3-(1,3-benzodioxol-4-yl)-5-chloro-2-oxo-2,3-dihydro-1H-indol-3-yl]-4-fluoro-N,N-dimethyl-L-prolinamide 0.36 mL of thionyl chloride was added under ice cooling to a 10 mL chloroform solution of 420 mg of pyridine and 1.06 g of 3-(1,3-benzodioxol-4-yl)-5-chloro-3-hydroxy-1,3-dihydro-2H-indol-2-one. The reaction mixture was stirred for 2 hours at the same temperature, after which the excess amounts of solvent and reagent were distilled off under reduced pressure. 3.63 g of triethylamine was added under ice cooling to a 15 mL chloroform solution of the residue thus obtained (without being isolated) and 3.53 mmol of (4R)-4-fluoro-N,N-dimethyl-L-prolinamide trifluoroacetate. The reaction mixture was stirred for 2.5 hours at room temperature, after which 10 mL of a 5% potassium carbonate aqueous solution was poured into the reaction mixture, and extraction was performed with chloroform (20 mL×2). The combined organic layer was washed with saturated brine and dried with sodium sulfate, after which the drying agent was filtered off and the solvent was distilled off under reduced pressure. The residue thus obtained was purified by column chromatography (silica gel 60, mobile phase: ethyl acetate/acetone=98/2; v/v) to obtain 418 mg of the titled compound (mixture of two kinds of diastereoisomer; yellow, amorphous).

MS (ESI pos.) m/z: 446([M+H]$^+$), (ESI pos.) m/z: 468([M+Na]$^+$), (ESI neg.) m/z: 444([M−H]$^-$) $^1$H-NMR (200 MHz, DMSO-d$_6$) δ (ppm); 1.65-4.87 (m, 11H), 4.95-5.57 (m, 1H), 5.76-5.92 (m, 2H), 6.69-7.47 (m, 6H), 10.50-10.84 (m, 1H)

Step 18-2: Synthesis of (4R)-1-{3-(1,3-benzodioxol-4-yl)-5-chloro-1-[(2,4-dimethoxyphenyl)sulfonyl]-2-oxo-2,3-dihydro-1H-indol-3-yl}-4-fluoro-N,N-dimethyl-L-prolinamide (levorotatory isomer, dextrorotatory isomer)

353 mg of the compound obtained in step 18-1 (mixture of diastereoisomers) was added under ice cooling and a nitrogen atmosphere to a suspension of 35 mg of sodium hydride in 3 mL of tetrahydrofuran, and the reaction mixture was stirred for 20 minutes. After this, a 2 mL tetrahydrofuran solution of 219 mg of 2,4-dimethoxybenzenesulfonyl chloride was added dropwise. The reaction mixture was stirred for 2 hours at the same temperature, after which 5 mL of ethyl acetate and 10 mL of a 5% potassium carbonate aqueous solution were added, and the reaction mixture was stirred for 30 minutes at room temperature. After liquid separation, the aqueous layer was extracted with ethyl acetate (10 mL×3), and the combined organic layer was dried with sodium sulfate, after which the drying agent was filtered off and the solvent was distilled off under reduced pressure. The residue thus obtained was separated and purified by column chromatography (silica gel 60, mobile phase: ethyl acetate) to obtain two kinds of diastereoisomer of the titled compound in amounts of 191 mg (isomer A: colorless, amorphous) and 75 mg (isomer B: colorless, amorphous).

Isomer A: $[\alpha]_D^{25}=-222°$ (c=0.176, chloroform) MS (ESI pos.) m/z: 646([M+H]$^+$), (ESI pos.) m/z: 668([M+Na]$^+$) $^1$H-NMR (499 MHz, CDCl$_3$) δ (ppm); 1.99-2.24 (m, 2H), 2.43 (s, 3H), 2.66-2.76 (m, 4H), 3.52-3.63 (m, 4H), 3.86 (s, 3H), 4.77-4.82 (m, 1H), 5.14-5.30 (m, 1H), 5.51-5.63 (m, 2H), 6.40 (d, J=2.1 Hz, 1H), 6.60 (dd, J=8.8, 2.4 Hz, 1H), 6.67-6.71 (m, 1H), 6.73-6.79 (m, 1H), 7.07 (dd, J=8.2, 1.2 Hz, 1H), 7.28 (dd, J=8.8, 2.4 Hz, 1H), 7.41 (d, J=2.4 Hz, 1H), 7.91 (d, J=8.8 Hz, 1H), 8.18 (d, J=9.1 Hz, 1H)

Isomer B: $[\alpha]_D^{25}=+157°$ (c=0.185, chloroform) MS (ESI pos.) m/z: 668([M+Na]$^+$) $^1$H-NMR (499 MHz, CDCl$_3$) δ (ppm); 1.88-2.03 (m, 1H), 2.22-2.33 (m, 1H), 2.55 (s, 3H), 2.70 (s, 3H), 3.40-3.53 (m, 1H), 3.57 (s, 3H), 3.75-3.89 (m, 4H), 4.04 (dd, J=9.5, 6.7 Hz, 1H), 5.06-5.24 (m, 2H), 5.41 (d, J=1.5 Hz, 1H), 6.42 (d, J=2.1 Hz, 1H), 6.59 (dd, J=9.0, 2.2 Hz, 1H), 6.69 (dd, J=7.9, 1.2 Hz, 1H), 6.83-6.91 (m, 1H), 7.07 (d, J=2.4 Hz, 1H), 7.28 (dd, J=8.8, 2.4 Hz, 1H), 7.51 (d, J=7.0 Hz, 1H), 7.93 (d, J=8.8 Hz, 1H), 8.20 (d, J=8.8 Hz, 1H)

EXAMPLE 19

Synthesis of (4R)-1-[5-chloro-1-[(2,4-dibutoxyphenyl)sulfonyl]-3-(2-methoxyphenyl)-2-oxo-2,3-dihydro-1H-indol-3-yl]-4-fluoro-N,N-dimethyl-L-prolinamide (levorotatory isomer)

Step 19-1: Synthesis of 1,3-dibutoxybenzene 25.5 g of butyl bromide was added to a 150 mL acetone solution of 26.4 g of potassium carbonate and 10.0 g of resorcinol, after which the reaction mixture was stirred for 6 hours at 90° C. 100 mL of a saturated ammonium chloride aqueous solution was poured into the reaction solution under stirring, following by 30 minutes more stirring, after which the solvent was distilled off under reduced pressure. 200 mL of water was added, after which extraction was performed with ethyl acetate (200 mL×3). The organic layer was washed with saturated brine and dried with magnesium sulfate, and the drying agent was then filtered off and the solvent was distilled off under reduced pressure. The residue thus obtained was separated and purified by column chromatography (silica gel 60, mobile phase: hexane/ethyl acetate=95/5 to 1/1; v/v) to obtain 11.0 g of the titled compound (colorless oily substance).

MS (ESI pos.) m/z: 223([M+H]$^+$) $^1$H-NMR (300 MHz, CDCl$_3$) δ (ppm); 0.90-1.06 (m, 6H), 1.39-1.59 (m, 4H), 1.68-1.85 (m, 4H), 3.88-4.01 (m, 4H), 6.43-6.53 (m, 3H), 7.09-7.20 (m, 1H)

Step 19-2: Synthesis of potassium 2,4-dibutoxybenzenesulfonate 1.4 mL of trimethylsilyl chlorosulfonate was added dropwise over a period of 10 minutes under ice cooling and a nitrogen atmosphere to a 10 mL 1,2-dichloroethane solution of 2.00 g of the compound obtained in step 19-1. The reaction mixture was stirred for 10 minutes at the same temperature, after which 5 mL of water and 5 mL of chloroform were added, and the reaction mixture was stirred for 5 more minutes. Extraction was performed with water (20 mL×3), after which 5 mL of a 1 mol/L potassium hydroxide aqueous solution was added to the aqueous layer. After 30 minutes of stirring, the solvent was distilled off under reduced pressure to obtain 4.02 g of the titled compound (colorless solid).

MS (ESI neg.) m/z: 301([M−K]$^-$) $^1$H-NMR (300 MHz, DMSO-d$_6$) δ (ppm); 0.82-1.01 (m, 6H), 1.33-1.76 (m, 8H), 3.84-4.06 (m, 4H), 6.29-6.51 (m, 2H), 7.58 (d, J=8.4 Hz, 1H)

Step 19-3: Synthesis of 2,4-butoxybenzenesulfonyl chloride 30.7 g of phosphoryl chloride was added under ice cooling and a nitrogen atmosphere to 3.90 g of the compound obtained in step 19-2, and the reaction mixture was stirred for 5.5 hours at 130° C. After cooling to room temperature, the reaction mixture was poured into 200 mL of ice block, and the mixture was stirred for 20 minutes, and then 50 mL of diethyl ether was added and the reaction mixture was stirred for another 30 minutes. Extraction was performed with diethyl ether (50 mL×2), after which the organic layer was washed with saturated brine and dried with magnesium sulfate. The drying agent was then filtered off and the solvent was distilled off under reduced pressure. The residue thus obtained was separated and purified by column chromatography (silica gel 60, mobile phase: hexane/ethyl acetate=9/1; v/v) to obtain 1.53 g of the titled compound (colorless solid).

MS (ESI pos.) m/z: 343([M+Na]$^+$) $^1$H-NMR (300 MHz, CDCl$_3$) δ (ppm); 0.92-1.06 (m, 6H), 1.42-1.67 (m, 4H), 1.72-1.96 (m, 4H), 3.98-4.18 (m, 4H), 6.44-6.56 (m, 2H), 7.86 (d, J=9.6 Hz, 1H)

Step 19-4: Synthesis of (4R)-1-[5-chloro-1-[(2,4-dibutoxyphenyl)sulfonyl]-3-(2-methoxyphenyl)-2-oxo-2,3-dihydro-1H-indol-3-yl]-4-fluoro-N,N-dimethyl-L-prolinamide (levorotatory isomer)

200 mg of the compound obtained in step 1-4 (isomer B) was added under ice cooling to a suspension of 20 mg of sodium hydride in 3 mL of tetrahydrofuran, and the reaction mixture was stirred for 20 minutes. After this, 2 mL of a tetrahydrofuran solution of 160 mg of 2,4-dibutoxybenzenesulfonyl chloride was added dropwise. The reaction mixture was stirred for 2 hours at the same temperature, after which 5 mL of ethyl acetate and 10 mL of a 5% potassium carbonate aqueous solution were added, and the reaction mixture was stirred for 30 minutes at room temperature. After liquid separation, the aqueous layer was extracted with ethyl acetate (10 mL×3), and the combined organic layer was dried with sodium sulfate, after which the drying agent was filtered off and the solvent was distilled off under reduced pressure. The residue thus obtained was separated and purified by column chromatography (silica gel 60, mobile phase: n-hexane/ethyl acetate=65/35; v/v) to obtain 221 mg of the titled compound (colorless, amorphous).

$[\alpha]_D^{25}$=−220° (c=0.192, chloroform) MS (ESI pos.) m/z: 716([M+H]$^+$), (ESI pos.) m/z: 738([M+Na]$^+$) $^1$H-NMR (499 MHz, CDCl$_3$) δ (ppm); 0.85 (t, J=7.2 Hz, 3H), 0.95 (t, J=7.3 Hz, 3H), 1.16-1.94 (m, 10H), 2.18-2.40(m, 4H), 2.76 (s, 3H), 3.15-4.05 (m, 8H), 4.86 (brs, 1H), 5.23-5.44 (m, 1H), 6.39 (d, J=2.1 Hz, 1H), 6.56 (dd, J=8.8, 2.1 Hz, 1H), 6.76 (d, J=8.5 Hz, 1H), 6.93 (t, J=7.6 Hz, 1H), 7.02-7.10 (m, 1H), 7.20-7.25 (m, 2H), 7.68-7.75 (m, J=7.9 Hz, 1H), 7.95 (d, J=8.8 Hz, 1H), 8.13 (d, J=9.1 Hz, 1H)

Tables 1-1 and 1-2 show the structural formulas of the compounds of the present invention in Examples 1 to 19.

TABLE 1-1

| Example | Structual Formula |
|---------|-------------------|
| 1 | |
| 2 | |
| 3 | |
| 4 | |
| 5 | |

TABLE 1-1-continued

| Example | Structual Formula |
|---|---|
| 6 | (structure) |
| 7 | (structure) |
| 8 | (structure) |
| 9 | (structure) |
| 10 | (structure) |
| 11 | (structure) |

TABLE 1-1-continued
| Example | Structual Formula |
|---|---|
| 12 | 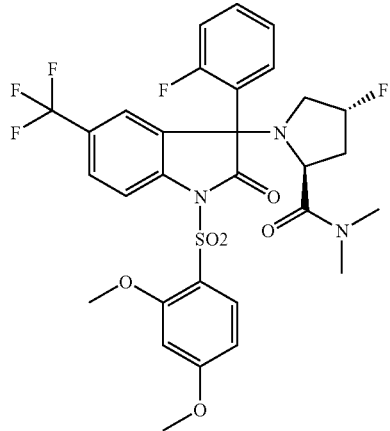 |
| 13 | 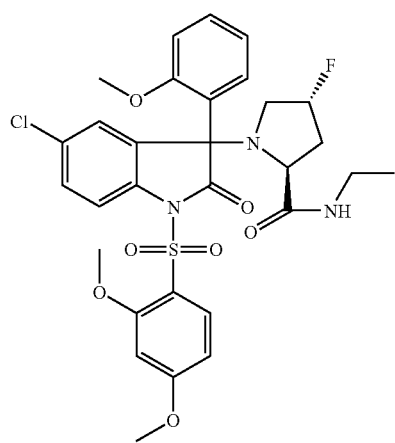 |
| 14 | 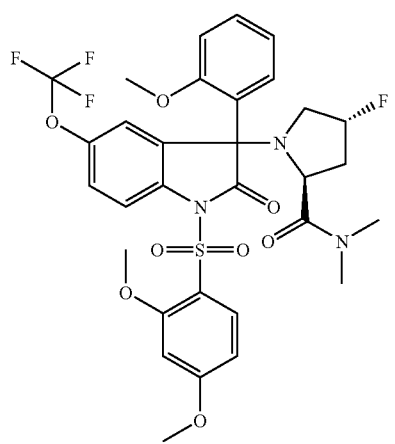 |
TABLE 1-1-continued
| Example | Structual Formula |
|---|---|
| 15 | 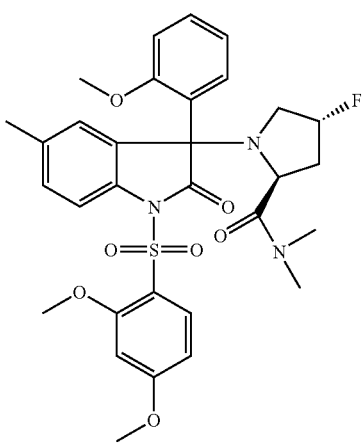 |
| 16 | 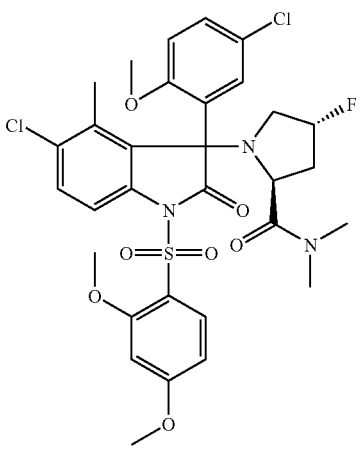 |
| 17 | |

TABLE 1-1-continued

| Example | Structual Formula |
|---|---|
| 18 | 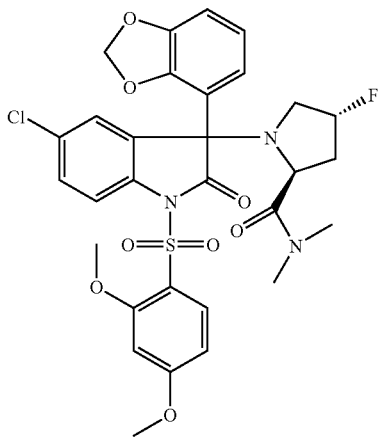 |
| 19 | 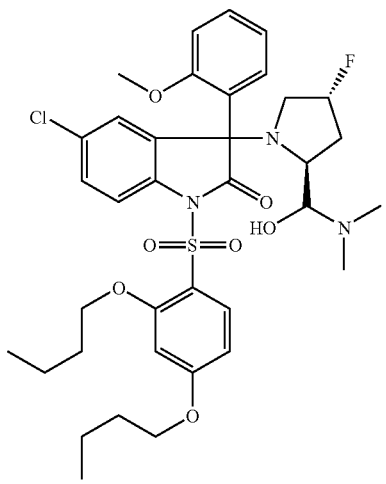 |

TEST EXAMPLE 1

V1b and V1a Receptor Binding Experiment

Preparation of crude membranes from tissues and a V1b and V1a receptor binding experiment were conducted according to the method reported in J. Clin. Invest. 98, 2729-2738 (1996). Rat pituitary gland was used for the V1b receptor binding experiment, while a membrane preparation from rat liver tissue was used for the V1a receptor binding experiment. The compounds of Examples 1, 2, and 3 were used for the test compounds.

The rats were decapitated, and the pituitary gland and liver were immediately excised. The pituitary gland and liver tissue were homogenized with a 20 vol/wet weight of 50 mmol/L Tris-hydrochloride buffer (pH 7.4, containing 10 mmol/L magnesium chloride). The homogenate was centrifuged for 5 minutes at 1500 rpm and 4° C. to remove the nuclei and tissue debris. The supernatant was centrifuged for 20 minutes at 48,000×g and 4° C. The pellet was homogenized with a 50 mmol/L Tris-hydrochloride buffer (pH 7.4, containing 10 mmol/L magnesium chloride), and centrifuged for 20 minutes at 48,000×g and 4° C. The pellet thus obtained was suspended in a 50 mmol/L Tris-hydrochloride buffer (pH 7.4) containing 10 mmol/L magnesium chloride and 0.1% bovine serum albumin to give the protein concentration 600 µg/mL, and this was used for the binding experiment as a crude membrane preparation. The crude membrane preparation (0.5 mL, 300 µg protein/assay) was incubated for 60 minutes at 25° C. with [$^3$H]Arg-vasopressin (final concentration: 0.4 nmol/L). Upon completion of the reaction, the reaction solution was filtrated over GF/C glass fiber filter paper that had been soaked for 2 hours in 0.3% polyethyleneimine, using a cell harvester for a receptor binding experiment. The glass fiber filter paper was thoroughly dried, after which a scintillator was added, and the radioactivity on the filter paper was measured with a liquid scintillation counter. The amount of binding in the presence of 5 µmol/L Arg-vasopressin was regarded as the nonspecific binding, and the specific binding was determined by subfracting nonspecific binding from the total binding, which is the binding in the absence of 5 µmol/L Arg-vasopressin. The test compound was dissolved in a 100% DMSO solution and added to the membrane preparation simultaneously with the [$^3$H]Arg-vasopressin. The IC50 value of the test compound was calculated from the inhibition curve at a concentration of 0.1 nmol/L to 1 µmol/L. The concentration of the compounds which causes 50% inhibition discussed in Examples 1, 2, and 3 was 1 to $100 \times 10^{-9}$ mol/L for the V1b receptor, and was $10^{-8}$ to $10^{-6}$ mol/L for the V1a receptor.

TEST EXAMPLE 2

Measurement of Drug Concentration in Plasma and Brain following Oral Administration to Rats The compound of Example 1 and compound A (WO01/55130, listed in EXEMPLE 1) were orally administered to Sprague-Dawley rats (male, 8 weeks) at a dose of 5 mL/kg (10 mg/kg) as solutions (each compound was dissolved with 0.03 mol/L HCl containing 5% Cremophor EL, and concentration was prepared by 2 mg/ml).

Blood was collected from the tail vein at 1 and 2 hours after administration. Immediately the brain was excised, 20% homogenate was prepared with distilled water, for assay sample. Similarly, 0.3 mL of blood was collected from the tail vein at 2, 4, 8, and 24 hours following administration, and the plasma following centrifugation was used as a sample.

The concentrations of the compound of Example 1 and compound A in plasma were measured using liquid chromatography tandem mass spectrometry (LC/MS/MS). Specifically, 200 µL of acetonitrile was added to 50 µL of plasma or brain homogenate, vortex mixed and centrifuged. The resulting supernatant was put in a liquid chromatograph with an Agilent Zorbax SB-C18 5 µm column (50 mm long, 2.1 mm in diameter). The elute was 0.1% acetic acid/acetonitrile containing 0.1% acetic acid. The MS/MS detection were performed using a Sciex API3000 LC/MS/MS system with ESI for ionization, in positive ions and MRM mode for monitoring. The m/z 632→472 and m/z 630→472 were monitored for the compound of Example 1 and compound A, respectively.

The concentration of plasma and brain at each sampling point and mean plasma levels after oral administration were shown in Table 2 and Table 3, respectively.

The brain levels of the compound of Example 1, in which fluorine was introduced into the pyrrolidine ring, were higher than those of compound A at 1 and 2 hours, and it was also confirmed that Example 1 exhibited the higher plasma levels after 2 hours compared with compound A.

TABLE 2

| | | Drug concentration (units: ng/mL or ng/g) | |
|---|---|---|---|
| | | 1 hour | 2 hours |
| Compound of Example 1 | plasma | 440 | 219 |
| | brain | 35 | 11 |
| Compound A | plasma | 303 | 89 |
| | brain | 7 | ND |

(Values are given as average values of three examples. ND: below the quantification detection limit of 5 ng/mL.)

TABLE 3

| | Drug concentration in plasma (units: ng/mL) | | | |
|---|---|---|---|---|
| | 2 hours | 4 hours | 8 hours | 24 hours |
| Compound of Example 1 | 139 | 51 | 10 | ND |
| Compound A | 80 | 13 | 2 | ND |

(Values are given as average values of three examples. ND: below the quantification detection limit of 1 ng/mL.)

INDUSTRIAL APPLICABILITY

The compound of the present invention has antagonistic activity against an arginine-vasopressin V1b receptor and is useful in preventing or treating diseases such as depression, anxiety, Alzheimer's disease, Parkinson's disease, Huntington's disease, eating disorders, hypertension, gastrointestinal diseases, drug dependence, epilepsy, cerebral infarction, cerebral ischemia, cerebral edema, head trauma, inflammation, immunological diseases, and alopecia, to a method for manufacturing this compound.

The invention claimed is:

1. A 1,3-dihydro-2H-indol-2-one derivative expressed by Formula 1:

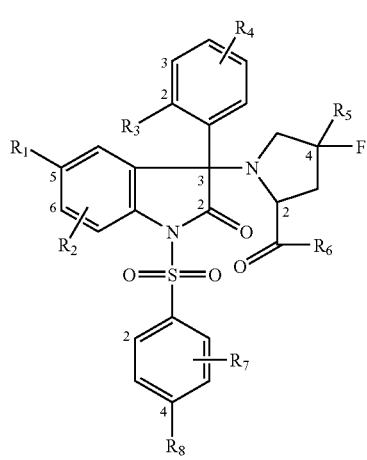

(1)

(wherein $R_1$ is a halogen atom, a $C_1$ to $C_4$ alkyl group, a $C_1$ to $C_4$ alkoxy group, a trifluoromethyl group, or a trifluoromethoxy group, $R_2$ is a hydrogen atom, a halogen atom, a $C_1$ to $C_4$ alkyl group, a $C_1$ to $C_4$ alkoxy group, or a trifluoromethyl group, or $R_2$ is in the 6-position of the indol-2-one and $R_1$ and $R_2$ join together to form a $C_3$ to $C_6$ alkylene group, $R_3$ is a halogen atom, a hydroxyl group, a $C_1$ to $C_4$ alkyl group, a $C_1$ to $C_4$ alkoxy group, or a trifluoromethoxy group, $R_4$ is a hydrogen atom, a halogen atom, a $C_1$ to $C_4$ alkyl group, or a $C_1$ to $C_4$ alkoxy group, or $R_4$ is in the 3-position of the phenyl and $R_3$ and $R_4$ join together to form a methylenedioxy group, $R_5$ is a hydrogen atom or a fluorine atom, $R_6$ is an ethylamino group, a dimethylamino group, an azetidin-1-yl group, or a $C_1$ to $C_4$ alkoxy group, $R_7$ is a $C_1$ to $C_4$ alkoxy group, and $R_8$ is a $C_1$ to $C_4$ alkoxy group), or a pharmaceutically acceptable salt thereof.

2. The 1,3-dihydro-2H-indol-2-one derivative or pharmaceutically acceptable salt thereof according to claim 1, wherein $R_1$ is a chlorine atom, a methyl group, a methoxy group, a trifluoromethyl group, or a trifluoromethoxy group, $R_2$ is a hydrogen atom, a chlorine atom, a methyl group, or a methoxy group, $R_3$ is a fluorine atom or a methoxy group, $R_4$ is a hydrogen atom, a chlorine atom, a methyl group, or a methoxy group, or $R_4$ is in the 3-position of the phenyl and $R_3$ and $R_4$ join together to form a methylenedioxy group, $R_5$ is a hydrogen atom or a fluorine atom, $R_6$ is a dimethylamino group, an azetidin-1-yl group, or a methoxy group, $R_7$ is in the 2-position of the phenyl, and is a methoxy group, and $R_8$ is a methoxy group.

3. The 1,3-dihydro-2H-indol-2-one derivative or pharmaceutically acceptable salt thereof according to claim 1, expressed by the Formula 1a:

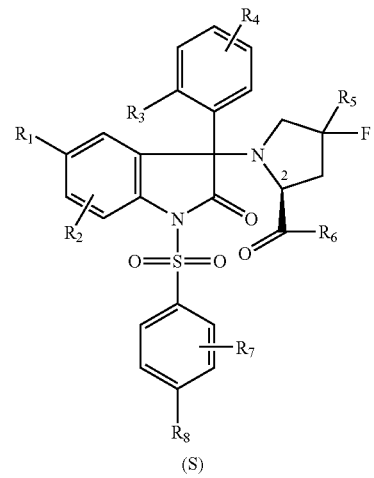

(1a)

(wherein $R_1$, $R_2$, $R_3$, $R_4$, $R_5$, $R_6$, $R_7$, and $R_8$ are the same as defined in claim 1), in which the substituent in the 2-position of the pyrrolidine has the (S) configuration.

4. The 1,3-dihydro-2H-indol-2-one derivative or pharmaceutically acceptable salt thereof according to claim 3, in the form of a levorotatory isomer.

5. The 1,3-dihydro-2H-indol-2-one derivative according to claim 3, which is one of the compounds listed below:

- (4R)-1-[5-chloro-1-[2,4-dimethoxyphenyl)sulfonyl]-3-(2-methoxyphenyl)-2-oxo-2,3-dihydro-1H-indol-3-yl]-4-fluoro-N,N-dimethyl-L-prolinamide (levorotatory isomer);

- (4S)-1-[5-chloro-1-[2,4-dimethoxyphenyl)sulfonyl]-3-(2-methoxyphenyl)-2-oxo-2,3-dihydro-1H-indol-3-yl]-4-fluoro-N,N-dimethyl-L-prolinamide (levorotatory isomer);

- 1-[5-chloro-1-[(2,4-dimethoxyphenyl)sulfonyl]-3-(2-methoxyphenyl)-2-oxo-2,3-dihydro-1H-indol-3-yl]-4,4-difluoro-N,N-dimethyl-L-prolinamide (levorotatory isomer);
- methyl(4S)-1-[5-chloro-1-[(2,4-dimethoxyphenyl)sulfonyl]-3-(2-methoxyphenyl)-2-oxo-2,3-dihydro-1H-indol-3-yl]-4-fluoro-L-prolinate (diastereoisomer mixture);
- 3-[(2S)-2-azetidin-1-ylcarbonyl)-4-fluoropyrrolidin-1-yl]-5-chloro-1-(2,4-dimethoxyphenyl)sulfonyl]-3-(2-methoxyphenyl)-1,3-dihydro-2H-indol-2-one (levorotatory isomer);
- (4R)-1-{3-(2,4-dimethoxyphenyl)-1-[(2,4-dimethoxyphenyl)sulfonyl]-5,6-dimethoxy-2-oxo-2,3-dihydro-1H-indol-3-yl}-4-fluoro-N,N-dimethyl-L-prolinamide (levorotatory isomer);
- (4R)-1-[1-[(2,4-dimethoxyphenyl)sulfonyl]-3-(2-fluorophenyl)-2-oxo-5-(trifluoromethyl)-2,3-dihydro-1H-indol-3-yl]-4-fluoro-N,N-dimethyl-L-prolinamide (levorotatory isomer);
- (4R)-1-[1-[(2,4-dimethoxyphenyl)sulfonyl]-3-(2-methoxyphenyl)-2-oxo-5-(trifluoromethoxy)-2,3-dihydro-1H-indol-3-yl]-4-fluoro-N,N-dimethyl-L-prolinamide (levorotatory isomer);
- (4R)-1-[1-[(2,4-dimethoxyphenyl)sulfonyl]-3-(2-methoxyphenyl)-5-methyl-2-oxo-2,3-dihydro-1H-indol-3-yl]-4-fluoro-N,N-dimethyl-L-prolinamide (levorotatory isomer);
- (4R)-1-[4,5-dichloro-1-[2,4-dimethoxyphenyl)sulfonyl]-3-(2-methoxy-5-methylphenyl)-2-oxo-2,3-dihydro-1H-indol-3-yl]-4-fluoro-N,N-dimethyl-L-prolinamide (levorotatory isomer);
- (4R)-1-{5-chloro-3-(5-chloro-2-methoxyphenyl)-1-[(2,4-dimethoxyphenyl)sulfonyl]-4-methyl-2-oxo-2,3-dihydro-1H-indol-3-yl}-4-fluoro-N,N-dimethyl-L-prolinamide (levorotatory isomer); and
- (4R)-1-{3-(1,3-benzodioxol-4-yl)-5-chloro-1-[(2,4-dimethoxyphenyl)sulfonyl]-2-oxo-2,3-dihydro-1H-indol-3-yl}-4-fluoro-N,N-dimethyl-L-prolinamide (levorotatory isomer).

6. A method for manufacturing a 1,3-dihydro-2H-indol-2-one derivative expressed by Formula 1:

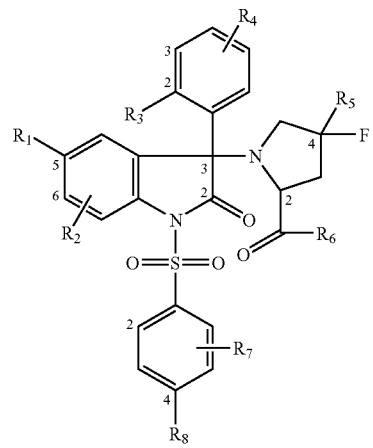

(wherein $R_1$, $R_2$, $R_3$, $R_4$, $R_5$, $R_6$, $R_7$, and $R_8$ are the same as defined in claim 1) by reacting a compound expressed by Formula 2:

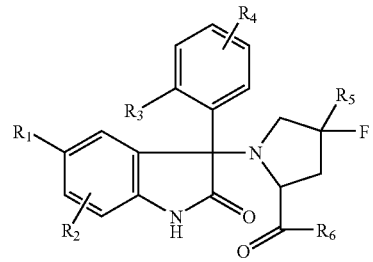

(wherein $R_1$, $R_2$, $R_3$, $R_4$, $R_5$, and $R_6$ are the same as defined in claim 1) with a compound expressed by Formula 3:

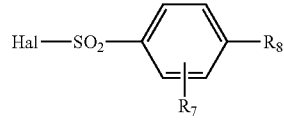

(wherein $R_7$ and $R_8$ are the same as defined in claim 1, and Hal is a halogen atom) in the presence of a base.

7. A compound expressed by Formula 2:
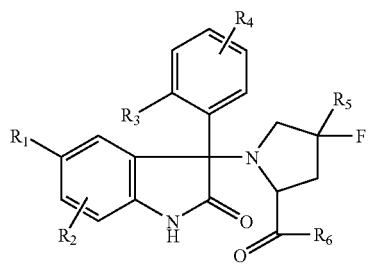
(2)
(wherein $R_1$, $R_2$, $R_3$, $R_4$, $R_5$, and $R_6$ are the same as defined in claim 1), or a salt thereof.
8. A pharmaceutical composition, containing as an active ingredient the compound or pharmaceutically acceptable salt thereof according to claim 1.
* * * * *